US007399853B2

(12) United States Patent
Freier et al.

(10) Patent No.: US 7,399,853 B2
(45) Date of Patent: Jul. 15, 2008

(54) MODULATION OF GLUCAGON RECEPTOR EXPRESSION

(75) Inventors: Susan M. Freier, San Diego, CA (US); Kenneth W. Dobie, Del Mar, CA (US); Sanjay Bhanot, Carlsbad, CA (US); Robert McKay, Poway, CA (US)

(73) Assignee: ISIS Pharmaceuticals, Carlsbad, CA (US)

( * ) Notice: Subject to any disclaimer, the term of this patent is extended or adjusted under 35 U.S.C. 154(b) by 306 days.

(21) Appl. No.: 10/832,777

(22) Filed: Apr. 27, 2004

(65) Prior Publication Data

US 2004/0266714 A1 Dec. 30, 2004

Related U.S. Application Data

(60) Provisional application No. 60/466,256, filed on Apr. 28, 2003.

(51) Int. Cl.
*C07H 21/04* (2006.01)
*C12Q 1/68* (2006.01)
*C12N 15/85* (2006.01)

(52) U.S. Cl. .......................... 536/24.5; 435/6; 435/325

(58) Field of Classification Search ....................... None
See application file for complete search history.

(56) References Cited

U.S. PATENT DOCUMENTS

| | | | |
|---|---|---|---|
| 5,563,036 A | 10/1996 | Peterson et al. | |
| 5,652,222 A | 7/1997 | Calabretta et al. | |
| 5,693,463 A | 12/1997 | Edwards et al. | |
| 5,708,158 A | 1/1998 | Hoey | |
| 5,716,780 A | 2/1998 | Edwards et al. | |
| 5,734,039 A | 3/1998 | Calabretta et al. | |
| 5,770,445 A | 6/1998 | Kindsvogel et al. | |
| 5,776,725 A | 7/1998 | Kindsvogel et al. | |
| 5,801,154 A | 9/1998 | Baracchini et al. | |
| 5,804,383 A * | 9/1998 | Gruenert et al. | 435/6 |
| 5,919,635 A | 7/1999 | Kindsvogel et al. | |
| 5,998,148 A | 12/1999 | Bennett et al. | |
| 6,251,873 B1 | 6/2001 | Furusako et al. | |
| 6,677,153 B2 * | 1/2004 | Iversen | 435/375 |
| 6,770,486 B1 | 8/2004 | Griffey et al. | |
| 2003/0087856 A1 * | 5/2003 | Bennett et al. | 514/44 |
| 2003/0144242 A1 | 7/2003 | Ward et al. | |
| 2004/0016030 A1 * | 1/2004 | Lowe et al. | 800/294 |
| 2005/0014713 A1 | 1/2005 | Freier et al. | |
| 2005/0074801 A1 | 4/2005 | Monia et al. | |
| 2005/0142581 A1 | 6/2005 | Griffey et al. | |
| 2006/0063730 A1 | 3/2006 | Monia et al. | |
| 2007/0087987 A1 | 4/2007 | Monia et al. | |

FOREIGN PATENT DOCUMENTS

| | | |
|---|---|---|
| WO | WO94/05789 | 3/1994 |
| WO | WO 94/05789 A1 | 3/1994 |
| WO | WO 00/05418 | 3/2000 |
| WO | WO2002/045494 A3 | 6/2002 |
| WO | WO 2002/045494 A3 | 6/2002 |
| WO | WO 2004/096016 A2 | 11/2004 |
| WO | WO 2004/096996 A2 | 11/2004 |
| WO | WO 2005/023995 A2 | 3/2005 |
| WO | WO 2006/34348 A1 | 3/2006 |
| WO | WO 2007/035771 A2 | 3/2007 |

OTHER PUBLICATIONS

Chambers et al., *Glucagon Receptor Gene Mutation In Essential Hypertension*, Molecular Biology & Hypertension Laboratory, Nature Genetics, vol. 12, p. 122, Feb. 1996.

Fujisawa, T., *A Mutation in the Glucagon Receptor Gene (Gly40Ser): Heterogeneity in the Association with Diabetes Mellitus*, Diabetologia, pp. 983-985, Apr. 1995.

Liang, Yin, *Reduce Glucocorticoid Receptor Expression in Liver Amellorates Diabetic Syndrome in ob/ob and db/db Mice*, Clinical Therapeutics/New Technolgoy-Pharmacologic Treatment of Diabetes or its Complications, p. A134, Article 566-P.

Lok, Si, *The Human Glucagon Receptor Encoding Gene: Structure, cDNA Sequence and Chromosomal Localization*, Elsevier Science B.V., pp. 203-209, 1994.

MacNeil, Douglas J., *Cloning and Expression of a Human Glucagon Receptor*, Biochemical and Biophyscial Research Communications, vol. 198, No. 1, pp. 328-334, Jan. 1994.

Madsen, P., *Advances in Non-Peptide Glucagon Receptor Antagonists*, Bentham Science Publishers B.V., pp. 683-691, 1999.

Siani, Alfonso, *Gly40Ser Polymorphism of the Glucagon Receptor Gene is Associated with Central Adiposity in Men*, Obesity Research, vol. 9, No. 11, pp. 722-726, Nov. 2001.

Link, J. T., "Pharmacological regulation of hepatic glucose production," *Curr. Opin. Invest. Drugs* (2003) 4(4):421-429.

PCT International Search Report for PCT/US04/13120 dated Jun. 27, 2005.

Liang, Yin, et al., "Reduction in Glucagon Receptor Expression by an Antisense Oligonucleotide Ameliorates Diabetic Syndrome in *db/db* Mice," *Diabetes*, 53: 410-417 (2004).

Database Genseq (online) Jan. 7, 2002, "Human Stat3 Amplifying RT-PCR Primer #2," Ref. WPI; 2002-034368/04. XP-002404609, Database accession No. AAD24334.

Database Genseq (online) Jan. 21, 1998, "Nucleotide Sequence of the RT-PCR Primer A," Ref. WPI; 1998-531578/45. XP-002404610, Database accession No. AAV60964.

Database Genseq (online) Jan. 16, 2004, "Novel Mutant Protein Tyrosine Kinase-Related Oligonucleotide SeqID985," Ref. WPI; 2004-718702/70. XP-002404611, Database accession No. ADT00997.

(Continued)

*Primary Examiner*—Sean McGarry
*Assistant Examiner*—Kimberly Chong
(74) *Attorney, Agent, or Firm*—Butzel Long

(57) ABSTRACT

Compounds, compositions and methods are provided for modulating the expression of glucagon receptor. The compositions comprise oligonucleotides, targeted to nucleic acid encoding glucagon receptor. Methods of using these compounds for modulation of glucagon receptor expression and for diagnosis and treatment of disease associated with expression of glucagon receptor are provided.

26 Claims, No Drawings

OTHER PUBLICATIONS

Database Genseq (online) Jan. 27, 2005, "Knock-Down Target Sequence #7049," Ref. WPI; 2004-775940/76. XP-002404612, Databse accession No. ADU41870.

Database Genseq (online) Jan. 27, 1999, "Oligonucleotide Derived From Pinene Synthase," Ref. WPI; 1999-120396/10. XP-002404613, Database accession No. AAX08680.

Database Genseq (online) Jan. 5, 2002, "Human Polymorphism Associated DNA Sequence #415," Ref. WPI; 2002-619265/66. XP-002404614, Database accession No. ABS60778.

Database Genseq (online) Jan. 30, 2000, "Hepatitis GB Virus PCR Primer SEQ ID No. 648," Ref. WPI; 2000-338307/29. XP-002404615, Database accession No. AAA55422.

Database Genseq (online) Jan. 3, 1994, "Human Glucagon Receptor Primer ZC5432," Ref. WPI; 1994-101194/12. XP-002404616, Database accession No. AAQ58770.

Database Genseq (online) Jan. 20, 2002, "Human KTOM1a Portion (ABQ63232) Probe #137," Ref. WPI; 2002-479509/51. XP-002404617, Database accession No. ABQ63424.

Database Genseq (online) Jan. 20, 2002, "Oligonucleotide SEQ ID No. 21800 for Detecting SNP TSC0004359," Ref. WPI; 2001-657177/75. XP-002404618, Database accession No. ABC21783.

Database Genseq (online) Jan. 20, 2002, "DNA Oligonucleotide Sequence #5," Ref. WPI; 2002-088875/12. XP-002404712, Database accession No. ABA92515.

Database EM-PAT, Oct. 6, 1999. XP-002404619, retrieved from EBI. Database accession No. AR065230, abstract.

Database EM-PAT, Aug. 12, 2002, "Sequence 913 from patent WO0224750." XP-002404620, Database accession No. AX475692.

Database Genseq (online) Jan. 25, 2001, "Human IL4 Gene PCR Primer SEQ ID No. 78," Ref. WPI; 2001-316132/33. XP-002404621, Database accession No. AAH18819.

Agrawal et al., "Antisense therapeutics: Is it as simple as complementary base recognition?" Mol. Med. Today: Reviews 61:72-81 (2000).

Crooke et al., "Progress in antisense technology," Annu. Rev. Med. 55:61-95 (2004).

Jen et al., "Suppression of gene expression by targeted disruption of messenger RNA: available options and current strategies," Stem Cells, 18:307-319 (2000).

Opalinska et al., "Nucleic acid therapeutics: basic principles and recent applications," Nature Reviews: Drug Discovery 1:503-514 (2002).

Taylor et al, "Antisense oligonucleotides: a systematic high-throughput approach to target a validation and gene function determination," DDT vol. 4, No. 12, Dec. 1999.

Chambers, S.M. et al., "Glucagon Receptor Gene Mutation in Essential Hypertension," Molecular Biology & Hypertension Laboratory, *Nature Genetics*, (1996)12:122.

Fujisawa, T. et al., "A Mutation in the Glucagon Receptor Gene (Gly40Ser): Heterogeneity in the Association with diabetes Mellitus," *Diabetologia*, (1995) 38:983-985.

Liang, Y. et al., "Reduce Glucocorticoid Receptor Expression in Liver Amellorates Diabetic Syndrome in ob/ob and db/db Mice," *Clinical Therapeutics/New Technology-Pharmacologic Treatment of Diabetes or its complications*, (2003) p. A134, Article 566-P.

Lok, S. et al., "The Human Glucagon Receptor Encoding Gene: Structure, cDNA Sequence and Chromosomal Localization," *Elsevier Science B.V.*, (1994) 140:203-209.

MacNeil, D.J. et al., "Cloning and Expression of a Human Glucagon Receptor," *Biochemical and Biophysical Research Communications*, (1994) 198(1):328-334.

Madsen, P. et al., "Advances in Non-Peptide Glucagon Receptor Antagonists," *Bentham Science Publishers B.V.*, (1999) 5:683-691.

Siani, A. et al., "Gly40Ser Polymorphism of the Glucagon Receptor Gene is Associated with Central Adiposty in Men," *Obesity Research*, (2001) 9(11):722-726.

* cited by examiner

MODULATION OF GLUCAGON RECEPTOR EXPRESSION

This application claims priority to U.S. provisional Application Ser. No: 60/466,256, filed Apr. 28, 2003.

FIELD OF THE INVENTION

The present invention provides compositions and methods for modulating the expression of glucagon receptor. In particular, this invention relates to compounds, particularly oligonucleotide compounds, which, in preferred embodiments, hybridize with nucleic acid molecules encoding glucagon receptor. Such compounds are shown herein to modulate the expression of glucagon receptor.

BACKGROUND OF THE INVENTION

The maintenance of normal glycemia is a carefully regulated metabolic event. Glucagon, the 29-amino acid peptide responsible for maintaining blood glucose levels in the post-absorbative state, increases glucose release from the liver by activating hepatic glycogenolysis, gluconeogenesis, stimulating lipolysis in adipose tissue, and stimulating insulin secretion. During high blood glucose levels, insulin reverses the glucagon-mediated enhancement of glycogenolysis and gluconeogenesis. In patients with diabetes, insulin is either not available or not fully effective. While treatment for diabetes has traditionally focused on increasing insulin levels, antagonism of glucagon function has been considered as an alternative therapy. As glucagon exerts its physiological effects by signaling through the glucagon receptor, the glucagon receptor has been proposed as a potential therapeutic target for diabetes (Madsen et al., *Curr. Pharm. Des.*, 1999, 5, 683-691).

Glucagon receptor is belongs to the superfamily of G-protein-coupled receptors having seven transmembrane domains. It is also a member of the smaller sub-family of homologous receptors which bind peptides that are structurally similar to glucagon. The gene encoding human glucagon receptor was cloned in 1994 and analysis of the genomic sequence revealed multiple introns and an 82% identity to the rat glucagon receptor gene (Lok et al., *Gene*, 1994, 140, 203-209.; MacNeil et al., *Biochem. Biophys. Res. Commun.*, 1994, 198, 328-334). Cloning of the rat glucagon receptor gene also led to the description of multiple alternative splice variants (Maget et al., *FEBS Lett.*, 1994, 351, 271-275). Disclosed and claimed in U.S. Pat. No. 5,776,725 is an isolated nucleic acid sequence encoding a human or rat glucagon receptor (Kindsvogel et al., 1998). The human glucagon receptor gene is localized to chromosome 17q25 (Menzel et al., *Genomics*, 1994, 20, 327-328). A missense mutation of Gly to Ser at codon 40 in the glucagon receptor gene leads to a 3-fold lower affinity for glucagon (Fujisawa et al., *Diabetologia*, 1995, 38, 983-985) and this mutation has been linked to several disease states, including non-insulin-dependent diabetes mellitus (Fujisawa et al., *Diabetologia*, 1995, 38, 983-985), hypertension (Chambers and Morris, *Nat. Genet.*, 1996, 12, 122), and central adiposity (Siani et al., *Obes. Res.*, 2001, 9, 722-726).

Inhibiting glucagon function by antagonizing the glucagon receptor has been proposed as a therapeutic target for diabetes. Currently, there are no known therapeutic agents which effectively inhibit the synthesis of glucagon receptor and to date, investigative strategies aimed at modulating glucagon receptor function have involved the use of antibodies, peptidyl antagonists, and small molecules. In addition, targeted disruption of the glucagon receptor gene in mice has shown that, despite a total absence of glucagon receptors and elevated plasma glucagon levels, the mice maintain near-normal glycemia and lipidemia (Parker et al., *Biochem. Biophys. Res. Commun.*, 2002, 290, 839-843). Patent application WO 02/45494 (Allen et al.) discloses transgenic mice comprising mutations in a glucagon receptor gene. Also claimed are agonists or antagonists of glucagon receptor, agents that modulate the function, expression or activity of a glucagon receptor gene, methods of identifying such agents, methods of ameliorating conditions associated with impaired glucose tolerance, methods of identifying agents that affect obesity, weight gain, diabetes, methods of treating obesity or diabetic conditions, and phenotypic data associated with a transgenic mouse comprising a mutation in a glucagon receptor gene.

A glucagon-neutralizing monoclonal antibody has been described that antagonizes glucagon-stimulated signal transduction in part by binding to the glucagon binding site of the glucagon receptor (Buggy et al., *Horm. Metab. Res.*, 1996, 28, 215-219). An antibody which specifically binds to the amino acid sequence of a glucagon receptor has been disclosed and claimed in U.S. Pat. No. 5,770,445 (Kindsvogel et al., 1998).

Several peptidyl antagonists of glucagon receptor have been reported in the art. Six glucagon analogs with N-terminal modifications were designed to have a higher affinity than glucagon for the glucagon receptor (Zechel et al., *Int. J. Pept. Protein Res.*, 1991, 38, 131-138). Two somatostatin analogs have been reported to be inhibitors of glucagon secretion (Rossowski and Coy, *Biochem. Biophys. Res. Commun.*, 1994, 205, 341-346).

Many small molecules have been examined as glucagon receptor antagonists including: [(+)-3,5 diisopropyl-2-(1-hydroxyethyl)-6-propyl-4'-fluoro-1,1'-biphenyl (Bay27-9955) (Petersen and Sullivan, *Diabetologia*, 2001, 44, 2018-2024), a series of alkylidene hydrazides (Ling et al., *Bioorg. Med. Chem. Lett.*, 2002, 12, 663-666), a series of 4-aryl-pyridines containing both a 3-[(1R)-hydroxyethyl] and a 2'-hydroxy group (Ladouceur et al., *Bioorg. Med. Chem. Lett.*, 2002, 12, 3421-3424), a series of 5-hydroxyalkyl-4-phenylpyridines (Ladouceur et al., *Bioorg. Med. Chem. Lett.*, 2002, 12, 461-464), a series of triarylimidazoles (Chang et al., *Bioorg. Med. Chem. Lett.*, 2001, 11, 2549-2553), a series of 2-pyridyl-3,5-diaryl pyrroles (de Laszlo et al., *Bioorg. Med. Chem. Lett.*, 1999, 9, 641-646), several substituted benzimidazoles (Madsen et al., *J. Med. Chem.*, 1998, 41, 5150-5157), and a series of pyrrolo[1,2-a]quinoxalines (Guillon et al., *Eur. J. Med. Chem.*, 1998, 33, 293-308).

There remains a long felt need for additional agents capable of effectively inhibiting glucagon receptor function. Antisense technology is an effective means for reducing the expression of specific gene products and has proven to be uniquely useful in a number of therapeutic, diagnostic, and research applications. The present invention provides compositions and methods for modulating glucagon receptor expression.

SUMMARY OF THE INVENTION

The present invention is directed to compounds, especially nucleic acid and nucleic acid-like oligomers, which are targeted to a nucleic acid encoding glucagon receptor, and which modulate the expression of glucagon receptor. Pharmaceutical and other compositions comprising the compounds of the invention are also provided. Further provided are methods of screening for modulators of glucagon receptor and methods of modulating the expression of glucagon receptor in cells, tissues or animals comprising contacting said cells, tissues or animals with one or more of the compounds or compositions of the invention. Methods of treating an animal, particularly a human, suspected of having or being prone to a disease or condition associated with expression of glucagon receptor are also set forth herein. Such methods comprise administering a therapeutically or prophylactically effective amount of one or more of the compounds or compositions of the invention to the person in need of treatment.

DETAILED DESCRIPTION OF THE INVENTION

A. Overview of the Invention

The present invention employs compounds, preferably oligonucleotides and similar species for use in modulating the function or effect of nucleic acid molecules encoding glucagon receptor. This is accomplished by providing oligonucleotides which specifically hybridize with one or more nucleic acid molecules encoding glucagon receptor. As used herein, the terms "target nucleic acid" and "nucleic acid molecule encoding glucagon receptor" have been used for convenience to encompass DNA encoding glucagon receptor, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of glucagon receptor. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403–410; Zhang and Madden, *Genome Res.*, 1997, 7, 649–656).

B. Compounds of the Invention

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid. One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611–620). Montgomery et al. have shown that the primary interference effects of dsRNA are posttranscriptional (Montgomery et al., *Proc. Natl. Acad. Sci. USA*, 1998, 95, 15502–15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806–811). Recently, it has been shown that it is, in fact, the single-stranded RNA oligomers of antisense polarity of the dsRNAs which are the potent inducers of RNAi (Tijsterman et al., *Science*, 2002, 295, 694–697).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8–80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes glucagon receptor.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding glucagon receptor, regardless of the sequence(s) of such codons. It is also known in the art that a translation termination codon (or "stop codon") of a gene may have one of three sequences, i.e., 5'-eeUAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

D. Screening and Target Validation

In a further embodiment, the "preferred target segments" identified herein may be employed in a screen for additional compounds that modulate the expression of glucagon receptor. "Modulators" are those compounds that decrease or increase the expression of a nucleic acid molecule encoding glucagon receptor and which comprise at least an 8-nucleobase portion which is complementary to a preferred target segment. The screening method comprises the steps of contacting a preferred target segment of a nucleic acid molecule encoding glucagon receptor with one or more candidate modulators, and selecting for one or more candidate modulators which decrease or increase the expression of a nucleic acid molecule encoding glucagon receptor. Once it is shown that the candidate modulator or modulators are capable of modulating (e.g. either decreasing or increasing) the expression of a nucleic acid molecule encoding glucagon receptor, the modulator may then be employed in further investigative studies of the function of glucagon receptor, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processsing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev*., 1999, 13, 3191-3197; Elbashir et al., *Nature*, 2001, 411, 494-498; Elbashir et al., *Genes Dev*. 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The compounds of the present invention can also be applied in the areas of drug discovery and target validation. The present invention comprehends the use of the compounds and preferred target segments identified herein in drug discovery efforts to elucidate relationships that exist between glucagon receptor and a disease state, phenotype, or condition. These methods include detecting or modulating glucagon receptor comprising contacting a sample, tissue, cell, or organism with the compounds of the present invention, measuring the nucleic acid or protein level of glucagon receptor and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention can be utilized for diagnostics, therapeutics (including prophylaxis) and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett*., 2000, 480, 17-24; Celis, et al., *FEBS Lett*., 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol*., 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett*., 2000, 480, 2-16; Jungblut, et al., *Electrophoresis*, 1999, 20, 2100-10), expressed sequence tag (EST) sequencing (Celis, et al., *FEBS Lett*., 2000, 480, 2-16; Larsson, et al., *J. Biotechnol*., 2000, 80, 143-57), subtractive RNA fingerprinting (SuRF) (Fuchs, et al., *Anal. Biochem*., 2000, 286, 91-98; Larson, et al., *Cytometry*, 2000, 41, 203-208), subtractive cloning, differential display (DD) (Jurecic and Belmont, *Curr. Opin. Microbiol*., 2000, 3, 316-21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (To, *Comb. Chem. High Throughput Screen*, 2000, 3, 235–41).

The compounds of the invention are useful for research and diagnostics, because these compounds hybridize to nucleic acids encoding glucagon receptor. For example, oligonucleotides that are shown to hybridize with such efficiency and under such conditions as disclosed herein as to be effective glucagon receptor inhibitors will also be effective primers or probes under conditions favoring gene amplification or detection, respectively. These primers and probes are useful in methods requiring the specific detection of nucleic acid molecules encoding glucagon receptor and in the amplification of said nucleic acid molecules for detection or for use in further studies of glucagon receptor. Hybridization of the antisense oligonucleotides, particularly the primers and probes, of the invention with a nucleic acid encoding glucagon receptor can be detected by means known in the art. Such means may include conjugation of an enzyme to the oligonucleotide, radiolabelling of the oligonucleotide or any other suitable detection means. Kits using such detection means for detecting the level of glucagon receptor in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of glucagon receptor is treated by administering antisense compounds in accordance with this invention. For example, in one non-limiting embodiment, the methods comprise the step of administering to an animal a therapeutically effective amount of a glucagon receptor inhibitor. The glucagon receptor inhibitors of the present invention effectively inhibit the activity of the glucagon receptor protein or inhibit the expression of the glucagon receptor protein. In one embodiment, the activity or expression of glucagon receptor in an animal is inhibited by about 10%. Preferably, the activity or expression of glucagon receptor in an animal is inhibited by about 30%. More preferably, the activity or expression of glucagon receptor in an animal is inhibited by 50% or more. Because the compounds herein are inhibitors of glucagon receptor, they are believed to be useful in lowering blood glucose, for example, and in treating conditions associated with glucagon receptor activity, such as high blood glucose and other metabolic conditions such as diabetes (including Type 2 diabetes), obesity, and insulin resistance.

The reduction of the expression of glucagon receptor may be measured, for example, in blood, plasma, serum, adipose tissue, liver or any other body fluid, tissue or organ of the animal. Preferably, the cells contained within said fluids, tissues or organs being analyzed contain a nucleic acid molecule encoding glucagon receptor protein and/or the glucagon receptor protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphoroedithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages—Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Preferred embodiments of the invention are oligonucleotides with phosphorothioate backbones. Also preferred are oligonucleosides with heteroatom backbones, and in particular $—CH_2—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—O—N(CH_3)—CH_2—CH_2—$ [wherein the native phosphodiester backbone is represented as $—O—P—O—CH_2—$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to C10 lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy ($2'\text{-}O—CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., $2'\text{-}O—CH_2—O—CH_2—N(CH_3)_2$, also described in examples hereinbelow.

Other preferred modifications include 2'-methoxy ($2'\text{-}O—CH_3$), 2'-aminopropoxy ($2'\text{-}OCH_2CH_2CH_2NH_2$), 2'-allyl ($2'\text{-}CH_2—CH{=}CH_2$), 2'-O-allyl ($2'\text{-}O—CH_2—CH{=}CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene $(—CH_2—)_n$ group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C{\equiv}C—CH_3$)

uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. and are presently preferred base substitutions.

Representative United States patents that teach the preparation of certain of the above noted modified nucleobases as well as other modified nucleobases include, but are not limited to, the above noted U.S. Pat. Nos. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Salts

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety. Sodium salts are especially suitable salts of the compounds of the present invention.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other pharmaceutical agents which function by a non-antisense mechanism. Examples of such pharmaceutical agents include but are not limited to cancer chemotherapeutic drugs, anti-inflammatory drugs, anti-viral drugs, and compounds for treatment of metabolic diseases such as diabetes, high blood sugar or obesity, or cardiovascular conditions such as elevated blood cholesterol or blood pressure. Combinations of antisense compounds and other non-antisense drugs are also within the scope of this invention. Two or more combined compounds may be used together or sequentially. When used with the compounds of the invention, such pharmaceutical agents may be used individually (e.g., rosiglitazone and oligonucleotide), sequentially (e.g., 5-fluorouracil and oligonucleotide for a period of time followed by methotrexate and oligonucleotide), or in combination with one or more other treatments (e.g., 5-fluorouracil, methotrexate and oligonucleotide, or 5-fluorouracil, radiotherapy and oligonucleotide).

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-$N^4$-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P═O) oligonucleotides are synthesized on an automated DNA synthesizer (Applied Biosystems model 394) using standard phosphoramidite chemistry with oxidation by iodine.

Phosphorothioates (P═S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P═O or P═S linkages are prepared as described in U.S. Pat. Nos. 5,378, 825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acidlabile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethylhydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand*,. 1990, 44, 639-641; Reddy, M. P., et al., *Tetrahedrom Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 μl of 5×annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting Glucagon Receptor In accordance with the present invention, a series of nucleic acid duplexes comprising the antisense compounds of the present invention and their complements can be designed to target glucagon receptor. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG and having a two-nucleobase overhang of deoxythymidine(dT) would have the following structure:

```
cgagaggcggacgggaccgTT     Antisense Strand
  |||||||||||||||||||
TTgctctccgcctgccctggc     Complement
```

In another embodiment, a duplex comprising an antisense strand having the same sequence CGAGAGGCGGACGGGACCG may be prepared with blunt ends (no single stranded overhang) as shown:

```
cgagaggcggacgggaccg     Antisense Strand
|||||||||||||||||||
gctctccgcctgccctggc     Complement
```

The RNA duplex can be unimolecular or bimolecular; i.e, the two strands can be part of a single molecule or may be separate molecules. RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate glucagon receptor expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12–16 hours, the oligonucleotides or oligonucleosides are recovered by precipitation out of 1 M $NH_4OAc$ with >3 volumes of ethanol. Synthesized oligonucleotides are analyzed by electrospray mass spectroscopy (molecular weight determination) and by capillary gel electrophoresis and judged to be at least 70% full length material. The relative amounts of phosphorothioate and phosphodiester linkages obtained in the synthesis is determined by the ratio of correct molecular weight relative to the −16 amu product (+/−32+/−48). For some studies oligonucleotides are purified by HPLC, as described by Chiang et al., *J. Biol. Chem.* 1991, 266, 18162–18171. Results obtained with HPLC-purified material are similar to those obtained with non-HPLC purified material.

Example 7

Oligonucleotide Synthesis—96 Well Plate Format

Oligonucleotides are synthesized via solid phase P(III) phosphoramidite chemistry on an automated synthesizer capable of assembling 96 sequences simultaneously in a 96-well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites are purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides are cleaved from support and deprotected with concentrated $NH_4OH$ at elevated temperature (55–60° C.) for 12–16 hours and the released product then dried in vacuo. The dried product is then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well is assessed by dilution of samples and UV absorption spectroscopy. The full-length integrity of the individual products is evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the compounds utilizing electrospray-mass spectroscopy. All assay test plates are diluted from the master plate using single and multi-channel robotic pipettors. Plates are judged to be acceptable if at least 85% of the compounds on the plate are at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 is obtained from the American Type Culture Collection (ATCC) (Manassas, Va.). T-24 cells are routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells are routinely passaged by trypsinization and dilution when they reached 90% confluence. Cells are seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 is obtained from the American Type Culture Collection (ATCC) (Manassas, Va.). A549 cells are routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells are routinely passaged by trypsinization and dilution when they reach 90% confluence.

NHDF Cells:

Human neonatal dermal fibroblast (NHDF) are obtained from the Clonetics Corporation (Walkersville, Md.). NHDFs are routinely maintained in Fibroblast Growth Medium (Clonetics Corporation, Walkersville, Md.) supplemented as recommended by the supplier. Cells are maintained for up to 10 passages as recommended by the supplier.

HEK Cells:

Human embryonic keratinocytes (HEK) are obtained from the Clonetics Corporation (Walkersville, Md.). HEKs are routinely maintained in Keratinocyte Growth Medium (Clonetics Corporation, Walkersville, Md.) formulated as recommended by the supplier. Cells are routinely maintained for up to 10 passages as recommended by the supplier.

HepG2 Cells:

The human hepatoblastoma cell line HepG2 is obtained from the American Type Culture Collection (Manassas, Va.). HepG2 cells are routinely cultured in Eagle's MEM supplemented with 10% fetal calf serum, non-essential amino acids, and 1 mM sodium pyruvate (Gibco/Life Technologies, Gaithersburg, Md.). Cells are routinely passaged by trypsinization and dilution when they reach 90% confluence. Cells are seeded into 96-well plates (Falcon-Primaria #3872) at a density of 7000 cells/well for use in RT-PCR analysis.

For Northern blotting or other analyses, cells may be seeded onto 100 mm or other standard tissue culture plates and treated similarly, using appropriate volumes of medium and oligonucleotide.

Primary Mouse Hepatocytes

Primary mouse hepatocytes are prepared from CD-1 mice purchased from Charles River Labs. Primary mouse hepatocytes are routinely cultured in Hepatocyte Attachment Media (Gibco) supplemented with 10% Fetal Bovine Serum (Gibco/Life Technologies, Gaithersburg, Md.), 250 nM dexamethasone (Sigma), 10 nM bovine insulin (Sigma). Cells are seeded into 96-well plates (Falcon-Primaria #3872) at a density of 10000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 65–75% confluency, they are treated with oligonucleotide. For cells grown in 96-well plates, wells are washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. Cells are treated and data are obtained in triplicate. After 4–7 hours of treatment at 37° C., the medium is replaced with fresh medium. Cells are harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of Glucagon Receptor Expression

Antisense modulation of glucagon receptor expression can be assayed in a variety of ways known in the art. For example, glucagon receptor mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of glucagon receptor can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to glucagon receptor can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays and In vivo Studies for the Use of Glucagon Receptor Inhibitors

Phenotypic Assays

Once glucagon receptor inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of glucagon receptor in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with glucagon receptor inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the glucagon receptor inhibitors. Hallmark genes, or those genes suspected to be associated with a specific disease state, condition, or phenotype, are measured in both treated and untreated cells.

In vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study. To account for the psychological effects of receiving treatments, volunteers are randomly given placebo or glucagon receptor inhibitor. Furthermore, to prevent the doctors from being biased in treatments, they may not be informed as to whether the medication they are administering is a glucagon receptor inhibitor or a placebo. Using this randomization approach, each volunteer has the same chance of being given either the new treatment or the placebo.

Volunteers may receive either the glucagon receptor inhibitor or placebo for eight week period with biological parameters associated with the indicated disease state or condition being measured at the beginning (baseline measurements before any treatment), end (after the final treatment), and at regular intervals during the study period. Such measurements may include the levels of nucleic acid molecules encoding glucagon receptor or glucagon receptor protein levels in body fluids, tissues or organs compared to pre-treatment levels. Other measurements may include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient may include age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and, typically, roughly an equal number of males and females participate in the study. Volunteers with certain characteristics are equally distributed for placebo and glucagon receptor inhibitor treatment. In general, the volunteers treated with placebo have little or no response to treatment, whereas the volunteers treated with the glucagon receptor inhibitor show positive trends in their disease state or condition index at the conclusion of the study.

One of ordinary skill will know how to conduct an appropriate clinical trial and will recognize that this is just one of many protocols which may be appropriately used.

Example 12

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 μL cold PBS. 150 μL Buffer RLT was added to each well and the plate vigorously agitated for 20 seconds. 150 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 μL of Buffer RW1 was added to each well of the RNEASY 96™ plate and incubated for 15 minutes and the vacuum was again applied for 1 minute. An additional 500 μL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Glucagon Receptor mRNA Levels

Quantitation of glucagon receptor mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMPA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5×PCR buffer minus $MgCl_2$, 6.6 mM $MgCl_2$, 375 µM each of DATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20–200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen RNA quantification reagent (Molecular Probes, Inc. Eugene, Oreg.). Methods of RNA quantification by RiboGreen are taught in Jones, L. J., et al, (Analytical Biochemistry, 1998, 265, 368–374).

In this assay, 170 µL of RiboGreen™ working reagent (RiboGreen reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers to human glucagon receptor were designed to hybridize to a human glucagon receptor sequence, using published sequence information (GenBank accession number NM_000160.1, incorporated herein as SEQ ID NO:4). For human glucagon receptor the PCR primers were:

forward primer: GACACCCCCGCCAATACC (SEQ ID NO: 5) reverse primer: CCGCATCTCTTGAACACGAA (SEQ ID NO: 6) and the PCR probe was: FAM-TTGGCACCACAAAGT-TAMRA (SEQ ID NO: 7) where FAM is the fluorescent dye and TAMRA is the quencher dye. For human GAPDH the PCR primers were:

forward primer: GAAGGTGAAGGTCGGAGTC(SEQ ID NO:8) reverse primer: GAAGATGGTGATGGGATTTC (SEQ ID NO:9) and the PCR probe was: 5' JOE-CAAGCTTCCCGTTCTCAGCC-TAMRA 3' (SEQ ID NO: 10) where JOE is the fluorescent reporter dye and TAMRA is the quencher dye.

Probes and primers to mouse glucagon receptor were designed to hybridize to a mouse glucagon receptor sequence, using published sequence information (GenBank accession number NM_008101.1, incorporated herein as SEQ ID NO: 11). For mouse glucagon receptor the PCR primers were:

forward primer: ATTTCCTGCCCCTGGTACCT (SEQ ID NO:12) reverse primer: CGGGCCCACACCTCTTG (SEQ ID NO: 13) and the PCR probe was: FAM-CCACAAAGTGCAGCACCGCCTAGTGT-TAMRA (SEQ ID NO: 14) where FAM is the fluorescent reporter dye and TAMRA is the quencher dye. For mouse GAPDH the PCR primers were:

forward primer: GGCAAATTCAACGGCACAGT(SEQ ID NO:15) reverse primer: GGGTCTCGCTCCTGGAAGAT (SEQ ID NO:16) and the PCR probe was: 5' JOE-AAGGCCGAGAATGGGAAGCTTGTCATC-TAMRA 3'(SEQ ID NO: 17) where JOE is the fluorescent reporter dye and TAMRA is the quencher dye.

Example 14

Northern Blot Analysis of Glucagon Receptor mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human glucagon receptor, a human glucagon receptor specific probe was prepared by PCR using the forward primer GACACCCCCGCCAATACC (SEQ ID NO: 5) and the reverse primer CCGCATCTCTTGAACACGAA (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

To detect mouse glucagon receptor, a mouse glucagon receptor specific probe was prepared by PCR using the forward primer ATTTCCTGCCCCTGGTACCT (SEQ ID NO: 12) and the reverse primer CGGGCCCACACCTCTTG (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™

Software V3.3 (Molecular Dynamics, Sunnyvale, Calif.). Data was normalized to GAPDH levels in untreated controls.

Example 15

Antisense Inhibition of Human Glucagon Receptor Expression by Chimeric Phosphorothioate Oligonucleotides Having 2'-MOE Wings and a Deoxy Gap In accordance with the present invention, a series of antisense compounds were designed to target different regions of the human glucagon receptor RNA, using published sequences (GenBank accession number NM_000160.1, incorporated herein as SEQ ID NO: 4, a concatenation of three contigs from GenBank accession number AC069004.2, incorporated herein as SEQ ID NO: 18, and GenBank accession number AJ245489.1, incorporated herein as SEQ ID NO: 19). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of of 2'-methoxyethyl (2'-MOE) nucleotides. The intrnucleoside (backbone) linkages are phosphorothioate (P=S) throughout the oligonucleotide. All cytidine residues are 5-methylcytidines. The compounds were analyzed for their effect on human glucagon receptor mRNA levels by quantitative real-time PCR as described in other examples herein. Data are averages from three experiments in which HepG2 cells were treated with the antisense oligonucleotides of the present invetion. The positive control for each datapoint is identified in the table by sequence ID number. If present, "N.D." indicates "no data".

TABLE 1

Inhibition of human glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 310462 | Coding | 4 | 560 | ccgcatctcttgaacacgaa | 61 | 20 |
| 299881 | 5'UTR | 4 | 97 | ttgagcctcagggcccgcgc | 56 | 21 |
| 299882 | 5'UTR | 4 | 121 | gtgtcctcccctgaagctgc | 68 | 22 |
| 299883 | 5'UTR | 4 | 163 | gagtggcagagcagcagagc | 38 | 23 |
| 299884 | 5'UTR | 4 | 192 | tgtgtgtgtacgctcctccg | 76 | 24 |
| 299885 | 5'UTR | 4 | 198 | tcctggtgtgtgtgtacgct | 67 | 25 |
| 299886 | 5'UTR | 4 | 205 | aatgcagtcctggtgtgtgt | 30 | 26 |
| 299887 | 5'UTR | 4 | 254 | ctgggcagctagctgcctcc | 38 | 27 |
| 299888 | Start Codon | 4 | 263 | ggcatgcctctgggcagcta | 73 | 28 |
| 299889 | Coding | 4 | 462 | ccagcaggaatacttgtcga | 43 | 29 |
| 299890 | Coding | 4 | 328 | ggacctgtggctggcaggcc | 72 | 30 |
| 299891 | Coding | 4 | 350 | aagtccatcacctgagcgga | 39 | 31 |
| 299892 | Coding | 4 | 361 | tctcaaacaggaagtccatc | 37 | 32 |
| 299893 | Coding | 4 | 366 | ccacttctcaaacaggaagt | 24 | 33 |
| 299894 | Coding | 4 | 386 | cactggtcaccgtagagctt | 31 | 34 |
| 299895 | Coding | 4 | 391 | ggtgacactggtcaccgtag | 40 | 35 |
| 299896 | Coding | 4 | 431 | cacaccagctccgtgggagg | 35 | 36 |
| 299897 | Coding | 4 | 442 | aggttctgttgcacaccagc | 76 | 37 |
| 299898 | Coding | 4 | 453 | atacttgtcgaaggttctgt | 28 | 38 |
| 299899 | Coding | 4 | 539 | cggtgttgcactttgtggtg | 85 | 39 |
| 299900 | 5'UTR | 19 | 546 | ccctggcagagacagcggca | 79 | 40 |
| 299901 | Coding | 4 | 552 | cttgaacacgaagcggtgtt | 83 | 41 |
| 299902 | Coding | 4 | 564 | gggcccgcatctcttgaaca | 87 | 42 |

TABLE 1-continued

Inhibition of human glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 299903 | intron: exon junction | 18 | 15279 | cttctgcgagttacagtggc | 58 | 43 |
| 299904 | Coding | 4 | 651 | ctggacctcaatctcctcgc | 43 | 44 |
| 299905 | Coding | 4 | 656 | tccttctggacctcaatctc | 5 | 45 |
| 299906 | Coding | 4 | 663 | ggccacctccttctggacct | 80 | 46 |
| 299907 | Coding | 4 | 669 | catcttggccacctccttct | 39 | 47 |
| 299908 | Coding | 4 | 681 | gaagctgctgtacatcttgg | 71 | 48 |
| 299909 | Coding | 4 | 751 | cccccaggatggccaaggcg | 69 | 49 |
| 299910 | Coding | 4 | 830 | acggagctggctttcagcac | 49 | 50 |
| 299911 | Coding | 4 | 866 | ctgtagcgggtcctgagcag | 48 | 51 |
| 299912 | Coding | 4 | 872 | ttctggctgtagcgggtcct | 54 | 52 |
| 299913 | Coding | 4 | 879 | gccaattttctggctgtagc | 61 | 53 |
| 299914 | Coding | 4 | 889 | tgaggtcgtcgccaattttc | 56 | 54 |
| 299915 | Coding | 4 | 898 | tgctgacactgaggtcgtcg | 63 | 55 |
| 299916 | Coding | 4 | 904 | gccaggtgctgacactgagg | 67 | 56 |
| 299917 | Coding | 4 | 966 | cacgatgccatattgcatga | 59 | 57 |
| 299918 | Coding | 4 | 1028 | gtggccaggcccagcaggtt | 52 | 58 |
| 299919 | Coding | 4 | 1122 | cagacacttgaccactgccc | 40 | 59 |
| 299920 | Coding | 4 | 1182 | ccgcaggatccaccagaagc | 46 | 60 |
| 299921 | Coding | 4 | 1210 | tgatcaggatggccaggaag | 42 | 61 |
| 299922 | Coding | 4 | 1228 | ggacgaagatgaagaagttg | 44 | 62 |
| 299923 | Coding | 4 | 1259 | cgcagcttggccacgagcag | 8 | 63 |
| 299924 | Coding | 4 | 1274 | tgcatctgccgtgcccgcag | 58 | 64 |
| 299925 | Coding | 4 | 1291 | acttgtagtctgtgtggtgc | 34 | 65 |
| 299926 | Coding | 4 | 1415 | aggtcgaagaagagcttggc | 38 | 66 |
| 299927 | Coding | 4 | 1528 | gcactttgcccaggcgccag | 78 | 67 |
| 299928 | Coding | 4 | 1539 | ctcctcccatagcactttgc | 40 | 68 |
| 299929 | Coding | 4 | 1608 | aaactgcagctccttgctgg | 46 | 69 |
| 299930 | Coding | 4 | 1636 | atgaatcctggctgccacca | 70 | 70 |
| 299931 | Coding | 4 | 1670 | ctagggaggccaccagccaa | 49 | 71 |
| 299932 | Coding | 4 | 1681 | tctcagccaatctagggagg | 63 | 72 |
| 299933 | Stop Codon | 4 | 1704 | tcccagcagggttcagaagg | 30 | 73 |
| 299934 | 5'UTR | 19 | 1747 | ttcctgcaggtgacccaatg | 50 | 74 |
| 299935 | 3'UTR | 4 | 1841 | tctcgcagacagccacactg | 43 | 75 |
| 299936 | 3'UTR | 4 | 1854 | agaggaggcccaatctcgca | 79 | 76 |
| 299937 | 3'UTR | 4 | 1881 | tgcaccagggacaaggcagg | 0 | 77 |

TABLE 1-continued

Inhibition of human glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 299938 | 3'UTR | 4 | 1901 | tggactcctctgctcacctc | 58 | 78 |
| 299939 | 3'UTR | 4 | 1938 | tggcacgcagttcacggcac | 54 | 79 |
| 299940 | 3'UTR | 4 | 1969 | acatgggacgtgccgacata | 63 | 80 |
| 299941 | 3'UTR | 4 | 1978 | tttccatgcacatgggacgt | 63 | 81 |
| 299942 | 3'UTR | 4 | 1989 | gttggaggacatttccatgc | 79 | 82 |
| 299943 | 3'UTR | 4 | 2015 | cacggtgaccacttgagctc | 18 | 83 |
| 299944 | intron | 18 | 11002 | agatgtccgtgtttgtcagc | 9 | 84 |
| 299945 | intron | 18 | 11557 | taataactttttaaagaagg | 17 | 85 |
| 299946 | intron | 18 | 12295 | tactacgttgctcgggctgg | 23 | 86 |
| 299947 | intron | 18 | 14121 | agctctgtggctcagttacc | 74 | 87 |
| 299948 | intron: exon junction | 18 | 15467 | gtgcagcttgctgtggcaca | 47 | 88 |
| 299949 | intron | 18 | 16094 | cagcaaccgcttggtacagg | 100 | 89 |
| 299950 | intron: exon junction | 18 | 17017 | agaagttgatctgtgtgaga | 29 | 90 |
| 299951 | intron: exon junction | 18 | 17456 | ccagcaggccctggagagac | 53 | 91 |
| 304471 | 5'UTR | 4 | 100 | cctttgagcctcagggcccg | 42 | 92 |
| 304472 | 5'UTR | 4 | 103 | gcccctttgagcctcagggc | 25 | 93 |
| 304473 | 5'UTR | 4 | 167 | agctgagtggcagagcagca | 76 | 94 |
| 304474 | 5'UTR | 4 | 169 | gcagctgagtggcagagcag | 75 | 95 |
| 304475 | 5'UTR | 4 | 190 | tgtgtgtacgctcctccgag | 73 | 96 |
| 304476 | 5'UTR | 4 | 194 | ggtgtgtgtgtacgctcctc | 72 | 97 |
| 304477 | 5'UTR | 4 | 196 | ctggtgtgtgtgtacgctcc | 71 | 98 |
| 304478 | 5'UTR | 4 | 209 | gggcaatgcagtcctggtgt | 65 | 99 |
| 304479 | 5'UTR | 4 | 246 | ctagctgcctcccacatctg | 54 | 100 |
| 304480 | 5'UTR | 4 | 249 | cagctagctgcctcccacat | 85 | 101 |
| 304481 | 5'UTR | 4 | 257 | cctctgggcagctagctgcc | 44 | 102 |
| 304482 | Start Codon | 4 | 262 | gcatgcctctgggcagctag | 62 | 103 |
| 304483 | Coding | 4 | 325 | cctgtggctggcaggccagc | 68 | 104 |
| 304484 | Coding | 4 | 368 | ttccacttctcaaacaggaa | 24 | 105 |
| 304485 | Coding | 4 | 370 | gcttccacttctcaaacagg | 49 | 106 |
| 304486 | Coding | 4 | 375 | gtagagcttccacttctcaa | 41 | 107 |
| 304487 | Coding | 4 | 376 | cgtagagcttccacttctca | 38 | 108 |
| 304488 | Coding | 4 | 395 | ttgtggtgacactggtcacc | 24 | 109 |

TABLE 1-continued

Inhibition of human glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 304489 | Coding | 4 | 407 | agcaggctcaggttgtggtg | 52 | 110 |
| 304490 | Coding | 4 | 534 | ttgcactttgtggtgccaag | 61 | 111 |
| 304491 | Coding | 4 | 535 | gttgcactttgtggtgccaa | 57 | 112 |
| 304492 | Coding | 4 | 536 | tgttgcactttgtggtgcca | 67 | 113 |
| 304493 | Coding | 4 | 537 | gtgttgcactttgtggtgcc | 75 | 114 |
| 304494 | Coding | 4 | 563 | ggcccgcatctcttgaacac | 87 | 115 |
| 304495 | Coding | 4 | 567 | gtcgggcccgcatctcttga | 81 | 116 |
| 304496 | Coding | 4 | 617 | tgggaggcatcacgccaagg | 60 | 117 |
| 304497 | Coding | 4 | 627 | catctggcactgggaggcat | 48 | 118 |
| 304498 | Coding | 4 | 666 | cttggccacctccttctgga | 74 | 119 |
| 304499 | Coding | 4 | 671 | tacatcttggccacctcctt | 24 | 120 |
| 304500 | Coding | 4 | 685 | cctggaagctgctgtacatc | 71 | 121 |
| 304501 | Coding | 4 | 795 | attcgcgtggatggcattgc | 53 | 122 |
| 304502 | Coding | 4 | 848 | agcccatcaatgaccagcac | 31 | 123 |
| 304503 | Coding | 4 | 861 | gcgggtcctgagcagcccat | 42 | 124 |
| 304504 | Coding | 4 | 886 | ggtcgtcgccaattttctgg | 50 | 125 |
| 304505 | Coding | 4 | 893 | acactgaggtcgtcgccaat | 22 | 126 |
| 304506 | Coding | 4 | 900 | ggtgctgacactgaggtcgt | 60 | 127 |
| 304507 | Coding | 4 | 962 | atgccatattgcatgaacac | 27 | 128 |
| 304508 | Coding | 4 | 1032 | gagggtggccaggcccagca | 56 | 129 |
| 304509 | Coding | 4 | 1124 | aacagacacttgaccactgc | 13 | 130 |
| 304510 | Coding | 4 | 1125 | gaacagacacttgaccactg | 8 | 131 |
| 304511 | Coding | 4 | 1158 | gttgtcattgctggtccagc | 65 | 132 |
| 304512 | Coding | 4 | 1168 | agaagcccatgttgtcattg | 44 | 133 |
| 304513 | Coding | 4 | 1187 | gggaaccgcaggatccacca | 42 | 134 |
| 304514 | Coding | 4 | 1230 | gcggacgaagatgaagaagt | 54 | 135 |
| 304515 | Coding | 4 | 1638 | agatgaatcctggctgccac | 53 | 136 |
| 304516 | 3'UTR | 4 | 1727 | ccagagtccagccctagctg | 41 | 137 |
| 304517 | 3'UTR | 4 | 1732 | gggtgccagagtccagccct | 48 | 138 |
| 304518 | 3'UTR | 4 | 1735 | tctgggtgccagagtccagc | 65 | 139 |
| 304519 | 3'UTR | 4 | 1736 | ctctgggtgccagagtccag | 75 | 140 |
| 304520 | 3'UTR | 4 | 1737 | cctctgggtgccagagtcca | 74 | 141 |
| 304521 | 3'UTR | 4 | 1740 | acgcctctgggtgccagagt | 55 | 142 |
| 304522 | 3'UTR | 4 | 1760 | cagttctgggttgtccagcg | 52 | 143 |
| 304523 | 3'UTR | 4 | 1849 | aggcccaatctcgcagacag | 74 | 144 |
| 304524 | 3'UTR | 4 | 1850 | gaggcccaatctcgcagaca | 80 | 145 |

TABLE 1-continued

Inhibition of human glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 304525 | 3'UTR | 4 | 1856 | ggagaggaggcccaatctcg | 66 | 146 |
| 304526 | 3'UTR | 4 | 1861 | tgcagggagaggaggcccaa | 63 | 147 |
| 304527 | 3'UTR | 4 | 1883 | tctgcaccagggacaaggca | 50 | 148 |
| 304528 | 3'UTR | 4 | 1891 | tgctcacctctgcaccaggg | 66 | 149 |
| 304529 | 3'UTR | 4 | 1893 | tctgctcacctctgcaccag | 32 | 150 |
| 304530 | 3'UTR | 4 | 1899 | gactcctctgctcacctctg | 31 | 151 |
| 304531 | 3'UTR | 4 | 1905 | gccctggactcctctgctca | 69 | 152 |
| 304532 | 3'UTR | 4 | 1932 | gcagttcacggcacagcccc | 53 | 153 |
| 304533 | 3'UTR | 4 | 1933 | cgcagttcacggcacagccc | 30 | 154 |
| 304534 | 3'UTR | 4 | 1945 | gggacactggcacgcagttc | 61 | 155 |
| 304535 | 3'UTR | 4 | 1971 | gcacatgggacgtgccgaca | 83 | 156 |
| 304536 | 3'UTR | 4 | 1984 | aggacatttccatgcacatg | 61 | 157 |
| 304537 | 3'UTR | 4 | 1986 | ggaggacatttccatgcaca | 69 | 158 |
| 304538 | 3'UTR | 4 | 1999 | gctctttattgttggaggac | 66 | 159 |
| 304539 | 3'UTR | 4 | 2001 | gagctctttattgttggagg | 68 | 160 |
| 304540 | 3'UTR | 4 | 2008 | accacttgagctctttattg | 40 | 161 |
| 304541 | intron | 18 | 3174 | ggcagttttggcgtccccag | 67 | 162 |
| 304542 | intron | 18 | 6670 | gagcttcctgcctcttcacg | 39 | 163 |
| 304543 | intron | 18 | 7544 | ggataggatgtgcgtgtcta | 42 | 164 |
| 304544 | intron | 18 | 7975 | ctctctgcctccgatttctt | 12 | 165 |
| 304545 | intron: exon junction | 18 | 14888 | acaccagctctgcagggtag | 75 | 166 |
| 304546 | intron: exon junction | 18 | 15285 | cacctccttctgcgagttac | 33 | 167 |
| 310441 | Start Codon | 4 | 258 | gcctctgggcagctagctgc | 64 | 168 |
| 310442 | Coding | 4 | 317 | tggcaggccagcagcagcag | 87 | 169 |
| 310443 | Coding | 4 | 321 | tggctggcaggccagcagca | 88 | 170 |
| 310444 | Coding | 4 | 347 | tccatcacctgagcggaggg | 55 | 171 |
| 310445 | Coding | 4 | 351 | gaagtccatcacctgagcgg | 36 | 172 |
| 310446 | Coding | 4 | 355 | acaggaagtccatcacctga | 28 | 173 |
| 310447 | Coding | 4 | 365 | cacttctcaaacaggaagtc | 59 | 174 |
| 310448 | Coding | 4 | 389 | tgacactggtcaccgtagag | 18 | 175 |
| 310449 | Coding | 4 | 393 | gtggtgacactggtcaccgt | 12 | 176 |
| 310450 | Coding | 4 | 397 | ggttgtggtgacactggtca | 72 | 177 |
| 310451 | Coding | 4 | 403 | ggctcaggttgtggtgacac | 62 | 178 |
| 310452 | Coding | 4 | 452 | tacttgtcgaaggttctgtt | 44 | 179 |

TABLE 1-continued

Inhibition of human glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 310453 | Coding | 4 | 458 | caggaatacttgtcgaaggt | 40 | 180 |
| 310454 | Coding | 4 | 493 | tgttggccgtggtattggcg | 90 | 181 |
| 310455 | Coding | 4 | 497 | gagatgttggccgtggtatt | 87 | 182 |
| 310456 | Coding | 4 | 500 | caggagatgttggccgtggt | 95 | 183 |
| 310457 | Coding | 4 | 532 | gcactttgtggtgccaaggc | 96 | 184 |
| 310458 | Coding | 4 | 540 | gcggtgttgcactttgtggt | 92 | 185 |
| 310459 | Coding | 4 | 544 | cgaagcggtgttgcactttg | 50 | 186 |
| 310460 | Coding | 4 | 548 | aacacgaagcggtgttgcac | 87 | 187 |
| 310461 | Coding | 4 | 556 | atctcttgaacacgaagcgg | 65 | 188 |
| 310463 | Coding | 4 | 588 | gggtccacgcacccactgac | 50 | 189 |
| 310464 | Coding | 4 | 606 | acgccaaggctgcccccggg | 71 | 190 |
| 310465 | Coding | 4 | 660 | cacctccttctggacctcaa | 31 | 191 |
| 310466 | Coding | 4 | 683 | tggaagctgctgtacatctt | 57 | 192 |
| 310467 | Coding | 4 | 687 | cacctggaagctgctgtaca | 60 | 193 |
| 310468 | Coding | 4 | 691 | acatcacctggaagctgctg | 73 | 194 |
| 310469 | Coding | 4 | 695 | gtgtacatcacctggaagct | 79 | 195 |
| 310470 | Coding | 4 | 720 | ccccagggacaggctgtagc | 86 | 196 |
| 310471 | Coding | 4 | 723 | ggcccccagggacaggctgt | 62 | 197 |
| 310472 | Coding | 4 | 860 | cgggtcctgagcagcccatc | 48 | 198 |
| 310473 | Coding | 4 | 864 | gtagcgggtcctgagcagcc | 58 | 199 |
| 310474 | Coding | 4 | 868 | ggctgtagcgggtcctgagc | 48 | 200 |
| 310475 | Coding | 4 | 919 | ccgctccatcactgagccag | 52 | 201 |
| 310476 | Coding | 4 | 923 | gccaccgctccatcactgag | 41 | 202 |
| 310477 | Coding | 4 | 951 | catgaacaccgcggccacac | 63 | 203 |
| 310478 | Coding | 4 | 955 | attgcatgaacaccgcggcc | 76 | 204 |
| 310479 | Coding | 4 | 960 | gccatattgcatgaacaccg | 66 | 205 |
| 310480 | Coding | 4 | 1019 | cccagcaggttgtgcaggta | 58 | 206 |
| 310481 | Coding | 4 | 1025 | gccaggcccagcaggttgtg | 72 | 207 |
| 310482 | Coding | 4 | 1029 | ggtggccaggcccagcaggt | 83 | 208 |
| 310483 | Coding | 4 | 1055 | aggctgaagaagctcctctc | 71 | 209 |
| 310484 | Coding | 4 | 1059 | gtagaggctgaagaagctcc | 46 | 210 |
| 310485 | Coding | 4 | 1063 | ccaggtagaggctgaagaag | 25 | 211 |
| 310486 | Coding | 4 | 1068 | gatgcccaggtagaggctga | 51 | 212 |
| 310487 | Coding | 4 | 1072 | agccgatgcccaggtagagg | 70 | 213 |
| 310488 | Coding | 4 | 1156 | tgtcattgctggtccagcac | 83 | 214 |
| 310489 | Coding | 4 | 1160 | atgttgtcattgctggtcca | 53 | 215 |

TABLE 1-continued

Inhibition of human glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 310490 | Coding | 4 | 1167 | gaagcccatgttgtcattgc | 45 | 216 |
| 310491 | Coding | 4 | 1173 | ccaccagaagcccatgttgt | 50 | 217 |
| 310492 | Coding | 4 | 1176 | gatccaccagaagcccatgt | 53 | 218 |
| 310493 | Coding | 4 | 1185 | gaaccgcaggatccaccaga | 47 | 219 |
| 310494 | Coding | 4 | 1206 | caggatggccaggaagacgg | 39 | 220 |
| 310495 | Coding | 4 | 1209 | gatcaggatggccaggaaga | 67 | 221 |
| 310496 | Coding | 4 | 1219 | tgaagaagttgatcaggatg | 10 | 222 |
| 310497 | Coding | 4 | 1222 | agatgaagaagttgatcagg | 20 | 223 |
| 310498 | Coding | 4 | 1287 | gtagtctgtgtggtgcatct | 35 | 224 |
| 310499 | Coding | 4 | 1290 | cttgtagtctgtgtggtgca | 63 | 225 |
| 310500 | Coding | 4 | 1293 | gaacttgtagtctgtgtggt | 27 | 226 |
| 310501 | Coding | 4 | 1414 | ggtcgaagaagagcttggcg | 46 | 227 |
| 310502 | Coding | 4 | 1417 | agaggtcgaagaagagcttg | 26 | 228 |
| 310503 | Coding | 4 | 1423 | tgaggaagaggtcgaagaag | 17 | 229 |
| 310504 | Coding | 4 | 1669 | tagggaggccaccagccaag | 53 | 230 |
| 315163 | Coding | 4 | 686 | acctggaagctgctgtacat | 75 | 231 |
| 315164 | Coding | 4 | 409 | gcagcaggctcaggttgtgg | 24 | 232 |
| 315165 | Coding | 4 | 1424 | ctgaggaagaggtcgaagaa | 42 | 233 |
| 315166 | Coding | 4 | 398 | aggttgtggtgacactggtc | 34 | 234 |
| 315167 | Coding | 4 | 1212 | gttgatcaggatggccagga | 47 | 235 |
| 315168 | Coding | 4 | 1062 | caggtagaggctgaagaagc | 40 | 236 |
| 315169 | Coding | 4 | 559 | cgcatctcttgaacacgaag | 48 | 237 |
| 315170 | Coding | 4 | 543 | gaagcggtgttgcactttgt | 61 | 238 |
| 315171 | Coding | 4 | 454 | aatacttgtcgaaggttctg | 16 | 239 |
| 315172 | Coding | 4 | 1026 | ggccaggcccagcaggttgt | 72 | 240 |
| 315173 | Coding | 4 | 1070 | ccgatgcccaggtagaggct | 59 | 241 |
| 315174 | Coding | 4 | 496 | agatgttggccgtggtattg | 79 | 242 |
| 315175 | Coding | 4 | 399 | caggttgtggtgacactggt | 58 | 243 |
| 315176 | Coding | 4 | 1420 | ggaagaggtcgaagaagagc | 26 | 244 |
| 315177 | Coding | 4 | 392 | tggtgacactggtcaccgta | 49 | 245 |
| 315178 | Coding | 4 | 402 | gctcaggttgtggtgacact | 62 | 246 |
| 315179 | Coding | 4 | 533 | tgcactttgtggtgccaagg | 75 | 247 |
| 315180 | Coding | 4 | 689 | atcacctggaagctgctgta | 45 | 248 |
| 315181 | Coding | 4 | 956 | tattgcatgaacaccgcggc | 78 | 249 |
| 315182 | Coding | 4 | 1208 | atcaggatggccaggaagac | 36 | 250 |
| 315183 | Coding | 4 | 555 | tctcttgaacacgaagcggt | 71 | 251 |

TABLE 1-continued

Inhibition of human glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 315184 | Coding | 4 | 553 | tcttgaacacgaagcggtgt | 87 | 252 |
| 315185 | Coding | 4 | 1027 | tggccaggcccagcaggttg | 61 | 253 |
| 315186 | Coding | 4 | 871 | tctggctgtagcgggtcctg | 73 | 254 |
| 315187 | Coding | 4 | 498 | ggagatgttggccgtggtat | 93 | 255 |
| 315188 | Start Codon | 4 | 259 | tgcctctgggcagctagctg | 70 | 256 |
| 315189 | Coding | 4 | 1058 | tagaggctgaagaagctcct | 54 | 257 |
| 315190 | Coding | 4 | 348 | gtccatcacctgagcggagg | 68 | 258 |
| 315191 | Coding | 4 | 1292 | aacttgtagtctgtgtggtg | 39 | 259 |
| 315192 | Stop Codon | 4 | 1705 | gtcccagcagggttcagaag | 31 | 260 |
| 315193 | Coding | 4 | 953 | tgcatgaacaccgcggccac | 73 | 261 |
| 315194 | Coding | 4 | 1024 | ccaggcccagcaggttgtgc | 73 | 262 |
| 315195 | Coding | 4 | 1061 | aggtagaggctgaagaagct | 57 | 263 |
| 315196 | Coding | 4 | 1169 | cagaagcccatgttgtcatt | 47 | 264 |
| 315197 | Coding | 4 | 1161 | catgttgtcattgctggtcc | 0 | 265 |
| 315198 | Coding | 4 | 1021 | ggcccagcaggttgtgcagg | 84 | 266 |
| 315199 | Coding | 4 | 400 | tcaggttgtggtgacactgg | 42 | 267 |
| 315200 | Coding | 4 | 1165 | agcccatgttgtcattgctg | 45 | 268 |
| 315201 | Coding | 4 | 363 | cttctcaaacaggaagtcca | 47 | 269 |
| 315202 | Coding | 4 | 550 | tgaacacgaagcggtgttgc | 83 | 270 |
| 315203 | Coding | 4 | 367 | tccacttctcaaacaggaag | 69 | 271 |
| 315204 | Coding | 4 | 353 | aggaagtccatcacctgagc | 26 | 272 |
| 315205 | Coding | 4 | 1071 | gccgatgcccaggtagaggc | 82 | 273 |
| 315206 | Coding | 4 | 1186 | ggaaccgcaggatccaccag | 36 | 274 |
| 315207 | Coding | 4 | 349 | agtccatcacctgagcggag | 63 | 275 |
| 315208 | Coding | 4 | 1221 | gatgaagaagttgatcagga | 28 | 276 |
| 315209 | Coding | 4 | 461 | cagcaggaatacttgtcgaa | 27 | 277 |
| 315210 | Coding | 4 | 463 | gccagcaggaatacttgtcg | 41 | 278 |
| 315211 | Coding | 4 | 320 | ggctggcaggccagcagcag | 72 | 279 |
| 315212 | Coding | 4 | 1183 | accgcaggatccaccagaag | 59 | 280 |
| 315213 | Coding | 4 | 862 | agcgggtcctgagcagccca | 68 | 281 |
| 315214 | Coding | 4 | 565 | cgggcccgcatctcttgaac | 88 | 282 |
| 315215 | Coding | 4 | 1295 | cggaacttgtagtctgtgtg | 29 | 283 |
| 315216 | Coding | 4 | 1177 | ggatccaccagaagcccatg | 58 | 284 |
| 315217 | Stop Codon | 4 | 1706 | ggtcccagcagggttcagaa | 34 | 285 |

TABLE 1-continued

Inhibition of human glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 315218 | Coding | 4 | 1184 | aaccgcaggatccaccagaa | 55 | 286 |
| 315219 | Coding | 4 | 410 | ggcagcaggctcaggttgtg | 50 | 287 |
| 315220 | Coding | 4 | 495 | gatgttggccgtggtattgg | 86 | 288 |
| 315221 | Coding | 4 | 455 | gaatacttgtcgaaggttct | 37 | 289 |
| 315222 | Coding | 4 | 1215 | gaagttgatcaggatggcca | 39 | 290 |
| 315223 | Coding | 4 | 688 | tcacctggaagctgctgtac | 48 | 291 |
| 315224 | Coding | 4 | 959 | ccatattgcatgaacaccgc | 20 | 292 |
| 315225 | Coding | 4 | 863 | tagcgggtcctgagcagccc | 61 | 293 |
| 315226 | 5'UTR | 4 | 256 | ctctgggcagctagctgcct | 28 | 294 |
| 315227 | Coding | 4 | 359 | tcaaacaggaagtccatcac | 17 | 295 |
| 315228 | Coding | 4 | 1172 | caccagaagcccatgttgtc | 15 | 296 |
| 315229 | Coding | 4 | 694 | tgtacatcacctggaagctg | 67 | 297 |
| 315230 | Coding | 4 | 494 | atgttggccgtggtattggc | 52 | 298 |
| 315231 | Coding | 4 | 1069 | cgatgcccaggtagaggctg | 7 | 299 |
| 315232 | Coding | 4 | 1178 | aggatccaccagaagcccat | 83 | 300 |
| 315233 | Coding | 4 | 1207 | tcaggatggccaggaagacg | 52 | 301 |
| 315234 | Coding | 4 | 352 | ggaagtccatcacctgagcg | 60 | 302 |
| 315235 | Start Codon | 4 | 261 | catgcctctgggcagctagc | 65 | 303 |
| 315236 | Coding | 4 | 561 | cccgcatctcttgaacacga | 51 | 304 |
| 315237 | Coding | 4 | 323 | tgtggctggcaggccagcag | 60 | 305 |
| 315238 | Coding | 4 | 324 | ctgtggctggcaggccagca | 43 | 306 |
| 315239 | Coding | 4 | 1179 | caggatccaccagaagccca | 88 | 307 |
| 315240 | Coding | 4 | 1223 | aagatgaagaagttgatcag | 0 | 308 |
| 315241 | Coding | 4 | 1289 | ttgtagtctgtgtggtgcat | 66 | 309 |
| 315242 | Coding | 4 | 322 | gtggctggcaggccagcagc | 47 | 310 |
| 315243 | Coding | 4 | 406 | gcaggctcaggttgtggtga | 44 | 311 |
| 315244 | Coding | 4 | 870 | ctggctgtagcgggtcctga | 61 | 312 |
| 315245 | 5'UTR | 4 | 255 | tctgggcagctagctgcctc | 24 | 313 |
| 315246 | Coding | 4 | 464 | ggccagcaggaatacttgtc | 71 | 314 |
| 315247 | Coding | 4 | 360 | ctcaaacaggaagtccatca | 13 | 315 |
| 315248 | Coding | 4 | 1060 | ggtagaggctgaagaagctc | 49 | 316 |
| 315249 | Coding | 4 | 1422 | gaggaagaggtcgaagaaga | 69 | 317 |
| 315250 | Coding | 4 | 1416 | gaggtcgaagaagagcttgg | 32 | 318 |
| 315251 | Coding | 4 | 1288 | tgtagtctgtgtggtgcatc | 30 | 319 |
| 315252 | Coding | 4 | 1216 | agaagttgatcaggatggcc | 17 | 320 |
| 315253 | Coding | 4 | 542 | aagcggtgttgcactttgtg | 55 | 321 |

TABLE 1-continued

Inhibition of human glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 315254 | Coding | 4 | 456 | ggaatacttgtcgaaggttc | 44 | 322 |
| 315255 | Coding | 4 | 1419 | gaagaggtcgaagaagagct | 34 | 323 |
| 315256 | Coding | 4 | 460 | agcaggaatacttgtcgaag | 10 | 324 |
| 315257 | Coding | 4 | 404 | aggctcaggttgtggtgaca | 58 | 325 |
| 315258 | Coding | 4 | 538 | ggtgttgcactttgtggtgc | 58 | 326 |
| 315259 | Coding | 4 | 1294 | ggaacttgtagtctgtgtgg | 30 | 327 |
| 315260 | Coding | 4 | 390 | gtgacactggtcaccgtaga | 19 | 328 |
| 315261 | Coding | 4 | 954 | ttgcatgaacaccgcggcca | 59 | 329 |
| 315262 | Coding | 4 | 684 | ctggaagctgctgtacatct | 61 | 330 |
| 315263 | Coding | 4 | 1174 | tccaccagaagcccatgttg | 1 | 331 |
| 315264 | Coding | 4 | 1214 | aagttgatcaggatggccag | 44 | 332 |
| 315265 | Coding | 4 | 1023 | caggcccagcaggttgtgca | 51 | 333 |
| 315266 | Coding | 4 | 920 | accgctccatcactgagcca | 38 | 334 |
| 315267 | Coding | 4 | 1220 | atgaagaagttgatcaggat | 0 | 335 |
| 315268 | Coding | 4 | 554 | ctcttgaacacgaagcggtg | 78 | 336 |
| 315269 | Coding | 4 | 318 | ctggcaggccagcagcagca | 37 | 337 |
| 315270 | Coding | 4 | 499 | aggagatgttggccgtggta | 97 | 338 |
| 315271 | Coding | 4 | 1164 | gcccatgttgtcattgctgg | 66 | 339 |
| 315272 | Coding | 4 | 1217 | aagaagttgatcaggatggc | 25 | 340 |
| 315273 | Coding | 4 | 1064 | cccaggtagaggctgaagaa | 62 | 341 |
| 315274 | Coding | 4 | 1163 | cccatgttgtcattgctggt | 55 | 342 |
| 315275 | Coding | 4 | 547 | acacgaagcggtgttgcact | 46 | 343 |
| 315276 | Coding | 4 | 408 | cagcaggctcaggttgtggt | 62 | 344 |
| 315277 | Coding | 4 | 394 | tgtggtgacactggtcaccg | 15 | 345 |
| 315278 | Coding | 4 | 1020 | gcccagcaggttgtgcaggt | 83 | 346 |
| 315279 | Coding | 4 | 869 | tggctgtagcgggtcctgag | 33 | 347 |
| 315280 | Coding | 4 | 562 | gcccgcatctcttgaacacg | 77 | 348 |
| 315281 | Coding | 4 | 1418 | aagaggtcgaagaagagctt | 40 | 349 |
| 315282 | Coding | 4 | 411 | gggcagcaggctcaggttgt | 23 | 350 |
| 315283 | Coding | 4 | 557 | catctcttgaacacgaagcg | 40 | 351 |
| 315284 | Coding | 4 | 1175 | atccaccagaagcccatgtt | 38 | 352 |
| 315285 | Coding | 4 | 1155 | gtcattgctggtccagcact | 75 | 353 |
| 315286 | Coding | 4 | 566 | tcgggcccgcatctcttgaa | 74 | 354 |
| 315287 | Coding | 4 | 721 | cccccagggacaggctgtag | 53 | 355 |
| 315288 | Coding | 4 | 1162 | ccatgttgtcattgctggtc | 43 | 356 |
| 315289 | Coding | 4 | 1056 | gaggctgaagaagctcctct | 2 | 357 |

TABLE 1-continued

Inhibition of human glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 315290 | Coding | 4 | 549 | gaacacgaagcggtgttgca | 88 | 358 |
| 315291 | Coding | 4 | 362 | ttctcaaacaggaagtccat | 9 | 359 |
| 315292 | Coding | 4 | 1159 | tgttgtcattgctggtccag | 47 | 360 |
| 315293 | Coding | 4 | 457 | aggaatacttgtcgaaggtt | 55 | 361 |
| 315294 | Coding | 4 | 405 | caggctcaggttgtggtgac | 38 | 362 |
| 315295 | Coding | 4 | 1421 | aggaagaggtcgaagaagag | 19 | 363 |
| 315296 | Coding | 4 | 1425 | gctgaggaagaggtcgaaga | 33 | 364 |
| 315297 | Coding | 4 | 546 | cacgaagcggtgttgcactt | 81 | 365 |
| 315298 | Coding | 4 | 1166 | aagcccatgttgtcattgct | 35 | 366 |
| 315299 | Start Codon | 4 | 260 | atgcctctgggcagctagct | 63 | 367 |
| 315300 | Coding | 4 | 690 | catcacctggaagctgctgt | 63 | 368 |
| 315301 | Coding | 4 | 364 | acttctcaaacaggaagtcc | 31 | 369 |
| 315302 | Coding | 4 | 558 | gcatctcttgaacacgaagc | 44 | 370 |
| 315303 | Coding | 4 | 958 | catattgcatgaacaccgcg | 48 | 371 |
| 315304 | Coding | 4 | 1170 | ccagaagcccatgttgtcat | 33 | 372 |
| 315305 | Coding | 4 | 867 | gctgtagcgggtcctgagca | 50 | 373 |
| 315306 | Coding | 4 | 865 | tgtagcgggtcctgagcagc | 62 | 374 |
| 315307 | Coding | 4 | 1022 | aggcccagcaggttgtgcag | 37 | 375 |
| 315308 | Coding | 4 | 692 | tacatcacctggaagctgct | 41 | 376 |
| 315309 | Coding | 4 | 1181 | cgcaggatccaccagaagcc | 49 | 377 |
| 315310 | Coding | 4 | 357 | aaacaggaagtccatcacct | 21 | 378 |
| 315311 | Coding | 4 | 1057 | agaggctgaagaagctcctc | 49 | 379 |
| 315312 | Coding | 4 | 1211 | ttgatcaggatggccaggaa | 54 | 380 |
| 315313 | Coding | 4 | 541 | agcggtgttgcactttgtgg | 81 | 381 |
| 315314 | Coding | 4 | 319 | gctggcaggccagcagcagc | 75 | 382 |
| 315315 | Coding | 4 | 545 | acgaagcggtgttgcacttt | 68 | 383 |
| 315316 | Coding | 4 | 952 | gcatgaacaccgcggccaca | 80 | 384 |
| 315317 | Coding | 4 | 354 | caggaagtccatcacctgag | 26 | 385 |
| 315318 | Coding | 4 | 1180 | gcaggatccaccagaagccc | 72 | 386 |
| 315319 | Coding | 4 | 1213 | agttgatcaggatggccagg | 33 | 387 |
| 315320 | Coding | 4 | 722 | gcccccagggacaggctgta | 51 | 388 |
| 315321 | Coding | 4 | 356 | aacaggaagtccatcacctg | 0 | 389 |
| 315322 | Coding | 4 | 957 | atattgcatgaacaccgcgg | 56 | 390 |
| 315323 | Coding | 4 | 459 | gcaggaatacttgtcgaagg | 59 | 391 |
| 315324 | Coding | 4 | 693 | gtacatcacctggaagctgc | 79 | 392 |

TABLE 1-continued

Inhibition of human glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 315325 | Coding | 4 | 1153 | cattgctggtccagcactgg | 61 | 393 |
| 315326 | Coding | 4 | 358 | caaacaggaagtccatcacc | 10 | 394 |
| 315327 | Coding | 4 | 1031 | agggtggccaggcccagcag | 27 | 395 |
| 315328 | Coding | 4 | 551 | ttgaacacgaagcggtgttg | 66 | 396 |
| 315329 | Coding | 4 | 1171 | accagaagcccatgttgtca | 47 | 397 |
| 315330 | Coding | 4 | 401 | ctcaggttgtggtgacactg | 14 | 398 |
| 315331 | Coding | 4 | 396 | gttgtggtgacactggtcac | 5 | 399 |

As shown in Table 1, SEQ ID NOs 20, 21, 22, 24, 25, 28, 29, 30, 35, 37, 39, 40, 41, 42, 43, 44, 46, 48, 49, 50, 51, 52, 53, 54, 55, 56, 57, 58, 59, 60, 61, 62, 64, 67, 68, 69, 70, 71, 72, 74, 75, 76, 78, 79, 80, 81, 82, 87, 88, 89, 91, 92, 94, 95, 96, 97, 98, 99, 100, 101, 102, 103, 104, 106, 107, 110, 111, 112, 113, 114, 115, 116, 117, 118, 119, 121, 122, 124, 125, 127, 129, 132, 133, 134, 135, 136, 137, 138, 139, 140, 141, 142, 143, 144, 145, 146, 147, 148, 149, 152, 153, 145, 156, 157, 158, 159, 160, 161, 162, 164, 166, 168, 169, 170, 171, 174, 177, 178, 179, 180, 181, 182, 183, 184, 185, 186, 187, 188, 189, 190, 192, 193, 194, 195, 196, 197, 198, 199, 200, 201, 202, 203, 204, 205, 206, 207, 208, 209, 210, 212, 213, 214, 215, 216, 217, 218, 219, 221, 225, 227, 230, 231, 233, 235, 236, 237, 238, 240, 241, 242, 243, 245, 246, 247, 248, 249, 251, 252, 253, 254, 255, 256, 257, 258, 261, 262, 263, 264, 266, 267, 268, 269, 270, 271, 273, 275, 278, 279, 280, 281, 282, 284, 286, 287, 288, 291, 293, 297, 298, 300, 301, 302, 303, 304, 305, 306, 307, 309, 310, 311, 312, 314, 316, 317, 321, 322, 325, 326, 329, 330, 332, 333, 336, 338, 339, 341, 342, 343, 344, 346, 348, 349, 351, 353, 354, 355, 356, 358, 360, 361, 365, 367, 368, 370, 371, 373, 374, 376, 377, 379, 380, 381, 382, 383, 384, 386, 388, 390, 391, 392, 393, 396 and 397 demonstrated at least 40% inhibition of human glucagon receptor expression in this assay and are therefore preferred. SEQ ID NO: 183, 184, 231, 249, 254, 346, 365 and 392 are presently more preferred. The target regions to which the preferred sequences are complementary are herein referred to as "preferred target segments" and are therefore preferred for targeting by compounds of the present invention. These preferred target segments are shown in Table 3. These sequences are shown to contain thymine (T) but one of skill in the art will appreciate that thymine (T) is generally replaced by uracil (U) in RNA sequences. The sequences represent the reverse complement of the preferred antisense compounds shown in Table 1. "Target site" indicates the first (5'-most) nucleotide number on the particular target nucleic acid to which the oligonucleotide binds. Also shown in Table 3 is the species in which each of the preferred target segments was found.

Example 16

Antisense Inhibition of Mouse Glucagon Receptor Expression by Chimeric Phosphorothioate Oligonucleotides Having 2'-MOE Wings and a Deoxy Gap In accordance with the present invention, a second series of antisense compounds were designed to target different regions of the mouse glucagon receptor RNA, using published sequences (GenBank accession number NM_008101.1, incorporated herein as SEQ ID NO: 11, an mRNA sequence derived from GenBank accession number AF229079.1 with an alternate promoter, incorporated herein as SEQ ID NO: 400, GenBank accession number AF229079.1, incorporated herein as SEQ ID NO: 401, a second mRNA sequence derived from GenBank accession number AF229079.1 with an alternate promoter, incorporated herein as SEQ ID NO: 402, and GenBank accession number AA920726.1, incorporated herein as SEQ ID NO: 403). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse glucagon receptor mRNA levels by quantitative real-time PCR as described in other examples herein. Data are averages from three experiments in which mouse primary hepatocytes were treated with the antisense oligonucleotides of the present invention. The positive control for each datapoint is identified in the table by sequence ID number. If present, "N.D." indicates "no data".

TABLE 2

Inhibition of mouse glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 148350 | 5'UTR | 11 | 57 | cccacatctggcagaggttg | 30 | 404 | 1 |
| 148355 | coding | 11 | 182 | ttctcaaacaaaaagtccat | 7 | 405 | 1 |
| 148356 | coding | 11 | 193 | agagcttccacttctcaaac | 63 | 406 | 1 |
| 148357 | coding | 11 | 203 | tggtcactatagagcttcca | 39 | 407 | 1 |
| 148359 | coding | 11 | 227 | agcaggcttaggttgtggtg | 39 | 408 | 1 |
| 148363 | coding | 11 | 322 | ggcaggaaatgttggcagtg | 52 | 409 | 1 |
| 148366 | coding | 11 | 383 | ggcccacacctcttgaacac | 93 | 410 | 1 |
| 148368 | exon: exon junction | 11 | 477 | ccccttctggacctcgatct | 45 | 411 | 1 |
| 148371 | coding | 11 | 538 | ccagggacagactgtagccc | 53 | 412 | 1 |
| 148372 | exon: exon junction | 11 | 589 | agtgcagcttcctgaggccc | 52 | 413 | 1 |
| 148381 | coding | 11 | 938 | cacttgaccaccacccaggg | 47 | 414 | 1 |
| 148382 | coding | 11 | 947 | tcaaacagacacttgaccac | 0 | 415 | 1 |
| 148385 | coding | 11 | 977 | ttgtcattgctggtccagca | 57 | 416 | 1 |
| 148387 | coding | 11 | 998 | aggatccaccagaatcccat | 53 | 417 | 1 |
| 148390 | coding | 11 | 1139 | agggtcagcgtggacctggc | 45 | 418 | 1 |
| 148393 | coding | 11 | 1226 | aagagcttggtggagcgcag | 26 | 419 | 1 |
| 148394 | coding | 11 | 1277 | tagagaacagccaccagcag | 26 | 420 | 1 |
| 148395 | coding | 11 | 1285 | ggaaacagtagagaacagcc | 26 | 421 | 1 |
| 148396 | exon: exon junction | 11 | 1299 | cacctccttgttgaggaaac | 0 | 422 | 1 |
| 180446 | 5'UTR | 11 | 7 | ctcctcaggttgcaagggag | 15 | 423 | 1 |
| 180447 | 5'UTR | 11 | 14 | tgcacctctcctcaggttgc | 38 | 424 | 1 |
| 180448 | 5'UTR | 11 | 25 | ctcagagtgtgtgcacctct | 54 | 425 | 1 |
| 180449 | 5'UTR | 11 | 30 | aggtcctcagagtgtgtgca | 55 | 426 | 1 |
| 180450 | 5'UTR | 11 | 48 | ggcagaggttgcacacctag | 39 | 427 | 1 |
| 180451 | Start Codon | 11 | 80 | ggcatgcctctgggtagcca | 40 | 428 | 1 |
| 180452 | Coding | 11 | 141 | tggcagacatgacagcacca | 5 | 429 | 1 |
| 180453 | Coding | 11 | 192 | gagcttccacttctcaaaca | 37 | 430 | 1 |
| 180454 | Coding | 11 | 251 | cagaccagctcagtaggtgg | 45 | 431 | 1 |
| 180455 | Coding | 11 | 291 | ggtgtcaggccagcaggagt | 58 | 432 | 1 |
| 180456 | Coding | 11 | 359 | cggtgctgcactttgtggca | 68 | 433 | 1 |
| 180457 | Coding | 11 | 371 | ttgaacactaggcggtgctg | 69 | 434 | 1 |
| 180458 | Coding | 11 | 410 | cgtggccctcgaacccactg | 39 | 435 | 1 |
| 180459 | Coding | 11 | 545 | aaggcccccagggacagact | 56 | 436 | 1 |

TABLE 2-continued

Inhibition of mouse glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 180460 | Coding | 11 | 572 | cccagcaggatgaccagcgc | 59 | 437 | 1 |
| 180461 | Coding | 11 | 582 | cttcctgaggcccagcagga | 40 | 438 | 1 |
| 180462 | Coding | 11 | 650 | acagagccagccttgagcac | 47 | 439 | 1 |
| 180463 | Coding | 11 | 764 | actgtggccactctgcagcc | 43 | 440 | 1 |
| 180464 | Coding | 11 | 775 | actgcatgatcactgtggcc | 60 | 441 | 1 |
| 180465 | Coding | 11 | 785 | atgatgccgtactgcatgat | 58 | 442 | 1 |
| 180466 | Coding | 11 | 836 | agcaggctgtacaggtacac | 36 | 443 | 1 |
| 180467 | Coding | 11 | 974 | tcattgctggtccagcactg | 62 | 444 | 1 |
| 180468 | Coding | 11 | 1011 | gacaggaatacgcaggatcc | 0 | 445 | 1 |
| 180469 | Coding | 11 | 1079 | cgcagcttggccacaagaag | 56 | 446 | 1 |
| 180470 | Coding | 11 | 1090 | tctgatgggcacgcagcttg | 8 | 447 | 1 |
| 180471 | Coding | 11 | 1100 | gcatagtgcatctgatgggc | 45 | 448 | 1 |
| 180472 | Coding | 11 | 1110 | cttgtaatcagcatagtgca | 14 | 449 | 1 |
| 180473 | Coding | 11 | 1256 | ccctggaaggagctgaggaa | 45 | 450 | 1 |
| 180474 | Coding | 11 | 1292 | ttgttgaggaaacagtagag | 47 | 451 | 1 |
| 180475 | Coding | 11 | 1348 | gagctttgccttcttgccat | 64 | 452 | 1 |
| 180476 | Coding | 11 | 1360 | tttcctcctgaagagctttg | 56 | 453 | 1 |
| 180477 | Coding | 11 | 1388 | atgtggctgccatggctgct | 64 | 454 | 1 |
| 180478 | Coding | 11 | 1435 | gctgaagtttctcacaggga | 56 | 455 | 1 |
| 180479 | Coding | 11 | 1450 | tgcctgcactcataagctga | 48 | 456 | 1 |
| 180480 | Coding | 11 | 1470 | acagccagtcccactgctgc | 41 | 457 | 1 |
| 180481 | Coding | 11 | 1512 | ccttgggagactactggcca | 56 | 458 | 1 |
| 180482 | Stop Codon | 11 | 1544 | caagtggagattcaggtggg | 47 | 459 | 1 |
| 180483 | 3'UTR | 11 | 1567 | ttgaacacaacctgcctagg | 9 | 460 | 1 |
| 180484 | 3'UTR | 11 | 1575 | gccctttcttgaacacaacc | 34 | 461 | 1 |
| 180485 | 3'UTR | 11 | 1600 | atctggctctgggttgtcct | 59 | 462 | 1 |
| 180486 | 3'UTR | 11 | 1610 | ttggccgggcatctggctct | 53 | 463 | 1 |
| 180487 | 3'UTR | 11 | 1620 | ctcttcaaccttggccgggc | 66 | 464 | 1 |
| 180488 | 3'UTR | 11 | 1646 | tacaagctgctgtcttgctg | 54 | 465 | 1 |
| 180489 | 3'UTR | 11 | 1687 | ggcctgtgccaggctaggac | 47 | 466 | 1 |
| 180490 | 3'UTR | 11 | 1724 | gcttctccatcatatccaac | 47 | 467 | 1 |
| 180491 | 3'UTR | 11 | 1750 | aacactcagagttcatagat | 51 | 468 | 1 |
| 180492 | 3'UTR | 11 | 1756 | catgggaacactcagagttc | 49 | 469 | 1 |
| 180493 | 3'UTR | 11 | 1795 | ctgaaggacatatctgggta | 51 | 470 | 1 |
| 180494 | intron | 401 | 3953 | gtaacaaaggcgagaccaag | 36 | 471 | 1 |
| 180495 | intron | 401 | 5396 | gaggaagtgtcaccattagg | 23 | 472 | 1 |

TABLE 2-continued

Inhibition of mouse glucagon receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 180496 | intron: exon junction | 401 | 7321 | cagaccagctctgtgaaggt | 32 | 473 | 1 |
| 180497 | intron: exon junction | 401 | 7505 | cggtgctgcactgggcatgg | 77 | 474 | 1 |
| 180498 | exon: intron junction | 401 | 8075 | ctgggctcaccccgtcactg | 27 | 475 | 1 |
| 180499 | intron | 401 | 8766 | ccaaggatgggcaacctgac | 33 | 476 | 1 |
| 180500 | exon: intron junction | 401 | 9005 | ccttaccaaccggaacttgt | 2 | 477 | 1 |
| 180501 | genomic | 402 | 128 | cctctcctcaggtgtgctca | 3 | 478 | 1 |
| 180502 | genomic | 400 | 10 | ccaagcccaaggcctcatga | 40 | 479 | 1 |
| 180503 | genomic | 400 | 85 | ctcaggctgcagaggaccag | 39 | 480 | 1 |
| 180504 | genomic | 403 | 40 | taggtctcttccctccactc | 4 | 481 | 1 |

As shown in Table 2, SEQ ID NOs 404, 406, 407, 408, 409, 410, 411, 412, 413, 414, 416, 417, 418, 424, 425, 426, 427, 428, 430, 431, 432, 433, 434, 435, 436, 437, 438, 439, 440, 441, 442, 443, 444, 446, 448, 450, 451, 452, 453, 454, 455, 456, 457, 458, 459, 461, 462, 463, 464, 465, 466, 467, 468, 469, 470, 471, 473, 474, 476, 479 and 480 demonstrated at least 30% inhibition of mouse glucagon receptor expression in this experiment and are therefore preferred. The target regions to which these preferred sequences are complementary aree herein referred to as “preferred target segments” and are therefore preferred for targeting by compounds of the present invention. These preferred target segments are shown in Table 3. These sequences are shown to contain thymine (T) but one of skill in the art will appreciate that thymine (T) is generally replaced by uracil (U) in RNA sequences. The sequences represent the reverse complement of the preferred antisense compounds shown in Tables 1 and 2. “Target site” indicates the first (5'-most) nucleotide number on the paticular target nucleic acid to which the oligonucleotide binds. Also shown in Table 3 is the species in which each of the preferred target segments was found.

TABLE 3

Sequence and position of preferred target segments identified in glucagon receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 215734 | 4 | 97 | gcgcgggccctgaggctcaa | 21 | *H. sapiens* | 484 |
| 215735 | 4 | 121 | gcagcttcaggggaggacac | 22 | *H. sapiens* | 485 |
| 215737 | 4 | 192 | cggaggagcgtacacacaca | 24 | *H. sapiens* | 486 |
| 215738 | 4 | 198 | agcgtacacacacaccagga | 25 | *H. sapiens* | 487 |
| 110316 | 4 | 263 | tagctgcccagaggcatgcc | 28 | *H. sapiens* | 488 |
| 215800 | 4 | 462 | tcgacaagtattcctgctgg | 29 | *H. sapiens* | 489 |
| 215741 | 4 | 328 | ggcctgccagccacaggtcc | 30 | *H. sapiens* | 490 |
| 215746 | 4 | 391 | ctacggtgaccagtgtcacc | 35 | *H. sapiens* | 491 |
| 215748 | 4 | 442 | gctggtgtgcaacagaacct | 37 | *H. sapiens* | 492 |
| 110318 | 4 | 539 | caccacaaagtgcaacaccg | 39 | *H. sapiens* | 493 |
| 215798 | 19 | 546 | tgccgctgtctctgccaggg | 40 | *H. sapiens* | 494 |

TABLE 3-continued

Sequence and position of preferred target segments identified in glucagon receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 215750 | 4 | 552 | aacaccgcttcgtgttcaag | 41 | *H. sapiens* | 495 |
| 215751 | 4 | 564 | tgttcaagagatgcgggccc | 42 | *H. sapiens* | 496 |
| 215801 | 18 | 15279 | gccactgtaactcgcagaag | 43 | *H. sapiens* | 497 |
| 215752 | 4 | 651 | gcgaggagattgaggtccag | 44 | *H. sapiens* | 498 |
| 215754 | 4 | 663 | aggtccagaaggaggtggcc | 46 | *H. sapiens* | 499 |
| 215756 | 4 | 681 | ccaagatgtacagcagcttc | 48 | *H. sapiens* | 500 |
| 215757 | 4 | 751 | cgccttggccatcctggggg | 49 | *H. sapiens* | 501 |
| 215758 | 4 | 830 | gtgctgaaagccagctccgt | 50 | *H. sapiens* | 502 |
| 215759 | 4 | 866 | ctgctcaggacccgctacag | 51 | *H. sapiens* | 503 |
| 215760 | 4 | 872 | aggacccgctacagccagaa | 52 | *H. sapiens* | 504 |
| 215761 | 4 | 879 | gctacagccagaaaattggc | 53 | *H. sapiens* | 505 |
| 215762 | 4 | 889 | gaaaattggcgacgacctca | 54 | *H. sapiens* | 506 |
| 215763 | 4 | 898 | cgacgacctcagtgtcagca | 55 | *H. sapiens* | 507 |
| 215764 | 4 | 904 | cctcagtgtcagcacctggc | 56 | *H. sapiens* | 508 |
| 215765 | 4 | 966 | tcatgcaatatggcatcgtg | 57 | *H. sapiens* | 509 |
| 215766 | 4 | 1028 | aacctgctgggcctggccac | 58 | *H. sapiens* | 510 |
| 215767 | 4 | 1122 | gggcagtggtcaagtgtctg | 59 | *H. sapiens* | 511 |
| 215768 | 4 | 1182 | gcttctggtggatcctgcgg | 60 | *H. sapiens* | 512 |
| 215769 | 4 | 1210 | cttcctggccatcctgatca | 61 | *H. sapiens* | 513 |
| 215770 | 4 | 1228 | caacttcttcatcttcgtcc | 62 | *H. sapiens* | 514 |
| 215771 | 4 | 1274 | ctgcgggcacggcagatgca | 64 | *H. sapiens* | 515 |
| 215774 | 4 | 1528 | ctggcgcctgggcaaagtgc | 67 | *H. sapiens* | 516 |
| 215775 | 4 | 1539 | gcaaagtgctatgggaggag | 68 | *H. sapiens* | 517 |
| 215776 | 4 | 1608 | ccagcaaggagctgcagttt | 69 | *H. sapiens* | 518 |
| 215777 | 4 | 1636 | tggtggcagccaggattcat | 70 | *H. sapiens* | 519 |
| 215778 | 4 | 1670 | ttggctggtggcctccctag | 71 | *H. sapiens* | 520 |
| 215779 | 4 | 1681 | cctccctagattggctgaga | 72 | *H. sapiens* | 521 |
| 215799 | 19 | 1747 | cattgggtcacctgcaggaa | 74 | *H. sapiens* | 522 |
| 215781 | 4 | 1841 | cagtgtggctgtctgcgaga | 75 | *H. sapiens* | 523 |
| 215782 | 4 | 1854 | tgcgagattgggcctcctct | 76 | *H. sapiens* | 524 |
| 215784 | 4 | 1901 | gaggtgagcagaggagtcca | 78 | *H. sapiens* | 525 |
| 215785 | 4 | 1938 | gtgccgtgaactgcgtgcca | 79 | *H. sapiens* | 526 |
| 215786 | 4 | 1969 | tatgtcggcacgtcccatgt | 80 | *H. sapiens* | 527 |
| 215787 | 4 | 1978 | acgtcccatgtgcatggaaa | 81 | *H. sapiens* | 528 |
| 215788 | 4 | 1989 | gcatggaaatgtcctccaac | 82 | *H. sapiens* | 529 |
| 215793 | 18 | 14121 | ggtaactgagccacagagct | 87 | *H. sapiens* | 530 |

TABLE 3-continued

Sequence and position of preferred target segments identified in glucagon receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 215794 | 18 | 15467 | tgtgccacagcaagctgcac | 88 | *H. sapiens* | 531 |
| 215795 | 18 | 16094 | cctgtaccaagcggttgctg | 89 | *H. sapiens* | 532 |
| 215797 | 18 | 17456 | gtctctccagggcctgctgg | 91 | *H. sapiens* | 533 |
| 220245 | 4 | 100 | cgggccctgaggctcaaagg | 92 | *H. sapiens* | 534 |
| 220247 | 4 | 167 | tgctgctctgccactcagct | 94 | *H. sapiens* | 535 |
| 220248 | 4 | 169 | ctgctctgccactcagctgc | 95 | *H. sapiens* | 536 |
| 220249 | 4 | 190 | ctcggaggagcgtacacaca | 96 | *H. sapiens* | 537 |
| 220250 | 4 | 194 | gaggagcgtacacacacacc | 97 | *H. sapiens* | 538 |
| 220251 | 4 | 196 | ggagcgtacacacacaccag | 98 | *H. sapiens* | 539 |
| 220252 | 4 | 209 | acaccaggactgcattgccc | 99 | *H. sapiens* | 540 |
| 220253 | 4 | 246 | cagatgtgggaggcagctag | 100 | *H. sapiens* | 541 |
| 220254 | 4 | 249 | atgtgggaggcagctagctg | 101 | *H. sapiens* | 542 |
| 220255 | 4 | 257 | ggcagctagctgcccagagg | 102 | *H. sapiens* | 543 |
| 220256 | 4 | 262 | ctagctgcccagaggcatgc | 103 | *H. sapiens* | 544 |
| 220257 | 4 | 325 | gctggcctgccagccacagg | 104 | *H. sapiens* | 545 |
| 220259 | 4 | 370 | cctgtttgagaagtggaagc | 106 | *H. sapiens* | 546 |
| 220260 | 4 | 375 | ttgagaagtggaagctctac | 107 | *H. sapiens* | 547 |
| 110282 | 4 | 407 | caccacaacctgagcctgct | 110 | *H. sapiens* | 548 |
| 220263 | 4 | 534 | cttggcaccacaaagtgcaa | 111 | *H. sapiens* | 549 |
| 220264 | 4 | 535 | ttggcaccacaaagtgcaac | 112 | *H. sapiens* | 550 |
| 220265 | 4 | 536 | tggcaccacaaagtgcaaca | 113 | *H. sapiens* | 551 |
| 220266 | 4 | 537 | ggcaccacaaagtgcaacac | 114 | *H. sapiens* | 552 |
| 110289 | 4 | 563 | gtgttcaagagatgcgggcc | 115 | *H. sapiens* | 553 |
| 220267 | 4 | 567 | tcaagagatgcgggcccgac | 116 | *H. sapiens* | 554 |
| 220268 | 4 | 617 | ccttggcgtgatgcctccca | 117 | *H. sapiens* | 555 |
| 220269 | 4 | 627 | atgcctcccagtgccagatg | 118 | *H. sapiens* | 556 |
| 220270 | 4 | 666 | tccagaaggaggtggccaag | 119 | *H. sapiens* | 557 |
| 220272 | 4 | 685 | gatgtacagcagcttccagg | 121 | *H. sapiens* | 558 |
| 220273 | 4 | 795 | gcaatgccatccacgcgaat | 122 | *H. sapiens* | 559 |
| 220275 | 4 | 861 | atgggctgctcaggacccgc | 124 | *H. sapiens* | 560 |
| 220276 | 4 | 886 | ccagaaaattggcgacgacc | 125 | *H. sapiens* | 561 |
| 220277 | 4 | 900 | acgacctcagtgtcagcacc | 127 | *H. sapiens* | 562 |
| 220279 | 4 | 1032 | tgctgggcctggccaccctc | 129 | *H. sapiens* | 563 |
| 220282 | 4 | 1158 | gctggaccagcaatgacaac | 132 | *H. sapiens* | 564 |
| 220283 | 4 | 1168 | caatgacaacatgggcttct | 133 | *H. sapiens* | 565 |
| 220284 | 4 | 1187 | tggtggatcctgcggttccc | 134 | *H. sapiens* | 566 |
| 220285 | 4 | 1230 | acttcttcatcttcgtccgc | 135 | *H. sapiens* | 567 |

TABLE 3-continued

Sequence and position of preferred target segments identified in glucagon receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 220286 | 4 | 1638 | gtggcagccaggattcatct | 136 | *H. sapiens* | 568 |
| 220287 | 4 | 1727 | cagctagggctggactctgg | 137 | *H. sapiens* | 569 |
| 220288 | 4 | 1732 | agggctggactctggcaccc | 138 | *H. sapiens* | 570 |
| 220289 | 4 | 1735 | gctggactctggcacccaga | 139 | *H. sapiens* | 571 |
| 220290 | 4 | 1736 | ctggactctggcacccagag | 140 | *H. sapiens* | 572 |
| 220291 | 4 | 1737 | tggactctggcacccagagg | 141 | *H. sapiens* | 573 |
| 220292 | 4 | 1740 | actctggcacccagaggcgt | 142 | *H. sapiens* | 574 |
| 220293 | 4 | 1760 | cgctggacaacccagaactg | 143 | *H. sapiens* | 575 |
| 220294 | 4 | 1849 | ctgtctgcgagattgggcct | 144 | *H. sapiens* | 576 |
| 220295 | 4 | 1850 | tgtctgcgagattgggcctc | 145 | *H. sapiens* | 577 |
| 220296 | 4 | 1856 | cgagattgggcctcctctcc | 146 | *H. sapiens* | 578 |
| 220297 | 4 | 1861 | ttgggcctcctctccctgca | 147 | *H. sapiens* | 579 |
| 220298 | 4 | 1883 | tgccttgtccctggtgcaga | 148 | *H. sapiens* | 580 |
| 220299 | 4 | 1891 | ccctggtgcagaggtgagca | 149 | *H. sapiens* | 581 |
| 220302 | 4 | 1905 | tgagcagaggagtccagggc | 152 | *H. sapiens* | 582 |
| 220303 | 4 | 1932 | ggggctgtgccgtgaactgc | 153 | *H. sapiens* | 583 |
| 220305 | 4 | 1945 | gaactgcgtgccagtgtccc | 155 | *H. sapiens* | 584 |
| 220306 | 4 | 1971 | tgtcggcacgtcccatgtgc | 156 | *H. sapiens* | 585 |
| 220307 | 4 | 1984 | catgtgcatggaaatgtcct | 157 | *H. sapiens* | 586 |
| 220308 | 4 | 1986 | tgtgcatggaaat.gtcctcc | 158 | *H. sapiens* | 587 |
| 220309 | 4 | 1999 | gtcctccaacaataaagagc | 159 | *H. sapiens* | 588 |
| 220310 | 4 | 2001 | ccticcaacaataaagagctc | 160 | *H. sapiens* | 589 |
| 220311 | 4 | 2008 | caataaagagctcaagtggt | 161 | *H. sapiens* | 590 |
| 220312 | 18 | 3174 | ctggggacgccaaaactgcc | 162 | *H. sapiens* | 591 |
| 220314 | 18 | 7544 | tagacacgcacatcctatcc | 164 | *H. sapiens* | 592 |
| 220316 | 18 | 14888 | ctaccctgcagagctggtgt | 166 | *H. sapiens* | 593 |
| 226083 | 4 | 258 | gcagctagctgcccagaggc | 168 | *H. sapiens* | 594 |
| 226084 | 4 | 317 | ctgctgctgctggcctgcca | 169 | *H. sapiens* | 595 |
| 226085 | 4 | 321 | tgctgctggcctgccagcca | 170 | *H. sapiens* | 596 |
| 226086 | 4 | 347 | ccctccgctcaggtgatgga | 171 | *H. sapiens* | 597 |
| 226089 | 4 | 365 | gacttcctgtttgagaagtg | 174 | *H. sapiens* | 598 |
| 110281 | 4 | 397 | tgaccagtgtcaccacaacc | 177 | *H. sapiens* | 599 |
| 226092 | 4 | 403 | gtgtcaccacaacctgagcc | 178 | *H. sapiens* | 600 |
| 226093 | 4 | 452 | aacagaaccttcgacaagta | 179 | *H. sapiens* | 601 |
| 226094 | 4 | 458 | accttcgacaagtattcctg | 180 | *H. sapiens* | 602 |
| 226095 | 4 | 493 | cgccaataccacggccaaca | 181 | *H. sapiens* | 603 |

TABLE 3-continued

Sequence and position of preferred target segments identified in glucagon receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 226096 | 4 | 497 | aataccacggccaacatctc | 182 | *H. sapiens* | 604 |
| 226097 | 4 | 500 | accacggccaacatctcctg | 183 | *H. sapiens* | 605 |
| 226098 | 4 | 532 | gccttggcaccacaaagtgc | 184 | *H. sapiens* | 606 |
| 110288 | 4 | 540 | accacaaagtgcaacaccgc | 185 | *H. sapiens* | 607 |
| 226099 | 4 | 544 | caaagtgcaacaccgcttcg | 186 | *H. sapiens* | 608 |
| 226100 | 4 | 548 | gtgcaacaccgcttcgtgtt | 187 | *H. sapiens* | 609 |
| 226101 | 4 | 556 | ccgcttcgtgttcaagagat | 188 | *H. sapiens* | 610 |
| 226103 | 4 | 588 | gtcagtgggtgcgtggaccc | 189 | *H. sapiens* | 611 |
| 226104 | 4 | 606 | cccgggggcagccttggcgt | 190 | *H. sapiens* | 612 |
| 226106 | 4 | 683 | aagatgtacagcagcttcca | 192 | *H. sapiens* | 613 |
| 226107 | 4 | 687 | tgtacagcagcttccaggtg | 193 | *H. sapiens* | 614 |
| 226108 | 4 | 691 | cagcagcttccaggtgatgt | 194 | *H. sapiens* | 615 |
| 226109 | 4 | 695 | agcttccaggtgatgtacac | 195 | *H. sapiens* | 616 |
| 226110 | 4 | 720 | gctacagcctgtccctgggg | 196 | *H. sapiens* | 617 |
| 226111 | 4 | 723 | acagcctgtccctgggggcc | 197 | *H. sapiens* | 618 |
| 226112 | 4 | 860 | gatgggctgctcaggacccg | 198 | *H. sapiens* | 619 |
| 226113 | 4 | 864 | ggctgctcaggacccgctac | 199 | *H. sapiens* | 620 |
| 226114 | 4 | 868 | gctcaggacccgctacagcc | 200 | *H. sapiens* | 621 |
| 226115 | 4 | 919 | ctggctcagtgatggagcgg | 201 | *H. sapiens* | 622 |
| 226116 | 4 | 923 | ctcagtgatggagcggtggc | 202 | *H. sapiens* | 623 |
| 226117 | 4 | 951 | gtgtggccgcggtgttcatg | 203 | *H. sapiens* | 624 |
| 226118 | 4 | 955 | ggccgcggtgttcatgcaat | 204 | *H. sapiens* | 625 |
| 226119 | 4 | 960 | cggtgttcatgcaatatggc | 205 | *H. sapiens* | 626 |
| 226120 | 4 | 1019 | tacctgcacaacctgctggg | 206 | *H. sapiens* | 627 |
| 226121 | 4 | 1025 | cacaacctgctgggcctggc | 207 | *H. sapiens* | 628 |
| 226122 | 4 | 1029 | acctgctgggcctggccacc | 208 | *H. sapiens* | 629 |
| 226123 | 4 | 1055 | gagaggagcttcttcagcct | 209 | *H. sapiens* | 630 |
| 226124 | 4 | 1059 | ggagcttcttcagcctctac | 210 | *H. sapiens* | 631 |
| 226126 | 4 | 1068 | tcagcctctacctgggcatc | 212 | *H. sapiens* | 632 |
| 110302 | 4 | 1072 | cctctacctgggcatcggct | 213 | *H. sapiens* | 633 |
| 226127 | 4 | 1156 | gtgctggaccagcaatgaca | 214 | *H. sapiens* | 634 |
| 226128 | 4 | 1160 | tggaccagcaatgacaacat | 215 | *H. sapiens* | 635 |
| 226129 | 4 | 1167 | gcaatgacaacatgggcttc | 216 | *H. sapiens* | 636 |
| 226130 | 4 | 1173 | acaacatgggcttctggtgg | 217 | *H. sapiens* | 637 |
| 226131 | 4 | 1176 | acatgggcttctggtggatc | 218 | *H. sapiens* | 638 |
| 226132 | 4 | 1185 | tctggtggatcctgcggttc | 219 | *H. sapiens* | 639 |
| 226134 | 4 | 1209 | tcttcctggccatcctgatc | 221 | *H. sapiens* | 640 |

TABLE 3-continued

Sequence and position of preferred target segments identified in glucagon receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 226138 | 4 | 1290 | tgcaccacacagactacaag | 225 | *H. sapiens* | 641 |
| 226140 | 4 | 1414 | cgccaagctcttcttcgacc | 227 | *H. sapiens* | 642 |
| 226143 | 4 | 1669 | cttggctggtggcctcccta | 230 | *H. sapiens* | 643 |
| 231032 | 4 | 686 | atgtacagcagcttccaggt | 231 | *H. sapiens* | 644 |
| 231034 | 4 | 1424 | ttcttcgacctcttcctcag | 233 | *H. sapiens* | 645 |
| 231036 | 4 | 1212 | tcctggccatcctgatcaac | 235 | *H. sapiens* | 646 |
| 231037 | 4 | 1062 | gcttcttcagcctctacctg | 236 | *H. sapiens* | 647 |
| 231038 | 4 | 559 | cttcgtgttcaagagatgcg | 237 | *H. sapiens* | 648 |
| 231039 | 4 | 543 | acaaagtgcaacaccgcttc | 238 | *H. sapiens* | 649 |
| 231041 | 4 | 1026 | acaacctgctgggcctggcc | 240 | *H. sapiens* | 650 |
| 231042 | 4 | 1070 | agcctctacctgggcatcgg | 241 | *H. sapiens* | 651 |
| 231043 | 4 | 496 | caataccacggccaacatct | 242 | *H. sapiens* | 652 |
| 231044 | 4 | 399 | accagtgtcaccacaacctg | 243 | *H. sapiens* | 653 |
| 231046 | 4 | 392 | tacggtgaccagtgtcacca | 245 | *H. sapiens* | 654 |
| 231047 | 4 | 402 | agtgtcaccacaacctgagc | 246 | *H. sapiens* | 655 |
| 110287 | 4 | 533 | ccttggcaccacaaagtgca | 247 | *H. sapiens* | 656 |
| 231048 | 4 | 689 | tacagcagcttccaggtgat | 248 | *H. sapiens* | 657 |
| 231049 | 4 | 956 | gccgcggtgttcatgcaata | 249 | *H. sapiens* | 658 |
| 231051 | 4 | 555 | accgcttcgtgttcaagaga | 251 | *H. sapiens* | 659 |
| 231052 | 4 | 553 | acaccgcttcgtgttcaaga | 252 | *H. sapiens* | 660 |
| 231053 | 4 | 1027 | caacctgctgggcctggcca | 253 | *H. sapiens* | 661 |
| 231054 | 4 | 871 | caggacccgctacagccaga | 254 | *H. sapiens* | 662 |
| 231055 | 4 | 498 | ataccacggccaacatctcc | 255 | *H. sapiens* | 663 |
| 231056 | 4 | 259 | cagctagctgcccagaggca | 256 | *H. sapiens* | 664 |
| 231057 | 4 | 1058 | aggagcttcttcagcctcta | 257 | *H. sapiens* | 665 |
| 231058 | 4 | 348 | cctccgctcaggtgatggac | 258 | *H. sapiens* | 666 |
| 231061 | 4 | 953 | gtggccgcggtgttcatgca | 261 | *H. sapiens* | 667 |
| 231062 | 4 | 1024 | gcacaacctgctgggcctgg | 262 | *H. sapiens* | 668 |
| 231063 | 4 | 1061 | agcttcttcagcctctacct | 263 | *H. sapiens* | 669 |
| 231064 | 4 | 1169 | aatgacaacatgggcttctg | 264 | *H. sapiens* | 670 |
| 231066 | 4 | 1021 | cctgcacaacctgctgggcc | 266 | *H. sapiens* | 671 |
| 231067 | 4 | 400 | ccagtgtcaccacaacctga | 267 | *H. sapiens* | 672 |
| 231068 | 4 | 1165 | cagcaatgacaacatgggct | 268 | *H. sapiens* | 673 |
| 231069 | 4 | 363 | tggacttcctgtttgagaag | 269 | *H. sapiens* | 674 |
| 231070 | 4 | 550 | gcaacaccgcttcgtgttca | 270 | *H. sapiens* | 675 |
| 231071 | 4 | 367 | cttcctgtttgagaagtgga | 271 | *H. sapiens* | 676 |

TABLE 3-continued

Sequence and position of preferred target segments identified in glucagon receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 231073 | 4 | 1071 | gcctctacctgggcatcggc | 273 | *H. sapiens* | 677 |
| 231075 | 4 | 349 | ctccgctcaggtgatggact | 275 | *H. sapiens* | 678 |
| 231077 | 4 | 463 | cgacaagtattcctgctggc | 278 | *H. sapiens* | 679 |
| 231078 | 4 | 320 | ctgctgctggcctgccagcc | 279 | *H. sapiens* | 680 |
| 231079 | 4 | 1183 | cttctggtggatcctgcggt | 280 | *H. sapiens* | 681 |
| 231080 | 4 | 862 | tgggctgctcaggacccgct | 281 | *H. sapiens* | 682 |
| 231081 | 4 | 565 | gttcaagagatgcgggcccg | 282 | *H. sapiens* | 683 |
| 231083 | 4 | 1177 | catgggcttctggtggatcc | 284 | *H. sapiens* | 684 |
| 231085 | 4 | 1184 | ttctggtggatcctgcggtt | 286 | *H. sapiens* | 685 |
| 231086 | 4 | 410 | cacaacctgagcctgctgcc | 287 | *H. sapiens* | 686 |
| 231087 | 4 | 495 | ccaataccacggccaacatc | 288 | *H. sapiens* | 687 |
| 231090 | 4 | 688 | gtacagcagcttccaggtga | 291 | *H. sapiens* | 688 |
| 231092 | 4 | 863 | gggctgctcaggacccgcta | 293 | *H. sapiens* | 689 |
| 231096 | 4 | 694 | cagcttccaggtgatgtaca | 297 | *H. sapiens* | 690 |
| 231097 | 4 | 494 | gccaataccacggccaacat | 298 | *H. sapiens* | 691 |
| 110307 | 4 | 1178 | atgggcttctggtggatcct | 300 | *H. sapiens* | 692 |
| 231099 | 4 | 1207 | cgtcttcctggccatcctga | 301 | *H. sapiens* | 693 |
| 231100 | 4 | 352 | cgctcaggtgatggacttcc | 302 | *H. sapiens* | 694 |
| 231101 | 4 | 261 | gctagctgcccagaggcatg | 303 | *H. sapiens* | 695 |
| 231102 | 4 | 561 | tcgtgttcaagagatgcggg | 304 | *H. sapiens* | 696 |
| 231103 | 4 | 323 | ctgctggcctgccagccaca | 305 | *H. sapiens* | 697 |
| 231104 | 4 | 324 | tgctggcctgccagccacag | 306 | *H. sapiens* | 698 |
| 231105 | 4 | 1179 | tgggcttctggtggatcctg | 307 | *H. sapiens* | 699 |
| 231107 | 4 | 1289 | atgcaccacacagactacaa | 309 | *H. sapiens* | 700 |
| 231108 | 4 | 322 | gctgctggcctgccagccac | 310 | *H. sapiens* | 701 |
| 231109 | 4 | 406 | tcaccacaacctgagcctgc | 311 | *H. sapiens* | 702 |
| 231110 | 4 | 870 | tcaggacccgctacagccag | 312 | *H. sapiens* | 703 |
| 231112 | 4 | 464 | gacaagtattcctgctggcc | 314 | *H. sapiens* | 704 |
| 231114 | 4 | 1060 | gagcttcttcagcctctacc | 316 | *H. sapiens* | 705 |
| 231115 | 4 | 1422 | tcttcttcgacctcttcctc | 317 | *H. sapiens* | 706 |
| 231118 | 4 | 542 | cacaaagtgcaacaccgctt | 321 | *H. sapiens* | 707 |
| 231119 | 4 | 456 | gaaccttcgacaagtattcc | 322 | *H. sapiens* | 708 |
| 231122 | 4 | 404 | tgtcaccacaacctgagcct | 325 | *H. sapiens* | 709 |
| 231123 | 4 | 538 | gcaccacaaagtgcaacacc | 326 | *H. sapiens* | 710 |
| 231126 | 4 | 954 | tggccgcggtgttcatgcaa | 329 | *H. sapiens* | 711 |
| 231127 | 4 | 684 | agatgtacagcagcttccag | 330 | *H. sapiens* | 712 |
| 231129 | 4 | 1214 | ctggccatcctgatcaactt | 332 | *H. sapiens* | 713 |

TABLE 3-continued

Sequence and position of preferred target segments identified in glucagon receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 231130 | 4 | 1023 | tgcacaacctgctgggcctg | 333 | *H. sapiens* | 714 |
| 231133 | 4 | 554 | caccgcttcgtgttcaagag | 336 | *H. sapiens* | 715 |
| 231135 | 4 | 499 | taccacggccaacatctcct | 338 | *H. sapiens* | 716 |
| 231136 | 4 | 1164 | ccagcaatgacaacatgggc | 339 | *H. sapiens* | 717 |
| 231138 | 4 | 1064 | ttcttcagcctctacctggg | 341 | *H. sapiens* | 718 |
| 231139 | 4 | 1163 | accagcaatgacaacatggg | 342 | *H. sapiens* | 719 |
| 231140 | 4 | 547 | agtgcaacaccgcttcgtgt | 343 | *H. sapiens* | 720 |
| 231141 | 4 | 408 | accacaacctgagcctgctg | 344 | *H. sapiens* | 721 |
| 231143 | 4 | 1020 | acctgcacaacctgctgggc | 346 | *H. sapiens* | 722 |
| 231145 | 4 | 562 | cgtgttcaagagatgcgggc | 348 | *H. sapiens* | 723 |
| 231146 | 4 | 1418 | aagctcttcttcgacctctt | 349 | *H. sapiens* | 724 |
| 231148 | 4 | 557 | cgcttcgtgttcaagagatg | 351 | *H. sapiens* | 725 |
| 231150 | 4 | 1155 | agtgctggaccagcaatgac | 353 | *H. sapiens* | 726 |
| 231151 | 4 | 566 | ttcaagagatgcgggcccga | 354 | *H. sapiens* | 727 |
| 231152 | 4 | 721 | ctacagcctgtccctggggg | 355 | *H. sapiens* | 728 |
| 110306 | 4 | 1162 | gaccagcaatgacaacatgg | 356 | *H. sapiens* | 729 |
| 231154 | 4 | 549 | tgcaacaccgcttcgtgttc | 358 | *H. sapiens* | 730 |
| 231155 | 4 | 1159 | ctggaccagcaatgacaaca | 360 | *H. sapiens* | 731 |
| 231156 | 4 | 457 | aaccttcgacaagtattcct | 361 | *H. sapiens* | 732 |
| 231160 | 4 | 546 | aagtgcaacaccgcttcgtg | 365 | *H. sapiens* | 733 |
| 231162 | 4 | 260 | agctagctgcccagaggcat | 367 | *H. sapiens* | 734 |
| 231163 | 4 | 690 | acagcagcttccaggtgatg | 368 | *H. sapiens* | 735 |
| 231165 | 4 | 558 | gcttcgtgttcaagagatgc | 370 | *H. sapiens* | 736 |
| 231166 | 4 | 958 | cgcggtgttcatgcaatatg | 371 | *H. sapiens* | 737 |
| 231168 | 4 | 867 | tgctcaggacccgctacagc | 373 | *H. sapiens* | 738 |
| 231169 | 4 | 865 | gctgctcaggacccgctaca | 374 | *H. sapiens* | 739 |
| 231171 | 4 | 692 | agcagcttccaggtgatgta | 376 | *H. sapiens* | 740 |
| 231172 | 4 | 1181 | ggcttctggtggatcctgcg | 377 | *H. sapiens* | 741 |
| 231174 | 4 | 1057 | gaggagcttcttcagcctct | 379 | *H. sapiens* | 742 |
| 231175 | 4 | 1211 | ttcctggccatcctgatcaa | 380 | *H. sapiens* | 743 |
| 231176 | 4 | 541 | ccacaaagtgcaacaccgct | 381 | *H. sapiens* | 744 |
| 231177 | 4 | 319 | gctgctgctggcctgccagc | 382 | *H. sapiens* | 745 |
| 231178 | 4 | 545 | aaagtgcaacaccgcttcgt | 383 | *H. sapiens* | 746 |
| 231179 | 4 | 952 | tgtggccgcggtgttcatgc | 384 | *H. sapiens* | 747 |
| 231181 | 4 | 1180 | gggcttctggtggatcctgc | 386 | *H. sapiens* | 748 |
| 231183 | 4 | 722 | tacagcctgtccctgggggc | 388 | *H. sapiens* | 749 |

TABLE 3-continued

Sequence and position of preferred target segments identified in glucagon receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 231185 | 4 | 957 | ccgcggtgttcatgcaatat | 390 | *H. sapiens* | 750 |
| 231186 | 4 | 459 | ccttcgacaagtattcctgc | 391 | *H. sapiens* | 751 |
| 110293 | 4 | 693 | gcagcttccaggtgatgtac | 392 | *H. sapiens* | 752 |
| 231187 | 4 | 1153 | ccagtgctggaccagcaatg | 393 | *H. sapiens* | 753 |
| 110319 | 4 | 551 | caacaccgcttcgtgttcaa | 396 | *H. sapiens* | 754 |
| 231190 | 4 | 1171 | tgacaacatgggcttctggt | 397 | *H. sapiens* | 755 |
| 63771 | 11 | 138 | caacctctgccagatgtggg | 404 | *M. musculus* | 756 |
| 63777 | 11 | 274 | gtttgagaagtggaagctct | 406 | *M. musculus* | 757 |
| 63778 | 11 | 284 | tggaagctctatagtgacca | 407 | *M. musculus* | 758 |
| 63780 | 11 | 308 | caccacaacctaagcctgct | 408 | *M. musculus* | 759 |
| 63784 | 11 | 403 | cactgccaacatttcctgcc | 409 | *M. musculus* | 760 |
| 63787 | 11 | 464 | gtgttcaagaggtgtgggcc | 410 | *M. musculus* | 761 |
| 63789 | 11 | 558 | agatcgaggtccagaagggg | 411 | *M. musculus* | 762 |
| 63792 | 11 | 619 | gggctacagtctgtccctgg | 412 | *M. musculus* | 763 |
| 63793 | 11 | 670 | gggcctcaggaagctgcact | 413 | *M. musculus* | 764 |
| 63802 | 11 | 1019 | ccctgggtggtggtcaagtg | 414 | *M. musculus* | 765 |
| 63806 | 11 | 1058 | tgctggaccagcaatgacaa | 416 | *M. musculus* | 766 |
| 63808 | 11 | 1079 | atgggattctggtggatcct | 417 | *M. musculus* | 767 |
| 63811 | 11 | 1220 | gccaggtccacgctgaccct | 418 | *M. musculus* | 768 |
| 95505 | 400 | 14 | gcaacctgaggagaggtgca | 424 | *M. musculus* | 769 |
| 95506 | 400 | 25 | agaggtgcacacactctgag | 425 | *M. musculus* | 770 |
| 95507 | 400 | 30 | tgcacacactctgaggacct | 426 | *M. musculus* | 771 |
| 95508 | 400 | 48 | ctaggtgtgcaacctctgcc | 427 | *M. musculus* | 772 |
| 95509 | 400 | 80 | tggctacccagaggcatgcc | 428 | *M. musculus* | 773 |
| 95511 | 400 | 192 | tgtttgagaagtggaagctc | 430 | *M. musculus* | 774 |
| 95512 | 400 | 251 | ccacctactgagctggtctg | 431 | *M. musculus* | 775 |
| 95513 | 400 | 291 | actcctgctggcctgacacc | 432 | *M. musculus* | 776 |
| 95514 | 400 | 359 | tgccacaaagtgcagcaccg | 433 | *M. musculus* | 777 |
| 95515 | 400 | 371 | cagcaccgcctagtgttcaa | 434 | *M. musculus* | 778 |
| 95516 | 400 | 410 | cagtgggttcgagggccacg | 435 | *M. musculus* | 779 |
| 95517 | 400 | 545 | agtctgtccctgggggcctt | 436 | *M. musculus* | 780 |
| 95518 | 400 | 572 | gcgctggtcatcctgctggg | 437 | *M. musculus* | 781 |
| 95519 | 400 | 582 | tcctgctgggcctcaggaag | 438 | *M. musculus* | 782 |
| 95520 | 400 | 650 | gtgctcaaggctggctctgt | 439 | *M. musculus* | 783 |
| 95521 | 400 | 764 | ggctgcagagtggccacagt | 440 | *M. musculus* | 784 |
| 95522 | 400 | 775 | ggccacagtgatcatgcagt | 441 | *M. musculus* | 785 |
| 95523 | 400 | 785 | atcatgcagtacggcatcat | 442 | *M. musculus* | 786 |

TABLE 3-continued

Sequence and position of preferred target segments identified in glucagon receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 95524 | 400 | 836 | gtgtacctgtacagcctgct | 443 | *M. musculus* | 787 |
| 95525 | 400 | 974 | cagtgctggaccagcaatga | 444 | *M. musculus* | 788 |
| 95527 | 400 | 1079 | cttcttgtggccaagctgcg | 446 | *M. musculus* | 789 |
| 95529 | 400 | 1100 | gcccatcagatgcactatgc | 448 | *M. musculus* | 790 |
| 95531 | 400 | 1256 | ttcctcagctccttccaggg | 450 | *M. musculus* | 791 |
| 95532 | 400 | 1292 | ctctactgtttcctcaacaa | 451 | *M. musculus* | 792 |
| 95533 | 400 | 1348 | atggcaagaaggcaaagctc | 452 | *M. musculus* | 793 |
| 95534 | 400 | 1360 | caaagctcttcaggaggaaa | 453 | *M. musculus* | 794 |
| 95535 | 400 | 1388 | agcagccatggcagccacat | 454 | *M. musculus* | 795 |
| 95536 | 400 | 1435 | tccctgtgagaaacttcagc | 455 | *M. musculus* | 796 |
| 95537 | 400 | 1450 | tcagcttatgagtgcaggca | 456 | *M. musculus* | 797 |
| 95538 | 400 | 1470 | gcagcagtgggactggctgt | 457 | *M. musculus* | 798 |
| 95539 | 400 | 1512 | tggccagtagtctcccaagg | 458 | *M. musculus* | 799 |
| 95540 | 400 | 1544 | cccacctgaatctccacttg | 459 | *M. musculus* | 800 |
| 95542 | 400 | 1575 | ggttgtgttcaagaaagggc | 461 | *M. musculus* | 801 |
| 95543 | 400 | 1600 | aggacaacccagagccagat | 462 | *M. musculus* | 802 |
| 95544 | 400 | 1610 | agagccagatgcccggccaa | 463 | *M. musculus* | 803 |
| 95545 | 400 | 1620 | gcccggccaaggttgaagag | 464 | *M. musculus* | 804 |
| 95546 | 400 | 1646 | cagcaagacagcagcttgta | 465 | *M. musculus* | 805 |
| 95547 | 400 | 1687 | gtcctagcctggcacaggcc | 466 | *M. musculus* | 806 |
| 95548 | 400 | 1724 | gttggatatgatggagaagc | 467 | *M. musculus* | 807 |
| 95549 | 400 | 1750 | atctatgaactctgagtgtt | 468 | *M. musculus* | 808 |
| 95550 | 400 | 1756 | gaactctgagtgttcccatg | 469 | *M. musculus* | 809 |
| 95551 | 400 | 1795 | tacccagatatgtccttcag | 470 | *M. musculus* | 810 |
| 95552 | 401 | 3953 | cttggtctcgcctttgttac | 471 | *M. musculus* | 811 |
| 95554 | 401 | 7321 | accttcacagagctggtctg | 473 | *M. musculus* | 812 |
| 95555 | 401 | 7505 | ccatgcccagtgcagcaccg | 474 | *M. musculus* | 813 |
| 95557 | 401 | 8766 | gtcaggttgcccatccttgg | 476 | *M. musculus* | 814 |
| 95560 | 11 | 10 | tcatgaggccttgggcttgg | 479 | *M. musculus* | 815 |
| 95561 | 11 | 85 | ctggtcctctgcagcctgag | 480 | *M. musculus* | 816 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of glucagon receptor.

According to the present invention, antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 17

Western Blot Analysis of Glucagon Receptor Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to glucagon receptor is used, with a radiolabeled or fluorescently labeled secondary antibody directed against the primary antibody species. Bands are visualized using a PHOSPHORIMAGER™ (Molecular Dynamics, Sunnyvale Calif.).

Example 18

Effects of Antisense Inhibition of Glucagon Receptor in Mice on Plasma Glucose Levels and Glucagon Receptor mRNA Reduction: Lean Animals, db/db Mice and ob/ob Mice In accordance with the present invention, two antisense oligonucleotides targeted to the mouse glucagon receptor, ISIS 148359 (agcaggctta ggttgtggtg, SEQ ID NO: 408) and ISIS 180475 (gagctttgcc ttcttgccat, SEQ ID NO: 452), were evaluated for therapeutic efficacy in art-accepted mouse models of obesity and diabetes. Ob/ob mice have mutations in the leptin gene and are leptin-deficient, while db/db mice have mutations in the leptin receptor gene. The two strains exhibit obesity and diabetes strongly resembling Type 2 diabetes in humans. Tsang, S. H., 1998, *P & S Medical Review*, Vol. 5, No. 1.

Db/db and ob/ob mice were evaluated over the course of 4 weeks for the effects of ISIS 148359 and ISIS 180475 on serum glucose levels and glucagon receptor mRNA levels, while normoglycemic mice were evaluated for 2 weeks. Control animals received saline treatment (50 mg/kg). The normoglycemic mice were dosed subcutaneously twice a week for 2 weeks with 50 mg/kg of ISIS 148359, ISIS 180475 or saline. The db/db and ob/ob mice were dosed subcutaneously twice a week for 6 weeks with 25 mg/kg of ISIS 148359, ISIS 180475, saline, the positive control oligonucleotide ISIS 116847 (ctgctagcc tctggatttga, SEQ ID NO: 817) or the negative control oligonucleotide ISIS 141923 (ccttccctga aggttcctcc, SEQ ID NO: 818). The mice were monitored weekly for fed or fasted plasma glucose levels (fasted glucose measured 16 hr after last feeding) and upon termination of the experiment the level of glucagon receptor mRNA in the liver was determined. The data are summarized in Table 4.

TABLE 4

Effects of ISIS 148359 and ISIS 180475 treatment on fed and fasting glucose levels and glucagon receptor mRNA levels in normoglycemic mice, db/db mice, and ob/ob mice

| Biological Marker Measured | mice (time course of study) | day of treatment | ISIS # Antisense Oligonucleotides 148359 | 180475 | Controls saline | 116847 | 141923 |
|---|---|---|---|---|---|---|---|
| fed | lean mice | −6 | 221 | 216 | 210 | N.D. | N.D. |
| plasma | (2 week) | 15 | 151 | 130 | 181 | N.D. | N.D. |
| glucose | db/db mice | −1 | 294 | 295 | 296 | 295 | 304 |
| mg/dL | (4 weeks) | 5 | 361 | 329 | 460 | 355 | 408 |
| | | 12 | 375 | 303 | 510 | 303 | 425 |
| | | 26 | 314 | 222 | 495 | 354 | 493 |
| | ob/ob mice | −1 | 338 | 342 | 343 | 337 | 361 |
| | (4 weeks) | 12 | 245 | 180 | 426 | 227 | 476 |
| | | 27 | 168 | 145 | 394 | 205 | 431 |
| fasted | db/db mice | 19 | 336 | 232 | 320 | 321 | 298 |
| plasma | (4 weeks) | 29 | 254 | 150 | 302 | 193 | 262 |
| glucose | ob/ob mice | 19 | 205 | 132 | 317 | 167 | 245 |
| mg/dL | (4 weeks) | 29 | 178 | 117 | 322 | 189 | 340 |
| glucagon receptor | lean mice (2 week) | end | 82 | 93 | 0 | N.D. | N.D. |
| % mRNA reduction | db/db mice (4 weeks) | end | 74 | 96 | 0 | 0 | 0 |
| | ob/ob mice (4 weeks) | end | 86 | 97 | 0 | 10 | 0 |

These data demonstrate that the antisense oligonucleotides ISIS 148359 and ISIS 180475 targeted to glucagon receptor mRNA are capable of decreasing levels of glucagon receptor mRNA in mouse liver. These data further demonstrate that reduction of glucagon receptor expression is accompanied by a decrease in plasma glucose levels in normoglycemic mice, db/db mice and ob/ob mice. It is important to note that the treated mice become normoglycemic and do not become hypoglycemic. Antisense inhibitors of glucagon receptor are thus believed to be useful therapeutic modalities for treatment of hyperglycemia.

Example 19

Glucagon Receptor Antisense Oligonucleotides Lower Plasma Glucose in ob/ob Diabetic Mice—4 Week Study C57Bl/eOlaHsd-Lep$_{ob}$ (ob/ob) male mice were purchased from Harlan (Indianapolis, Ind., USA). Animals were acclimated for one week prior to study initiation. Mice were housed five per cage in polycarbonate cages with filter tops. Animals were maintained on a 12:12 hr light-dark cycle (lights on at 6:00 AM) at 21° C. All animals received deionized water ad libitum. ob/ob mice received Purina Diet 5015 ad libitum. Antisense compounds were prepared in normal saline, and the solution was sterilized through a 0.2 μm filter. Animals were dosed with antisense compound solutions or vehicle (saline) twice per week (separated by 3.5 days) via subcutaneous injection. Before the initiation of each study and once weekly during the study, blood was collected by tail clip without anesthesia into EDTA plasma tubes containing trasylol (Serologicals Proteins, Kankakee, Ill., USA) and dipeptidyl peptidase (DPP)-IV inhibitor (Linco Diagnostic Services, St. Charles, Mo., USA). Food intake and body weights were measured weekly. Plasma levels of glucose and triglycerides were determined on the Hitachi 912 clinical chemistry analyzer (Roche, Indianapolis, Ind., USA).

To test the efficacy of antisense inhibitors of glucagon receptor to treat hyperglycemia, 7–8 week-old ob/ob mice were dosed two times per week with antisense inhibitors of glucagon receptor [ISIS 148359 (SEQ ID NO: 408) or ISIS 180475(SEQ ID NO: 452)], a generic control oligonucleotide (ISIS 141923; SEQ ID NO: 818) whose sequence does not match any known transcripts in the mouse or rat genomes, a mismatch oligonucleotide (ISIS 298682; GCGATTTCCCGTTTTGACCT; SEQ ID NO: 819) whose sequence is identical to ISIS 180475 except for 7 internal bases, or saline twice a week (every 3.5 days) for 4 weeks. All oligonucleotides were administered at 25 mg/kg. Data are the mean values (+_SEM where shown) of 8 mice per treatment group. Plasma glucose levels in all mice were approximately 330–370 mg/dl day zero. Whereas hyperglycemia worsened over time in saline—and control oligonucleotide—treated ob/ob mice, animals treated with glucagon receptor antisense compounds showed a dramatic reduction in plasma glucose. At day 12, plasma glucose levels in ob/ob mice treated with control oligonucleotide (ISIS 141923) and saline were approximately 472 and 425 mg/dl, respectively. Plasma glucose levels in mice treated with antisense oligonucleotides ISIS 148359 and ISIS 180475 were 240 and 180 mg/dl, respectively. At day 27, plasma glucose levels in ob/ob mice treated with control oligonucleotide (ISIS 141923) and saline were approximately 435 and 390 mg/dl, respectively. Plasma glucose levels in mice treated with antisense oligonucleotides ISIS 148359 and ISIS 180475 were 165 and 130 mg/dl, respectively. The latter is in the normal range.

A separate study, also using ob/ob mice (as well as db/db mice, lean mice, ZDF rats and lean rats) was also performed in which animals were also dosed subcutaneously every 3.5 days for a total of 9 doses of glucagon receptor antisense compound ISIS 180475 and one or more controls (unrelated control oligonucleotide ISIS 141923, mismatch control oligonucleotide ISIS 298682, and/or saline). The results of this study are shown in Table 5.

At the end of the 4-week treatment period, liver glucagon receptor mRNA was measured (normalized to total RNA in the same samples using Ribogreen) and was found to be reduced by 85–95%. Data are mean values of four mice per treatment group (P<0.05 using Student's t-test).

TABLE 5

| | Effects of antisense inhibition of glucagon receptor in rodents | | | | |
|---|---|---|---|---|---|
| | Body Weight (g) | Plasma Glucose (mg/dl) | Plasma Triglycerides (mg/dl) | Plasma Insulin (ng/ml) | Plasma Glucagon (pg/ml) |
| ob/ob mice | | | | | |
| Saline | 56.5 ± 1.5 | 564 ± 118 | 163 ± 25 | 35.9 ± 13.8 | n.d. |
| ISIS 180475 | 54.1 ± 1.6 | 122 ± 6* | 129 ± 7 | 19.8 ± 9.5 | n.d. |
| db/db mice | | | | | |
| ISIS 141923 | 46.0 ± 0.7 | 571 ± 29 | 412 ± 33 | n.d. | 117 ± 12 |
| ISIS 298682 | 43.9 ± 1.3 | 577 ± 65 | 448 ± 40 | n.d. | 131 ± 20 |
| ISIS 180475 | 45.6 ± 0.6 | 241 ± 37* | 121 ± 12* | n.d. | 3765 ± 952* |
| $db^{+/?}$ lean mice | | | | | |
| ISIS 141923 | 28.0 ± 1.0 | 196 ± 12 | 121 ± 7 | n.d. | 80 ± 1 |
| ISIS 180475 | 27.6 ± 1.0 | 164 ± 4* | 83 ± 6* | n.d. | 362 ± 40* |
| ZDF rats | | | | | |
| ISIS 141923 | 403 ± 12 | 417 ± 38 | 640 ± 105 | 5.0 ± 1.9 | 136 ± 7 |
| ISIS 180475 | 404 ± 8 | 143 ± 15* | 250 ± 25* | 4.4 ± 0.5 | 548 ± 20* |
| SD lean rats | | | | | |
| Saline | 344 ± 4 | 116 ± 3 | 106 ± 26 | 2.7 ± 0.3 | 56 ± 11 |
| ISIS 180475 | 327 ± 5 | 104 ± 7 | 139 ± 58 | 1.3 ± 0.2* | 855 ± 122* |

*P < 0.05.
n.d., not determined

Example 20

Glucagon Receptor Antisense Oligonucleotides Lower Plasma Glucose in db/db Diabetic mice—4 Week Study C57Bl/KsOlaHsd-$Lep_{db}$ (db/db) and lean ($db^{+/?}$) male mice were purchased from Harlan (Indianapolis, Ind., USA). Animals were acclimated for one week prior to study initiation. Mice were housed five per cage in polycarbonate cages with filter tops. Animals were maintained on a 12:12 hr light-dark cycle (lights on at 6:00 AM) at 21° C. All animals received de-ionized water ad libitum. db/db mice received Purina Diet 5008 ad libitum. Antisense compounds were prepared in normal saline, and the solution was sterilized through a 0.2 μm filter. Animals were dosed with antisense compound solutions or vehicle (saline) twice per week (separated by 3.5 days) via subcutaneous injection. Before the initiation of each study and once weekly during the study, blood was collected by tail clip without anesthesia into EDTA plasma tubes containing trasylol (Serologicals Proteins, Kankakee, Ill., USA) and dipeptidyl peptidase (DPP)-IV inhibitor (Linco Diagnostic Services, St. Charles, Mo., USA). Food intake and body weights were measured weekly. Plasma levels of glucose and triglycerides were determined on the Hitachi 912 clinical chemistry analyzer (Roche, Indianapolis, Ind., USA.

To test the efficacy of antisense inhibitors of glucagon receptor to treat hyperglycemia, 7–8 week-old db/db mice were dosed two times per week with antisense inhibitors of glucagon receptor [ISIS 148359 (SEQ ID NO: 408) or ISIS 180475(SEQ ID NO: 452)], a generic control oligonucleotide (ISIS 141923) whose sequence does not match any known transcripts in the mouse or rat genomes, a mismatch oligonucleotide (ISIS 298682; SEQ ID NO: 819) whose sequence is identical to ISIS 180475 except for 7 internal bases, or saline for 4 weeks.

Glucose lowering efficacy and target reduction in db/db mice undergoing glucagon receptor antisense treatment were similar to those observed in similarly treated ob/ob mice; furthermore, plasma triglycerides were lowered from 412±33 to 121±12 mg/dl following glucagon receptor antisense treatment (Table 5). These results in db/db mice are similar to those reported in preliminary studies testing glucagon receptor antisense compound ISIS 148359 for 3 weeks [Osborne et al., 2003, *Diabetes* 52, A129 (abstract)].

Example 21

Glucagon Receptor Antisense Oligonucleotides Lower Plasma Glucose in ZDF Rats

ZDF/GmiCrl-fa/fa (ZDF) male rats were purchased from Charles River Laboratories (Wilmington, Mass., USA). Animals were acclimated for one week prior to study initiation. Rats were housed one per cage in polycarbonate cages with filter tops. Animals were maintained on a 12:12 hr light-dark cycle (lights on at 6:00 AM) at 21° C. All animals received de-ionized water ad libitum. ZDF rats received Purina Diet 5008 ad libitum. Antisense compounds were prepared in normal saline, and the solution was sterilized through a 0.2 μm filter. Seven-week old animals were dosed with antisense compound solutions or vehicle (saline) twice per week (separated by 3.5 days) via subcutaneous injection, for a total of 9 doses (last treatment on day 28), followed by a washout period of equal duration. Oligonucleotide concentration was 25 mg/kg of either glucagon receptor antisense oligonucleotide ISIS 180475 (SEQ ID NO: 452) or negative control oligonucleotide ISIS 141923 (SEQ ID NO: 818). Before the initiation of each study and once weekly during the study, blood was collected by tail clip without anesthesia into EDTA plasma tubes containing trasylol (Serologicals Proteins, Kankakee, Ill., USA) and dipeptidyl peptidase (DPP)-IV inhibitor (Linco Diagnostic Services, St. Charles, Mo., USA). Food intake and body weights were measured weekly. Glucagon receptor mRNA (target) was measured by real-time quantitative RT-PCR from livers of five animals removed from the study at each time point. Rat 36B4 ribosomal phosphoprotein mRNA ("18S RNA") was measured and used to normalize RNA input. Data are the mean values of five rats per treatment group. In overall comparisons during the treatment period, target reduction by glucagon receptor antisense compound ISIS 180475 was significantly different when compared to control oligonucleotide-treated animals ($P<0.05$ adjusted using the Tukey method). Liver glucagon receptor mRNA decreased dramatically to 50% of controls within 24 hours after the first dose of ISIS 180475 and to 30% of controls 48 hr following the seventh dose.

For non-fasted plasma glucose levels, rats were treated as described above. Data are the mean values of five rats per treatment group. In overall comparisons during the treatment period, glucose lowering by the glucagon receptor antisense compound ISIS 180475 showed significant difference when compared to control oligonucleotide-treated animals. ($P<0.05$ adjusted using the Tukey method). The drop in plasma glucose paralleled the drop in glucagon receptor mRNA levels; there was a significant drop in plasma glucose within 48 hours after the initial glucagon receptor antisense dose. After 9 doses, the control oligonucleotide (ISIS 141923) treated rats had plasma glucose levels averaging approximately 417 mg/dl and antisense (ISIS 180475) treated rats had plasma glucose levels averaging approximately 143 mg/dl.

During the washout phase, hyperglycemia and glucagon receptor expression in liver began to rebound within 10 days, but even one month after the final dose, efficacy was still observed as plasma glucose and target mRNA levels in washout animals remained below pre-treatment levels. Glucose lowering achieved by the twice per week dosing schedule and the gradula rebound of glucagon receptor mRNA during the washout period are both consistent with the extended half lives of 2'-methoxyethoxy modified phosphorothioate oligonucleotides (typically ranging from 9 to 19 days according to published reports).

Non-fasted plasma insulin levels were also determined for rats treated as described above. Data are the mean values of five rats per treatment group. No significant changes were observed during the treatment period; however, individual comparisons between glucagon receptor antisense and control oligonucleotide treated animals on day 38 and 56 (washout period) were significant ($P<0.05$). Plasma insulin levels declined during the treatment phase in both control oligonucleotide and antisense-treated animals. During the washout phase of the control oligonucleotide treated group, insulin levels continued to decline as hyperglycemia progressed. This result is expected since beta-cell failure typically occurs in ZDF rats between 8 and 12 weeks of age. Interestingly, the mild elevation of glucose in glucagon receptor antisense-treated animals during the washout period resulted in a robust rise in plasma insulin to levels nearly as high as at start of study. This is consistent with evidence of preserved beta-cell function.

Example 22

Glucagon Receptor Antisense Oligonucleotides do not Cause Hyperglycemia or Hypoglycemia, in Spite of Hyperglucagonemia In addition to effects on blood glucose, treatment with the antisense inhibitor of glucagon receptor (ISIS 180475; SEQ ID NO: 452) resulted in marked (and reversible) hyperglucagonemia in both normal and diabetic rodents (Table 5). This level of hyperglucagonemia is similar to that observed in glucagon receptor knockout mice (Parker et al., 2002, *Biochem Biophys Res Commun.* 290, 839–843; Gelling et al., 2003, *Proc. Natl. Acad. Sci. USA.*, 100, 1438–1443.

Because of these high levels of serum glucagon, it was important to determine whether the antisense inhibitors of glucagon receptor might induce hyperglycemia, particularly as hepatic glucagon receptor levels gradually return to normal following treatment withdrawal. It is therefore significant that at no time during the treatment or washout periods did animals with hyperglucagonemia exhibit hyperglycemia. In fact, glucagon receptor antisense-treated animals showed a moderate decrease in fed plasma glucose at all time points tested.

It was also confirmed that antisense treatment also did not cause hypoglycemia. After 4 weeks of antisense treatment, by which time maximum reduction of glucagon receptor expression had been achieved, $db^{+/?}$ lean mice were subjected to periods of fasting of up to 24 hours. Although the glucagon receptor antisense-treated mice displayed a 10–30% reduction in plasma glucose, at no time did the animals reach adverse levels of hypoglycemia. This is in contrast to Gcgr knockout mice, which become hypoglycemic during periods of fasting. Gelling et al., 2003, *Proc Natl. Acad. Sci. U.S.A.* 100, 1438–1443.

Example 23

Glucagon Receptor mRNA is Reduced in Islets of Antisense-treated db/db Mice

Pancreatic islets were isolated from 12-week-old male db/db mice (n=5–6 per treatment group) that had been treated twice per week (every 3.5 days) by subcutaneous injection with saline or glucagon receptor antisense oligonucleotide ISIS 180475 (SEQ ID NO: 452) at 25 mg/kg for a total of 9 doses. Mice were sacrificed by cervical dislocation. The common bile duct was cannulated with a 27-gauge needle and the pancreas was distended with 3 ml of Hank's buffer (Sigma, Taufkirchen, Germany) containing 2% bovine serum albumin (Applichem, Darmstadt, Germany) and 1 mg/ml collagenase (Serva, Heidelberg, Germany). Subsequently, the pancreas was removed and digested in Hank's buffer at 37° C. Islets were purified on a Histopaque-1077™ (Sigma) gradient for 15 min at 750×g. Islets were cultured overnight in RPMI-1640 medium containing 10% FBS, 100 U/ml penicillin, and 100:g/ml streptomycin (Invitrogen, Karlsruhe, Germany). 200 islets from 3 individuals were pooled to give one sample for RNA extraction. Real-time quantitative RT-PCR was used to profile gene expression. Islet glucagon receptor mRNA levels were decreased by approximately 75% in antisense-treated animals compared to saline-treated controls. It should be noted that, in addition to pharmacologic effect of the antisense compound, a compensatory response to hyperglucagonemia or the increased alpha-cell populations in treated animals could contribute to the results observed.

Example 24

Glucagon Receptor Antisense Oligonucleotides Decrease the Number of Functional Glucagon Receptors To assess whether the reduction in glucagon receptor mRNA correlates with a reduction in functional glucagon receptor number, a homologous competition assay was performed using hepatocyte membranes prepared from mice treated with control or glucagon receptor antisense compounds. $^{125}$I-glucagon binding was effectively competed by increasing concentrations of unlabeled glucagon in control membrane samples. 15–20 μg of membrane from control oligonucleotide- or glucagon receptor oligonucleotide (ISIS 180475; SEQ ID NO: 452)-treated db/db mice were incubated with 0.1 nM $^{125}$I-glucagon (2000 Ci/mmol, PerkinElmer, Boston, Mass., USA) and the indicated concentrations of unlabeled glucagon (Eli Lilly and Company, Indianapolis, Ind., USA) in buffer containing 50 mM Hepes, 1 mM $MgCl_2$, 5 mM EGTA, 0.005% Tween 20, 0.1% BSA, and EDTA-free protease inhibitor cocktail (Roche). Assays were performed under steady state conditions in the presence of excess labeled ligand on 96-well MultiScreen-HV 0.45 μm filter plates (Millipore, Bedford, Mass., USA). Following incubation for 2 hrs at room temperature, plates were rapidly washed by filtration with ice-cold buffer (20 mM Tris, pH 7.4) and dried for 45 min at 50° C. Following the addition of Optiphase Supermix (PerkinElmer), plates were counted on a Wallac Microbeta scintillation counter. Data analyses were performed using GraphPad Prism software and expressed as mean +/− SEM. Data obtained for samples from animals treated with glucagon receptor oligonucleotide neared the limits of detection for the assay and curve-fitting parameters. In order to derive a numerical value for apparent Bmax, the Kd was fixed at the average value (0.69+/−0.2 nM) obtained from the samples from the control antisense-treated animals.

Functional GCGR expression was found to be decreased approximately 85% by glucagon receptor antisense treatment and is in accord with quantitative RT-PCR results.

Example 25

Antisense Inhibitors of Human and Monkey Glucagon Receptor-dose Response

Based on the screen in Example 15 above, a subset of human glucagon receptor antisense oligonucleotides were chosen for further study. Dose-response studies were conducted for ISIS 315186, 310457, 315324, 315278, 315181, 315297, 315163 and 310456 in both human HepG2 cell cultures and in cynomolgus monkey primary hepatocytes. These six compounds are homologous to both human and cynomolgus monkey glucagon receptor nucleic acid targets. The universal control ISIS 29848 (NNNNNNNNNNNNNNNNNNNN; SEQ ID NO: 820, where N is an equimolar mixture of A, C, G and T, a chimeric 2' MOE gapmer with a phosphorothioate backbone and with MOEs at positions 1–5 & 16–20) was used as negative control.

The human hepatoblastoma cell line HepG2 was obtained from the American Type Culture Collection (Manassas, Va.). HepG2 cells are routinely cultured in Eagle's MEM supplemented with 10% fetal calf serum, non-essential amino acids, and 1 mM sodium pyruvate (Gibco/Life Technologies, Gaithersburg, Md.). Cells are routinely passaged by trypsinization and dilution when they reach 90% confluence.

Primary cynomolgus monkey hepatocytes were obtained from CellzDirect (Los Angeles) and plated onto collagen-coated 24-well plates (Costar) at a density of 75,000 cells/well. The culturing medium for these hepatocytes was William's E media (Invitrogen) supplemented with 10% FBS (Invitrogen). Cells were allowed to attach overnight and were then treated with oligonucleotide-Lipofectin mixture for 4 hours. The oligonucleotide-Lipofectin mixture was washed off and then cells were incubated in normal medium.

Cells were treated with oligonucleotide for 20 hours at doses of 1, 5, 10, 25, 50, 100 nM for HepG2 cells and 5, 10, 25, 50, 100 and 200 nM for primary monkey hepatocytes (n=3). RNA was analyzed by RT-PCR to determine percent inhibition of glucagon receptor expression compared to control (ISIS 29848), at each oligonucleotide concentration. The results were plotted to give the IC50, the dose of oligonucleotide which results in 50% reduction of glucagon receptor mRNA levels. Results are shown in Table 6.

TABLE 6

IC50s of glucagon receptor antisense oligonucleotides in human HepG2 cells and in cynomolgus monkey primary hepatocytes (in nM)

| ISIS # | SEQ ID NO: | IC50 in human HepG2 cells (nM) | IC50 in monkey hepatocytes (nM) |
|---|---|---|---|
| 315186 | 254 | 5 | 30 |
| 310457 | 184 | 7 | 10 |
| 315324 | 392 | 6 | 19 |
| 315278 | 346 | 8 | 25 |
| 315181 | 249 | 9 | 32 |
| 315297 | 365 | 11 | 11 |
| 315163 | 231 | 19 | 37 |
| 310456 | 183 | 25 | 20 |

Based on these results, three compounds (ISIS 315297, 310457 and 315163) were chosen for study in monkeys.

Example 26

Dose-ranging Study of Antisense Inhibition of Glucagon Receptor Eexpression in Cynomolgus Monkeys A monkey study was performed at SNBL USA, Ltd., Everett, Wash. Forty mature (6–8 years old) male Macaca fascicularis (purpose-bred cynomolgus monkeys) weighing approximately 5–10 kg at the initiation of dosing were used. The animals were individually housed in primary climate-controlled enclosures conforming to the Animal Welfare Act. Animals were offered Purina Mills Laboratory Profiled Fiber Plus® Monkey Diet (Animal Specialties, Hubbard, Oreg.). Occasional fresh fruit and vegetable treats were also offered. Fresh drinking water was available to all animals, ad libitum. Before fasting measurements, food was removed from enclosures between 1630 and 1700 on the afternoon before the scheduled blood draw. After the animals were fasted for at least 16 hours, blood samples for plasma analysis were collected BEFORE dosing or feeding. For fasting analysis, approximately 2.3–2.5 mL of blood was drawn from a peripheral vein. Approximately 1.8 to 2.0 mL was be deposited into a K2-EDTA tube containing DPP-IV inhibitor at 10 μL/mL of blood and trasylol at 250 KIU/mL of blood. Approximately 0.5 mL was deposited into a lithium heparin tube. Once the blood was been deposited into the EDTA plus additives tube, it was inverted to mix and placed on ice within 5 minutes. The blood in the lithium heparin tube was also placed on ice within 5 minutes. Blood samples were centrifuged (2000×g, 15 minutes at 4 to 8° C.) to obtain plasma within 30 minutes of sample collection. The plasma was frozen at or below −70° C. Samples were shipped on dry ice via overnight courier as described below for subsequent analysis.

For non-fasted analysis, the animals were given their AM feeding (between 0830 and 0930) on the day of the blood draw. Ninety minutes after feeding, blood was drawn. The number of biscuits remaining were counted at the time of the blood draw. Samples are prepared and shipped as above.

Monkeys were dosed subcutaneously for 10 weeks with ISIS 315297, ISIS 310457 or ISIS 315163 at three concentrations. In week 1, oligonucleotides were given at 2.0, 5.0 and 20 mg/kg/dose (Day 1, 3 and 5); in week 2 through 10, oligonucleotides were given at 1.0, 2.5 and 10 mg/kg/dose (twice weekly starting at Day 8) The larger dose (6, 15 or 60 mg/kg/week, i.e. 3 injections of 2, 5 or 20 mg/kg) was given in week 1 in order to rapidly achieve the desired steady state oligonucleotide concentration. In week 1, compounds were administered 3 times, every other day; for weeks 2–10, compounds were administered twice per week, with at least 2 days between dosings.

Oligonucleotides were given by subcutaneous (SC) injection, using volumes of 0.1–0.3 ml/kg). For each dosing of each animal, the appropriate volume of the relevant ASO solution or of the control/vehicle article was administered subcutaneously using a syringe and needle (27 G). The total volume of the relevant dosing solution or the control article was calculated on the basis of the animal's most recent body weight. Multiple injection sites on the upper back (intrascapular region) of each monkey were employed. During acclimation the skin of the upper back was be shaved and a clock-like grid (points at 12, 3, 6, and 9 o'clock) was tattooed on each animal. Injection points were a minimum of 5 cm apart. The injection sites were rotated so that each site was used for fourth dose, starting with 12 o'clock and rotating clockwise. The needle was inserted away from the dot and angled so that the dose was deposited underneath the dot.

After the 10 week study (approx. 2 days after last dose), animals were euthanized and three 1 to 4 gram samples of liver tissue were removed and individually snap frozen over liquid nitrogen; alternatively, biopsies could be taken from living animals and frozen. Frozen tissues were homogenized in 4M guanidinium isothiocyanate solution and subjected to CsCl centrifugation (150,000×g for 16 hr at 18° C.). The supernatant was removed and the RNA pellet was resuspended in water, following which it was applied to RNEASY mini columns (Qiagen, Valencia Calif.). After purification and quantitation, the tissues were subjected to RT-PCR analysis as described in previous examples using the following primers and probe:

```
Forward primer—
ACTGCACCCGCAACGC              (SEQ ID NO: 821)

Reverse primer—
CACGGAGCTGGCCTTCAG            (SEQ ID NO: 822)

Probe—
ATCCACGCGAACCTGTTTGTGTCCTT    (SEQ ID NO: 823)
```

RNA amounts were normalized to 18S RNA levels in the tissue. Results are shown in Table 7, as percent reduction in glucagon receptor mRNA in antisense-treated monkeys compared to saline-treated monkeys.

TABLE 7

Glucagon receptor mRNA reduction in monkey liver after treatment with antisense inhibitors of glucagon receptor - RT-PCR expt 1

| ISIS # | SEQ ID NO: | % reduction at 2 mg/kg | % reduction At 5 mg/kg | % reduction at 20 mg/kg |
|---|---|---|---|---|
| 310457 | 184 | 17 | 31 | 64 |
| 315297 | 365 | 2 | 21 | 49 |
| 315163 | 231 | 22 | 18 | 47 |

RNA analysis of the same tissue samples by RT-PCR was repeated independently using the same primer-probe set as above. Results are shown in Table 8 as percent reduction in glucagon receptor mRNA in antisense-treated monkeys compared to saline-treated monkeys.

TABLE 8

Glucagon receptor mRNA reduction in monkey liver after treatment with antisense inhibitors of glucagon receptor-RT-PCR expt 2

| ISIS # | SEQ ID NO: | % reduction at 2 mg/kg | % reduction At 5 mg/kg | % reduction at 20 mg/kg |
|---|---|---|---|---|
| 310457 | 184 | 25 | 23 | 63 |
| 315297 | 365 | 18 | 21 | 56 |
| 315163 | 231 | 25 | 29 | 44 |

The results obtained by RT-PCR were confirmed by Northern blot analysis according to standard methods (Example 14). The cDNA probe that was used for northern blots was a 900-base fragment of monkey GCGR generated by RT-PCR from cynomolgus monkey liver. Results are shown in Table 9.

TABLE 9

Glucagon receptor mRNA reduction in monkey liver after treatment with antisense inhibitors of glucagon receptor-Northern blot

| ISIS # | SEQ ID NO: | % reduction at 2 mg/kg | % reduction At 5 mg/kg | % reduction at 20 mg/kg |
|---|---|---|---|---|
| 310457 | 184 | 8 | 16 | 65 |
| 315297 | 365 | 0 | 10 | 38 |
| 315163 | 231 | 8 | 30 | 27 |

Blood glucose levels were measured in monkeys after treatment with antisense inhibitors of glucagon receptor. Glucose readings were performed using a drop of blood from the blood samples collected as above and read on a One Touch Profile® (Lifescan Inc., a Johnson and Johnson Company). Because normoglycemic (nondiabetic) monkeys were used in this study, no significant changes in blood glucose levels were expected or observed. At no point did animals become hypoglycemic after antisense treatment.

Glucagon levels were measured in plasma of fasted monkeys before (baseline) and after treatment for 5 weeks or 10 weeks with antisense inhibitors of glucagon receptor. Monkeys were anesthetized prior to blood collection to avoid artifacts due to stress. Glucagon levels were determined by radioimmunoassay, ELISA and/or Luminex immunoassay by contract laboratory (Linco, St. Charles Mo.). Results are shown in Table 10.

TABLE 10

Fasted glucagon levels in monkey liver after treatment with antisense inhibitors of glucagon receptor

| ISIS # | SEQ ID NO: | Antisense Dose (mg/kg) | Glucagon (pg/ml) Baseline | Glucagon (pg/ml) Week 5 fasted | Glucagon (pg/ml) Week 10 fasted |
|---|---|---|---|---|---|
| Saline | | | 155 ± 31 | 150 ± 19 | 250 ± 141 |
| 310457 | 184 | 2 | 487 ± 123 | 278 ± 54 | 189 ± 36 |
| | | 5 | 211 ± 25 | 179 ± 55 | 169 ± 26 |
| | | 20 | 308 ± 77 | 580 ± 247 | 1247 ± 451 |
| 315297 | 365 | 2 | 410 ± 94 | 140 ± 42 | 133 ± 26 |
| | | 5 | 519 ± 58 | 193 ± 31 | 204 ± 30 |
| | | 20 | 375 ± 87 | 209 ± 23 | 276 ± 67 |
| 315163 | 231 | 2 | 176 ± 42 | 152 ± 33 | 143 ± 26 |
| | | 5 | 262 ± 76 | 203 ± 74 | 225 ± 95 |
| | | 20 | 251 ± 40 | 257 ± 76 | 421 ± 197 |

Glucagon-likee ptide 1 (GLP-1) levels were measured in plasma of fasted monkeys before (baseline) and after treatment for 5 weeks or 10 weeks with antisense inhibitors of glucagon receptor. Monkeys were anesthetized prior to blood collection to avoid artifacts due to stress. GLP-1 levels were determined by radioimmunoassay, ELISA and/or Luminex immunoasay by contract laboratory (Linco, St. Charle Mo.). Results are shown in Table 11.

TABLE 11

Fasted GLP-1 levels in monkey liver after treatment with antisense inhibitors of glucagon receptor

| ISIS # | SEQ ID NO: | Antisense Dose (mg/kg) | GLP-1 (pM) Baseline | GLP-1 (pM) Week 5 fasted | GLP-1 (pM) Week 10 fasted |
|---|---|---|---|---|---|
| Saline | | | 4 ± 2 | 4 ± 1 | 5 ± 1 |
| 310457 | 184 | 2 | 4 ± 1 | 3 ± 1 | 3 ± .41 |
| | | 5 | 4 ± 1 | 4 ± .48 | 3 ± 1 |
| | | 20 | 8 ± 3 | 17 ± 6 | 30 ± 15 |
| 315297 | 365 | 2 | 3 ± 1 | 3 ± 1 | 3 ± .29 |
| | | 5 | 4 ± 1 | 4 ± 1 | 4 ± 2 |
| | | 20 | 11 ± 8 | 9 ± 4 | 7 ± 5 |
| 315163 | 231 | 2 | 4 ± 1 | 4 ± 1 | 4 ± 1 |
| | | 5 | 3 ± 1 | 5 ± 2 | 3 ± 1 |
| | | 20 | 2 ± 0 | 4 ± .48 | 5 ± 1 |

What is claimed is:

1. A compound 12 to 50 nucleobases in length targeted to a nucleic acid molecule encoding human glucagon receptor, wherein said compound has at least 90% complementarity with a nucleic acid molecule of SEQ ID NO: 4 encoding human glucagon receptor, and wherein said compound comprises at least an 8-nucleobase portion of SEQ ID NO: 184.

2. The compound of claim 1 which has at least 95% complementarity with a nucleic acid molecule of SEQ ID NO: 4 encoding human glucagon receptor.

3. The compound of claim 1 which consists of SEQ ID NO: 184.

4. The compound of claim 1 which is 15 to 30 nucleobases in length.

5. The compound of claim 1 which is 20 nucleobases in length.

6. The compound of claim 1 comprising an oligonucleotide.

7. The compound of claim 6 comprising a DNA oligonucleotide.

8. The compound of claim 6 comprising an RNA oligonucleotide.

9. The compound of claim 6 comprising a chimeric oligonucleotide.

10. The compound of claim 6 wherein at least a portion of said compound hybridizes with RNA to form an oligonucleotide-RNA duplex.

11. The compound of claim 6 wherein the oligonucleotide is single-stranded.

12. The compound of claim 1 having at least one modified internucleoside linkage, sugar moiety, or nucleobase.

13. The compound of claim 12 having at least one 2'-O-methoxyethyl sugar moiety.

14. The compound of claim 12 having at least one phosphorothioate internucleoside linkage.

15. The compound of claim 12 having at least one 5-methylcytosine.

16. A kit or assay device-comprising the compound of claim 1.

17. A compound comprising SEQ ID NO: 184 wherein, every internucleoside linkage is a phosphorothioate linkage, nucleobases 1–5 and 16–20 comprise a 2-O-methoxyethyl modification and every cytosine residue comprises a 5-methyl modification, or a pharmaceutically acceptable salt thereof.

18. The compound of claim 17 wherein the compound is a sodium salt.

19. A pharmaceutical composition comprising the compound of claim 17 and a pharmaceutical carrier, diluent or excipient.

20. Pharmaceutical composition comprising the compound of claim 1 and a pharmaceutically acceptable diluent or carrier.

21. The composition of claim 20 comprising a colloidal dispersion system.

22. A compound comprising the nucleobase sequence of SEQ ID NO: 184 having at least one chemical modification.

23. The compound of claim 22 having at least one modified internucleoside linkage, sugar moiety, or nucleobase.

24. The compound of claim 22 having at least one 2'-O-methoxyethyl sugar moiety.

25. The compound of claim 22 having at least one phosphorothioate internucleoside linkage.

26. The compound of claim 22 having at least one 5-methylcytosine.

* * * * *

UNITED STATES PATENT AND TRADEMARK OFFICE

CERTIFICATE OF CORRECTION

PATENT NO. : 7,399,853 B2
APPLICATION NO. : 10/832777
DATED : July 15, 2008
INVENTOR(S) : Freier et al.

It is certified that error appears in the above-identified patent and that said Letters Patent is hereby corrected as shown below:

In claim 17, col. 400 line 9 the following error appears in the text of the claim "2-O-methoxyethyl"

The correct text should read -- 2'-O-methoxyethyl --

Signed and Sealed this

Fourteenth Day of October, 2008

JON W. DUDAS
*Director of the United States Patent and Trademark Office*

SEQUENCE LISTING

```
<160> NUMBER OF SEQ ID NOS: 823

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide
```

-continued

<400> SEQUENCE: 1

```
tccgtcatcg ctcctcaggg                                                   20


<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2

gtgcgcgcga gcccgaaatc                                                   20


<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3

atgcattctg cccccaagga                                                   20


<210> SEQ ID NO 4
<211> LENGTH: 2034
<212> TYPE: DNA
<213> ORGANISM: H. sapiens
<220> FEATURE:
<220> FEATURE:
<221> NAME/KEY: CDS
<222> LOCATION: (278)...(1711)

<400> SEQUENCE: 4

ggatctggca gcgccgcgaa gacgagcggt caccggcgcc cgacccgagc gcgcccagag      60

gacggcgggg agccaagccg acccccgagc agcgccgcgc gggccctgag gctcaaaggg     120

gcagcttcag gggaggacac cccactggcc aggacgcccc aggctctgct gctctgccac     180

tcagctgccc tcggaggagc gtacacacac accaggactg cattgcccca gtgtgcagcc     240

cctgccagat gtgggaggca gctagctgcc cagaggc atg ccc ccc tgc cag cca      295
                                         Met Pro Pro Cys Gln Pro
                                          1               5

cag cga ccc ctg ctg ctg ttg ctg ctg ctg ctg gcc tgc cag cca cag      343
Gln Arg Pro Leu Leu Leu Leu Leu Leu Leu Leu Ala Cys Gln Pro Gln
            10                  15                  20

gtc ccc tcc gct cag gtg atg gac ttc ctg ttt gag aag tgg aag ctc      391
Val Pro Ser Ala Gln Val Met Asp Phe Leu Phe Glu Lys Trp Lys Leu
        25                  30                  35

tac ggt gac cag tgt cac cac aac ctg agc ctg ctg ccc cct ccc acg      439
Tyr Gly Asp Gln Cys His His Asn Leu Ser Leu Leu Pro Pro Pro Thr
    40                  45                  50

gag ctg gtg tgc aac aga acc ttc gac aag tat tcc tgc tgg ccg gac      487
Glu Leu Val Cys Asn Arg Thr Phe Asp Lys Tyr Ser Cys Trp Pro Asp
 55                  60                  65                  70

acc ccc gcc aat acc acg gcc aac atc tcc tgc ccc tgg tac ctg cct      535
Thr Pro Ala Asn Thr Thr Ala Asn Ile Ser Cys Pro Trp Tyr Leu Pro
                75                  80                  85

tgg cac cac aaa gtg caa cac cgc ttc gtg ttc aag aga tgc ggg ccc      583
Trp His His Lys Val Gln His Arg Phe Val Phe Lys Arg Cys Gly Pro
            90                  95                 100

gac ggt cag tgg gtg cgt gga ccc cgg ggg cag cct tgg cgt gat gcc      631
Asp Gly Gln Trp Val Arg Gly Pro Arg Gly Gln Pro Trp Arg Asp Ala
        105                 110                 115
```

-continued

```
tcc cag tgc cag atg gat ggc gag gag att gag gtc cag aag gag gtg      679
Ser Gln Cys Gln Met Asp Gly Glu Glu Ile Glu Val Gln Lys Glu Val
    120                 125                 130

gcc aag atg tac agc agc ttc cag gtg atg tac aca gtg ggc tac agc      727
Ala Lys Met Tyr Ser Ser Phe Gln Val Met Tyr Thr Val Gly Tyr Ser
135                 140                 145                 150

ctg tcc ctg ggg gcc ctg ctc ctc gcc ttg gcc atc ctg ggg ggc ctc      775
Leu Ser Leu Gly Ala Leu Leu Leu Ala Leu Ala Ile Leu Gly Gly Leu
                155                 160                 165

agc aag ctg cac tgc acc cgc aat gcc atc cac gcg aat ctg ttt gcg      823
Ser Lys Leu His Cys Thr Arg Asn Ala Ile His Ala Asn Leu Phe Ala
            170                 175                 180

tcc ttc gtg ctg aaa gcc agc tcc gtg ctg gtc att gat ggg ctg ctc      871
Ser Phe Val Leu Lys Ala Ser Ser Val Leu Val Ile Asp Gly Leu Leu
        185                 190                 195

agg acc cgc tac agc cag aaa att ggc gac gac ctc agt gtc agc acc      919
Arg Thr Arg Tyr Ser Gln Lys Ile Gly Asp Asp Leu Ser Val Ser Thr
    200                 205                 210

tgg ctc agt gat gga gcg gtg gct ggc tgc cgt gtg gcc gcg gtg ttc      967
Trp Leu Ser Asp Gly Ala Val Ala Gly Cys Arg Val Ala Ala Val Phe
215                 220                 225                 230

atg caa tat ggc atc gtg gcc aac tac tgc tgg ctg ctg gtg gag ggc     1015
Met Gln Tyr Gly Ile Val Ala Asn Tyr Cys Trp Leu Leu Val Glu Gly
                235                 240                 245

ctg tac ctg cac aac ctg ctg ggc ctg gcc acc ctc ccc gag agg agc     1063
Leu Tyr Leu His Asn Leu Leu Gly Leu Ala Thr Leu Pro Glu Arg Ser
            250                 255                 260

ttc ttc agc ctc tac ctg ggc atc ggc tgg ggt gcc ccc atg ctg ttc     1111
Phe Phe Ser Leu Tyr Leu Gly Ile Gly Trp Gly Ala Pro Met Leu Phe
        265                 270                 275

gtc gtc ccc tgg gca gtg gtc aag tgt ctg ttc gag aac gtc cag tgc     1159
Val Val Pro Trp Ala Val Val Lys Cys Leu Phe Glu Asn Val Gln Cys
    280                 285                 290

tgg acc agc aat gac aac atg ggc ttc tgg tgg atc ctg cgg ttc ccc     1207
Trp Thr Ser Asn Asp Asn Met Gly Phe Trp Trp Ile Leu Arg Phe Pro
295                 300                 305                 310

gtc ttc ctg gcc atc ctg atc aac ttc ttc atc ttc gtc cgc atc gtt     1255
Val Phe Leu Ala Ile Leu Ile Asn Phe Phe Ile Phe Val Arg Ile Val
                315                 320                 325

cag ctg ctc gtg gcc aag ctg cgg gca cgg cag atg cac cac aca gac     1303
Gln Leu Leu Val Ala Lys Leu Arg Ala Arg Gln Met His His Thr Asp
            330                 335                 340

tac aag ttc cgg ctg gcc aag tcc acg ctg acc ctc atc cct ctg ctg     1351
Tyr Lys Phe Arg Leu Ala Lys Ser Thr Leu Thr Leu Ile Pro Leu Leu
        345                 350                 355

ggc gtc cac gaa gtg gtc ttt gcc ttc gtg acg gac gag cac gcc cag     1399
Gly Val His Glu Val Val Phe Ala Phe Val Thr Asp Glu His Ala Gln
    360                 365                 370

ggc acc ctg cgc tcc gcc aag ctc ttc ttc gac ctc ttc ctc agc tcc     1447
Gly Thr Leu Arg Ser Ala Lys Leu Phe Phe Asp Leu Phe Leu Ser Ser
375                 380                 385                 390

ttc cag ggc ctg ctg gtg gct gtc ctc tac tgc ttc ctc aac aag gag     1495
Phe Gln Gly Leu Leu Val Ala Val Leu Tyr Cys Phe Leu Asn Lys Glu
                395                 400                 405

gtg cag tcg gag ctg cgg cgg cgt tgg cac cgc tgg cgc ctg ggc aaa     1543
Val Gln Ser Glu Leu Arg Arg Arg Trp His Arg Trp Arg Leu Gly Lys
            410                 415                 420

gtg cta tgg gag gag cgg aac acc agc aac cac agg gcc tca tct tcg     1591
Val Leu Trp Glu Glu Arg Asn Thr Ser Asn His Arg Ala Ser Ser Ser
```

-continued

```
        425                 430                 435

ccc ggc cac ggc cct ccc agc aag gag ctg cag ttt ggg agg ggt ggt     1639
Pro Gly His Gly Pro Pro Ser Lys Glu Leu Gln Phe Gly Arg Gly Gly
    440                 445                 450

ggc agc cag gat tca tct gcg gag acc ccc ttg gct ggt ggc ctc cct     1687
Gly Ser Gln Asp Ser Ser Ala Glu Thr Pro Leu Ala Gly Gly Leu Pro
455                 460                 465                 470

aga ttg gct gag agc ccc ttc tga accctgctgg gaccccagct agggctggac    1741
Arg Leu Ala Glu Ser Pro Phe
                475

tctggcaccc agaggcgtcg ctggacaacc cagaactgga cgcccagctg aggctggggg   1801

cgggggagcc aacagcagcc cccacctacc ccccaccccc agtgtggctg tctgcgagat   1861

tgggcctcct ctccctgcac ctgccttgtc cctggtgcag aggtgagcag aggagtccag   1921

ggcgggagtg ggggctgtgc cgtgaactgc gtgccagtgt ccccacgtat gtcggcacgt   1981

cccatgtgca tggaaatgtc ctccaacaat aaagagctca agtggtcacc gtg          2034
```

<210> SEQ ID NO 5
<211> LENGTH: 18
<212> TYPE: DNA
<213> ORGANISM: Artificial Sequence
<220> FEATURE:
<223> OTHER INFORMATION: PCR Primer

<400> SEQUENCE: 5 gacaccccg ccaatacc 18

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
ccgcatctct tgaacacgaa 20

<210> SEQ ID NO 7
<211> LENGTH: 15
<212> TYPE: DNA
<213> ORGANISM: Artificial Sequence
<220> FEATURE:
<223> OTHER INFORMATION: PCR Probe

<400> SEQUENCE: 7
ttggcaccac aaagt 15

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc 19

<210> SEQ ID NO 9
<211> LENGTH: 20
<212> TYPE: DNA
<213> ORGANISM: Artificial Sequence
<220> FEATURE:
<223> OTHER INFORMATION: PCR Primer -continued

<400> SEQUENCE: 9

```
gaagatggtg atgggatttc                                                20
```

```
<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10

caagcttccc gttctcagcc                                                20


<210> SEQ ID NO 11
<211> LENGTH: 1944
<212> TYPE: DNA
<213> ORGANISM: M. musculus
<220> FEATURE:
<220> FEATURE:
<221> NAME/KEY: CDS
<222> LOCATION: (95)...(1552)

<400> SEQUENCE: 11

cagggtctcc cttgcaacct gaggagaggt gcacacactc tgaggaccta ggtgtgcaac     60

ctctgccaga tgtggggcgt ggctacccag aggc atg ccc ctc acc cag ctc cac    115
                                      Met Pro Leu Thr Gln Leu His
                                        1               5

tgt ccc cac ctg ctg ctg ctg ctg ttg gtg ctg tca tgt ctg cca gag      163
Cys Pro His Leu Leu Leu Leu Leu Leu Val Leu Ser Cys Leu Pro Glu
         10                  15                  20

gca ccc tct gcc cag gta atg gac ttt ttg ttt gag aag tgg aag ctc      211
Ala Pro Ser Ala Gln Val Met Asp Phe Leu Phe Glu Lys Trp Lys Leu
     25                  30                  35

tat agt gac caa tgt cac cac aac cta agc ctg ctg ccc cca cct act      259
Tyr Ser Asp Gln Cys His His Asn Leu Ser Leu Leu Pro Pro Pro Thr
 40                  45                  50                  55

gag ctg gtc tgt aac aga acc ttc gac aac tac tcc tgc tgg cct gac      307
Glu Leu Val Cys Asn Arg Thr Phe Asp Asn Tyr Ser Cys Trp Pro Asp
                 60                  65                  70

acc cct ccc aac acc act gcc aac att tcc tgc ccc tgg tac cta cct      355
Thr Pro Pro Asn Thr Thr Ala Asn Ile Ser Cys Pro Trp Tyr Leu Pro
             75                  80                  85

tgg tgc cac aaa gtg cag cac cgc cta gtg ttc aag agg tgt ggg ccc      403
Trp Cys His Lys Val Gln His Arg Leu Val Phe Lys Arg Cys Gly Pro
         90                  95                 100

gat ggg cag tgg gtt cga ggg cca cgg ggg cag ccg tgg cgc aac gcc      451
Asp Gly Gln Trp Val Arg Gly Pro Arg Gly Gln Pro Trp Arg Asn Ala
    105                 110                 115

tcc caa tgt cag ttg gat gat gaa gag atc gag gtc cag aag ggg gtg      499
Ser Gln Cys Gln Leu Asp Asp Glu Glu Ile Glu Val Gln Lys Gly Val
120                 125                 130                 135

gcc aag atg tat agc agc cag cag gtg atg tac acc gtg ggc tac agt      547
Ala Lys Met Tyr Ser Ser Gln Gln Val Met Tyr Thr Val Gly Tyr Ser
                140                 145                 150

ctg tcc ctg ggg gcc ttg ctc ctt gcg ctg gtc atc ctg ctg ggc ctc      595
Leu Ser Leu Gly Ala Leu Leu Leu Ala Leu Val Ile Leu Leu Gly Leu
            155                 160                 165

agg aag ctg cac tgc acc cga aac tac atc cat ggg aac ctg ttt gcg      643
Arg Lys Leu His Cys Thr Arg Asn Tyr Ile His Gly Asn Leu Phe Ala
        170                 175                 180
```

-continued

```
tcc ttt gtg ctc aag gct ggc tct gtg ttg gtc atc gat tgg ctg ctg      691
Ser Phe Val Leu Lys Ala Gly Ser Val Leu Val Ile Asp Trp Leu Leu
    185                 190                 195

aag aca cgg tac agc cag aag att ggc gat gac ctc agt gtg agc gtc      739
Lys Thr Arg Tyr Ser Gln Lys Ile Gly Asp Asp Leu Ser Val Ser Val
200                 205                 210                 215

tgg ctc agt gac ggg gcg atg gcc ggc tgc aga gtg gcc aca gtg atc      787
Trp Leu Ser Asp Gly Ala Met Ala Gly Cys Arg Val Ala Thr Val Ile
                220                 225                 230

atg cag tac ggc atc ata ccc aac tat tgc tgg ttg ctg gta gag ggc      835
Met Gln Tyr Gly Ile Ile Pro Asn Tyr Cys Trp Leu Leu Val Glu Gly
            235                 240                 245

gtg tac ctg tac agc ctg ctg agc ctt gcc acc ttc tct gag agg agc      883
Val Tyr Leu Tyr Ser Leu Leu Ser Leu Ala Thr Phe Ser Glu Arg Ser
        250                 255                 260

ttc ttt tcc ctc tac ctg ggc att ggc tgg ggt gcg ccc ctg ctg ttt      931
Phe Phe Ser Leu Tyr Leu Gly Ile Gly Trp Gly Ala Pro Leu Leu Phe
    265                 270                 275

gtc atc ccc tgg gtg gtg gtc aag tgt ctg ttt gag aat gtt cag tgc      979
Val Ile Pro Trp Val Val Val Lys Cys Leu Phe Glu Asn Val Gln Cys
280                 285                 290                 295

tgg acc agc aat gac aac atg gga ttc tgg tgg atc ctg cgt att cct     1027
Trp Thr Ser Asn Asp Asn Met Gly Phe Trp Trp Ile Leu Arg Ile Pro
                300                 305                 310

gtc ttc ctg gcc tta ctg atc aat ttt ttc atc ttt gtc cac atc att     1075
Val Phe Leu Ala Leu Leu Ile Asn Phe Phe Ile Phe Val His Ile Ile
            315                 320                 325

caa ctt ctt gtg gcc aag ctg cgt gcc cat cag atg cac tat gct gat     1123
Gln Leu Leu Val Ala Lys Leu Arg Ala His Gln Met His Tyr Ala Asp
        330                 335                 340

tac aag ttc cgg ctg gcc agg tcc acg ctg acc ctc atc cct ctg ctg     1171
Tyr Lys Phe Arg Leu Ala Arg Ser Thr Leu Thr Leu Ile Pro Leu Leu
    345                 350                 355

ggg gtc cac gag gtg gtc ttt gcc ttt gtg act gac gag cat gcc caa     1219
Gly Val His Glu Val Val Phe Ala Phe Val Thr Asp Glu His Ala Gln
360                 365                 370                 375

ggc acc ctg cgc tcc acc aag ctc ttt ttt gac ctg ttc ctc agc tcc     1267
Gly Thr Leu Arg Ser Thr Lys Leu Phe Phe Asp Leu Phe Leu Ser Ser
                380                 385                 390

ttc cag ggt ctg ctg gtg gct gtt ctc tac tgt ttc ctc aac aag gag     1315
Phe Gln Gly Leu Leu Val Ala Val Leu Tyr Cys Phe Leu Asn Lys Glu
            395                 400                 405

gtg cag gca gag ctg atg cgg cgt tgg agg caa tgg caa gaa ggc aaa     1363
Val Gln Ala Glu Leu Met Arg Arg Trp Arg Gln Trp Gln Glu Gly Lys
        410                 415                 420

gct ctt cag gag gaa agg ttg gcc agc agc cat ggc agc cac atg gcc     1411
Ala Leu Gln Glu Glu Arg Leu Ala Ser Ser His Gly Ser His Met Ala
    425                 430                 435

cca gca ggg cct tgt cat ggt gat ccc tgt gag aaa ctt cag ctt atg     1459
Pro Ala Gly Pro Cys His Gly Asp Pro Cys Glu Lys Leu Gln Leu Met
440                 445                 450                 455

agt gca ggc agc agc agt ggg act ggc tgt gtg ccc tct atg gag acc     1507
Ser Ala Gly Ser Ser Ser Gly Thr Gly Cys Val Pro Ser Met Glu Thr
                460                 465                 470

tcg ctg gcc agt agt ctc cca agg ttg gct gac agc ccc acc tga         1552
Ser Leu Ala Ser Ser Leu Pro Arg Leu Ala Asp Ser Pro Thr
            475                 480                 485

atctccactt ggagcctagg caggttgtgt tcaagaaagg gcctcagagg acaacccaga   1612

gccagatgcc cggccaaggt tgaagagcca aagcagcaag acagcagctt gtactgtgca   1672
```

-continued

```
cactccccta acctgtccta gcctggcaca ggccacagtg acagagtagg ggttggatat   1732

gatggagaag ccatgttatc tatgaactct gagtgttccc atgtgtgttg acatggtccc   1792

tgtacccaga tatgtccttc agtaaaaagc tcgagtggag ctgctgcaca gctcgtggac   1852

agcaggcttg aagcccccag ggacggggtt tgggaggccg gggatgagca gcacactcag   1912

caggtggagc gctagtgcaa cccaggaaag aa                                  1944


<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12

atttcctgcc cctggtacct                                                  20


<210> SEQ ID NO 13
<211> LENGTH: 17
<212> TYPE: DNA
<213> ORGANISM: Artificial Sequence
<220> FEATURE:
<223> OTHER INFORMATION: PCR Primer

<400> SEQUENCE: 13

cgggcccaca cctcttg                                                     17


<210> SEQ ID NO 14
<211> LENGTH: 26
<212> TYPE: DNA
<213> ORGANISM: Artificial Sequence
<220> FEATURE:
<223> OTHER INFORMATION: PCR Probe

<400> SEQUENCE: 14

ccacaaagtg cagcaccgcc tagtgt                                           26


<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15

ggcaaattca acggcacagt                                                  20


<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16

gggtctcgct cctggaagat                                                  20


<210> SEQ ID NO 17
<211> LENGTH: 27
<212> TYPE: DNA
<213> ORGANISM: Artificial Sequence
<220> FEATURE:
<223> OTHER INFORMATION: PCR Probe
```

-continued

<400> SEQUENCE: 17
aaggccgaga atgggaagct tgtcatc 27

<210> SEQ ID NO 18
<211> LENGTH: 25138
<212> TYPE: DNA
<213> ORGANISM: H. sapiens
<220> FEATURE:
<221> NAME/KEY: unsure
<222> LOCATION: 4663
<223> OTHER INFORMATION: unknown
<220> FEATURE:
<221> NAME/KEY: unsure
<222> LOCATION: 4664
<223> OTHER INFORMATION: unknown
<220> FEATURE:
<221> NAME/KEY: unsure
<222> LOCATION: 4665
<223> OTHER INFORMATION: unknown
<220> FEATURE:
<221> NAME/KEY: unsure
<222> LOCATION: 4666
<223> OTHER INFORMATION: unknown
<220> FEATURE:
<221> NAME/KEY: unsure
<222> LOCATION: 4667
<223> OTHER INFORMATION: unknown
<220> FEATURE:
<221> NAME/KEY: unsure
<222> LOCATION: 4668
<223> OTHER INFORMATION: unknown
<220> FEATURE:
<221> NAME/KEY: unsure
<222> LOCATION: 4669
<223> OTHER INFORMATION: unknown
<220> FEATURE:
<221> NAME/KEY: unsure
<222> LOCATION: 4670
<223> OTHER INFORMATION: unknown
<220> FEATURE:
<221> NAME/KEY: unsure
<222> LOCATION: 4671
<223> OTHER INFORMATION: unknown
<220> FEATURE:
<221> NAME/KEY: unsure
<222> LOCATION: 4672
<223> OTHER INFORMATION: unknown
<220> FEATURE:
<221> NAME/KEY: unsure
<222> LOCATION: 4673
<223> OTHER INFORMATION: unknown
<220> FEATURE:
<221> NAME/KEY: unsure
<222> LOCATION: 4674
<223> OTHER INFORMATION: unknown
<220> FEATURE:
<221> NAME/KEY: unsure
<222> LOCATION: 4675
<223> OTHER INFORMATION: unknown
<220> FEATURE:
<221> NAME/KEY: unsure
<222> LOCATION: 4676
<223> OTHER INFORMATION: unknown
<220> FEATURE:
<221> NAME/KEY: unsure
<222> LOCATION: 4677
<223> OTHER INFORMATION: unknown
<220> FEATURE:
<221> NAME/KEY: unsure
<222> LOCATION: 4678
<223> OTHER INFORMATION: unknown
<220> FEATURE:
<221> NAME/KEY: unsure
<222> LOCATION: 4679
<223> OTHER INFORMATION: unknown
<220> FEATURE:
<221> NAME/KEY: unsure -continued
<222> LOCATION: 4680
<223> OTHER INFORMATION: unknown
<220> FEATURE:
<221> NAME/KEY: unsure
<222> LOCATION: 4681
<223> OTHER INFORMATION: unknown
<220> FEATURE:
<221> NAME/KEY: unsure
<222> LOCATION: 4682
<223> OTHER INFORMATION: unknown
<220> FEATURE:
<221> NAME/KEY: unsure
<222> LOCATION: 4683
<223> OTHER INFORMATION: unknown
<220> FEATURE:
<221> NAME/KEY: unsure
<222> LOCATION: 4684
<223> OTHER INFORMATION: unknown
<220> FEATURE:
<221> NAME/KEY: unsure
<222> LOCATION: 4685
<223> OTHER INFORMATION: unknown
<220> FEATURE:
<221> NAME/KEY: unsure
<222> LOCATION: 4686
<223> OTHER INFORMATION: unknown
<220> FEATURE:
<221> NAME/KEY: unsure
<222> LOCATION: 4687
<223> OTHER INFORMATION: unknown
<220> FEATURE:
<221> NAME/KEY: unsure
<222> LOCATION: 4688
<223> OTHER INFORMATION: unknown
<220> FEATURE:
<221> NAME/KEY: unsure
<222> LOCATION: 4689
<223> OTHER INFORMATION: unknown
<220> FEATURE:
<221> NAME/KEY: unsure
<222> LOCATION: 4690
<223> OTHER INFORMATION: unknown
<220> FEATURE:
<221> NAME/KEY: unsure
<222> LOCATION: 4691
<223> OTHER INFORMATION: unknown
<220> FEATURE:
<221> NAME/KEY: unsure
<222> LOCATION: 4692
<223> OTHER INFORMATION: unknown
<220> FEATURE:
<221> NAME/KEY: unsure
<222> LOCATION: 4693
<223> OTHER INFORMATION: unknown
<220> FEATURE:
<221> NAME/KEY: unsure
<222> LOCATION: 4694
<223> OTHER INFORMATION: unknown
<220> FEATURE:
<221> NAME/KEY: unsure
<222> LOCATION: 4695
<223> OTHER INFORMATION: unknown
<220> FEATURE:
<221> NAME/KEY: unsure
<222> LOCATION: 4696
<223> OTHER INFORMATION: unknown
<220> FEATURE:
<221> NAME/KEY: unsure
<222> LOCATION: 4697
<223> OTHER INFORMATION: unknown
<220> FEATURE:
<221> NAME/KEY: unsure
<222> LOCATION: 4698
<223> OTHER INFORMATION: unknown
<220> FEATURE:
<221> NAME/KEY: unsure
<222> LOCATION: 4699
<223> OTHER INFORMATION: unknown
<220> FEATURE:

-continued

<221> NAME/KEY: unsure
<222> LOCATION: 4700
<223> OTHER INFORMATION: unknown
<220> FEATURE:
<221> NAME/KEY: unsure
<222> LOCATION: 4701
<223> OTHER INFORMATION: unknown
<220> FEATURE:
<221> NAME/KEY: unsure
<222> LOCATION: 4702
<223> OTHER INFORMATION: unknown
<220> FEATURE:
<221> NAME/KEY: unsure
<222> LOCATION: 4703
<223> OTHER INFORMATION: unknown
<220> FEATURE:
<221> NAME/KEY: unsure
<222> LOCATION: 4704
<223> OTHER INFORMATION: unknown
<220> FEATURE:
<221> NAME/KEY: unsure
<222> LOCATION: 4705
<223> OTHER INFORMATION: unknown
<220> FEATURE:
<221> NAME/KEY: unsure
<222> LOCATION: 4706
<223> OTHER INFORMATION: unknown
<220> FEATURE:
<221> NAME/KEY: unsure
<222> LOCATION: 4707
<223> OTHER INFORMATION: unknown
<220> FEATURE:
<221> NAME/KEY: unsure
<222> LOCATION: 4708
<223> OTHER INFORMATION: unknown
<220> FEATURE:
<221> NAME/KEY: unsure
<222> LOCATION: 4709
<223> OTHER INFORMATION: unknown
<220> FEATURE:
<221> NAME/KEY: unsure
<222> LOCATION: 4710
<223> OTHER INFORMATION: unknown
<220> FEATURE:
<221> NAME/KEY: unsure
<222> LOCATION: 4711
<223> OTHER INFORMATION: unknown
<220> FEATURE:
<221> NAME/KEY: unsure
<222> LOCATION: 4712
<223> OTHER INFORMATION: unknown
<220> FEATURE:
<221> NAME/KEY: unsure
<222> LOCATION: 4713
<223> OTHER INFORMATION: unknown
<220> FEATURE:
<221> NAME/KEY: unsure
<222> LOCATION: 4714
<223> OTHER INFORMATION: unknown
<220> FEATURE:
<221> NAME/KEY: unsure
<222> LOCATION: 4715
<223> OTHER INFORMATION: unknown
<220> FEATURE:
<221> NAME/KEY: unsure
<222> LOCATION: 4716
<223> OTHER INFORMATION: unknown
<220> FEATURE:
<221> NAME/KEY: unsure
<222> LOCATION: 4717
<223> OTHER INFORMATION: unknown
<220> FEATURE:
<221> NAME/KEY: unsure
<222> LOCATION: 4718
<223> OTHER INFORMATION: unknown
<220> FEATURE:
<221> NAME/KEY: unsure
<222> LOCATION: 4719
<223> OTHER INFORMATION: unknown -continued
<220> FEATURE:
<221> NAME/KEY: unsure
<222> LOCATION: 4720
<223> OTHER INFORMATION: unknown
<220> FEATURE:
<221> NAME/KEY: unsure
<222> LOCATION: 4721
<223> OTHER INFORMATION: unknown
<220> FEATURE:
<221> NAME/KEY: unsure
<222> LOCATION: 4722
<223> OTHER INFORMATION: unknown
<220> FEATURE:
<221> NAME/KEY: unsure
<222> LOCATION: 4723
<223> OTHER INFORMATION: unknown
<220> FEATURE:
<221> NAME/KEY: unsure
<222> LOCATION: 4724
<223> OTHER INFORMATION: unknown
<220> FEATURE:
<221> NAME/KEY: unsure
<222> LOCATION: 4725
<223> OTHER INFORMATION: unknown
<220> FEATURE:
<221> NAME/KEY: unsure
<222> LOCATION: 4726
<223> OTHER INFORMATION: unknown
<220> FEATURE:
<221> NAME/KEY: unsure
<222> LOCATION: 4727
<223> OTHER INFORMATION: unknown
<220> FEATURE:
<221> NAME/KEY: unsure
<222> LOCATION: 4728
<223> OTHER INFORMATION: unknown
<220> FEATURE:
<221> NAME/KEY: unsure
<222> LOCATION: 4729
<223> OTHER INFORMATION: unknown
<220> FEATURE:
<221> NAME/KEY: unsure
<222> LOCATION: 4730
<223> OTHER INFORMATION: unknown
<220> FEATURE:
<221> NAME/KEY: unsure
<222> LOCATION: 4731
<223> OTHER INFORMATION: unknown
<220> FEATURE:
<221> NAME/KEY: unsure
<222> LOCATION: 4732
<223> OTHER INFORMATION: unknown
<220> FEATURE:
<221> NAME/KEY: unsure
<222> LOCATION: 4733
<223> OTHER INFORMATION: unknown
<220> FEATURE:
<221> NAME/KEY: unsure
<222> LOCATION: 4734
<223> OTHER INFORMATION: unknown
<220> FEATURE:
<221> NAME/KEY: unsure
<222> LOCATION: 4735
<223> OTHER INFORMATION: unknown
<220> FEATURE:
<221> NAME/KEY: unsure
<222> LOCATION: 4736
<223> OTHER INFORMATION: unknown
<220> FEATURE:
<221> NAME/KEY: unsure
<222> LOCATION: 4737
<223> OTHER INFORMATION: unknown
<220> FEATURE:
<221> NAME/KEY: unsure
<222> LOCATION: 4738
<223> OTHER INFORMATION: unknown
<220> FEATURE:
<221> NAME/KEY: unsure
<222> LOCATION: 4739

-continued

<223> OTHER INFORMATION: unknown
<220> FEATURE:
<221> NAME/KEY: unsure
<222> LOCATION: 4740
<223> OTHER INFORMATION: unknown
<220> FEATURE:
<221> NAME/KEY: unsure
<222> LOCATION: 4741
<223> OTHER INFORMATION: unknown
<220> FEATURE:
<221> NAME/KEY: unsure
<222> LOCATION: 4742
<223> OTHER INFORMATION: unknown
<220> FEATURE:
<221> NAME/KEY: unsure
<222> LOCATION: 4743
<223> OTHER INFORMATION: unknown
<220> FEATURE:
<221> NAME/KEY: unsure
<222> LOCATION: 4744
<223> OTHER INFORMATION: unknown
<220> FEATURE:
<221> NAME/KEY: unsure
<222> LOCATION: 4745
<223> OTHER INFORMATION: unknown
<220> FEATURE:
<221> NAME/KEY: unsure
<222> LOCATION: 4746
<223> OTHER INFORMATION: unknown
<220> FEATURE:
<221> NAME/KEY: unsure
<222> LOCATION: 4747
<223> OTHER INFORMATION: unknown
<220> FEATURE:
<221> NAME/KEY: unsure
<222> LOCATION: 4748
<223> OTHER INFORMATION: unknown
<220> FEATURE:
<221> NAME/KEY: unsure
<222> LOCATION: 4749
<223> OTHER INFORMATION: unknown
<220> FEATURE:
<221> NAME/KEY: unsure
<222> LOCATION: 4750
<223> OTHER INFORMATION: unknown
<220> FEATURE:
<221> NAME/KEY: unsure
<222> LOCATION: 4751
<223> OTHER INFORMATION: unknown
<220> FEATURE:
<221> NAME/KEY: unsure
<222> LOCATION: 4752
<223> OTHER INFORMATION: unknown
<220> FEATURE:
<221> NAME/KEY: unsure
<222> LOCATION: 4753
<223> OTHER INFORMATION: unknown
<220> FEATURE:
<221> NAME/KEY: unsure
<222> LOCATION: 4754
<223> OTHER INFORMATION: unknown
<220> FEATURE:
<221> NAME/KEY: unsure
<222> LOCATION: 4755
<223> OTHER INFORMATION: unknown
<220> FEATURE:
<221> NAME/KEY: unsure
<222> LOCATION: 4756
<223> OTHER INFORMATION: unknown
<220> FEATURE:
<221> NAME/KEY: unsure
<222> LOCATION: 4757
<223> OTHER INFORMATION: unknown
<220> FEATURE:
<221> NAME/KEY: unsure
<222> LOCATION: 4758
<223> OTHER INFORMATION: unknown
<220> FEATURE:
<221> NAME/KEY: unsure -continued
<222> LOCATION: 4759
<223> OTHER INFORMATION: unknown
<220> FEATURE:
<221> NAME/KEY: unsure
<222> LOCATION: 4760
<223> OTHER INFORMATION: unknown
<220> FEATURE:
<221> NAME/KEY: unsure
<222> LOCATION: 4761
<223> OTHER INFORMATION: unknown
<220> FEATURE:
<221> NAME/KEY: unsure
<222> LOCATION: 4762
<223> OTHER INFORMATION: unknown
<220> FEATURE:
<221> NAME/KEY: unsure
<222> LOCATION: 9698
<223> OTHER INFORMATION: unknown
<220> FEATURE:
<221> NAME/KEY: unsure
<222> LOCATION: 15898
<223> OTHER INFORMATION: unknown
<220> FEATURE:
<221> NAME/KEY: unsure
<222> LOCATION: 15899
<223> OTHER INFORMATION: unknown
<220> FEATURE:
<221> NAME/KEY: unsure
<222> LOCATION: 15900
<223> OTHER INFORMATION: unknown
<220> FEATURE:
<221> NAME/KEY: unsure
<222> LOCATION: 15901
<223> OTHER INFORMATION: unknown
<220> FEATURE:
<221> NAME/KEY: unsure
<222> LOCATION: 15902
<223> OTHER INFORMATION: unknown
<220> FEATURE:
<221> NAME/KEY: unsure
<222> LOCATION: 15903
<223> OTHER INFORMATION: unknown
<220> FEATURE:
<221> NAME/KEY: unsure
<222> LOCATION: 15904
<223> OTHER INFORMATION: unknown
<220> FEATURE:
<221> NAME/KEY: unsure
<222> LOCATION: 15905
<223> OTHER INFORMATION: unknown
<220> FEATURE:
<221> NAME/KEY: unsure
<222> LOCATION: 15906
<223> OTHER INFORMATION: unknown
<220> FEATURE:
<221> NAME/KEY: unsure
<222> LOCATION: 15907
<223> OTHER INFORMATION: unknown
<220> FEATURE:
<221> NAME/KEY: unsure
<222> LOCATION: 15908
<223> OTHER INFORMATION: unknown
<220> FEATURE:
<221> NAME/KEY: unsure
<222> LOCATION: 15909
<223> OTHER INFORMATION: unknown
<220> FEATURE:
<221> NAME/KEY: unsure
<222> LOCATION: 15910
<223> OTHER INFORMATION: unknown
<220> FEATURE:
<221> NAME/KEY: unsure
<222> LOCATION: 15911
<223> OTHER INFORMATION: unknown
<220> FEATURE:
<221> NAME/KEY: unsure
<222> LOCATION: 15912
<223> OTHER INFORMATION: unknown
<220> FEATURE:

-continued

<221> NAME/KEY: unsure
<222> LOCATION: 15913
<223> OTHER INFORMATION: unknown
<220> FEATURE:
<221> NAME/KEY: unsure
<222> LOCATION: 15914
<223> OTHER INFORMATION: unknown
<220> FEATURE:
<221> NAME/KEY: unsure
<222> LOCATION: 15915
<223> OTHER INFORMATION: unknown
<220> FEATURE:
<221> NAME/KEY: unsure
<222> LOCATION: 15916
<223> OTHER INFORMATION: unknown
<220> FEATURE:
<221> NAME/KEY: unsure
<222> LOCATION: 15917
<223> OTHER INFORMATION: unknown
<220> FEATURE:
<221> NAME/KEY: unsure
<222> LOCATION: 15918
<223> OTHER INFORMATION: unknown
<220> FEATURE:
<221> NAME/KEY: unsure
<222> LOCATION: 15919
<223> OTHER INFORMATION: unknown
<220> FEATURE:
<221> NAME/KEY: unsure
<222> LOCATION: 15920
<223> OTHER INFORMATION: unknown
<220> FEATURE:
<221> NAME/KEY: unsure
<222> LOCATION: 15921
<223> OTHER INFORMATION: unknown
<220> FEATURE:
<221> NAME/KEY: unsure
<222> LOCATION: 15922
<223> OTHER INFORMATION: unknown
<220> FEATURE:
<221> NAME/KEY: unsure
<222> LOCATION: 15923
<223> OTHER INFORMATION: unknown
<220> FEATURE:
<221> NAME/KEY: unsure
<222> LOCATION: 15924
<223> OTHER INFORMATION: unknown
<220> FEATURE:
<221> NAME/KEY: unsure
<222> LOCATION: 15925
<223> OTHER INFORMATION: unknown
<220> FEATURE:
<221> NAME/KEY: unsure
<222> LOCATION: 15926
<223> OTHER INFORMATION: unknown
<220> FEATURE:
<221> NAME/KEY: unsure
<222> LOCATION: 15927
<223> OTHER INFORMATION: unknown
<220> FEATURE:
<221> NAME/KEY: unsure
<222> LOCATION: 15928
<223> OTHER INFORMATION: unknown
<220> FEATURE:
<221> NAME/KEY: unsure
<222> LOCATION: 15929
<223> OTHER INFORMATION: unknown
<220> FEATURE:
<221> NAME/KEY: unsure
<222> LOCATION: 15930
<223> OTHER INFORMATION: unknown
<220> FEATURE:
<221> NAME/KEY: unsure
<222> LOCATION: 15931
<223> OTHER INFORMATION: unknown
<220> FEATURE:
<221> NAME/KEY: unsure
<222> LOCATION: 15932
<223> OTHER INFORMATION: unknown -continued
<220> FEATURE:
<221> NAME/KEY: unsure
<222> LOCATION: 15933
<223> OTHER INFORMATION: unknown
<220> FEATURE:
<221> NAME/KEY: unsure
<222> LOCATION: 15934
<223> OTHER INFORMATION: unknown
<220> FEATURE:
<221> NAME/KEY: unsure
<222> LOCATION: 15935
<223> OTHER INFORMATION: unknown
<220> FEATURE:
<221> NAME/KEY: unsure
<222> LOCATION: 15936
<223> OTHER INFORMATION: unknown
<220> FEATURE:
<221> NAME/KEY: unsure
<222> LOCATION: 15937
<223> OTHER INFORMATION: unknown
<220> FEATURE:
<221> NAME/KEY: unsure
<222> LOCATION: 15938
<223> OTHER INFORMATION: unknown
<220> FEATURE:
<221> NAME/KEY: unsure
<222> LOCATION: 15939
<223> OTHER INFORMATION: unknown
<220> FEATURE:
<221> NAME/KEY: unsure
<222> LOCATION: 15940
<223> OTHER INFORMATION: unknown
<220> FEATURE:
<221> NAME/KEY: unsure
<222> LOCATION: 15941
<223> OTHER INFORMATION: unknown
<220> FEATURE:
<221> NAME/KEY: unsure
<222> LOCATION: 15942
<223> OTHER INFORMATION: unknown
<220> FEATURE:
<221> NAME/KEY: unsure
<222> LOCATION: 15943
<223> OTHER INFORMATION: unknown
<220> FEATURE:
<221> NAME/KEY: unsure
<222> LOCATION: 15944
<223> OTHER INFORMATION: unknown
<220> FEATURE:
<221> NAME/KEY: unsure
<222> LOCATION: 15945
<223> OTHER INFORMATION: unknown
<220> FEATURE:
<221> NAME/KEY: unsure
<222> LOCATION: 15946
<223> OTHER INFORMATION: unknown
<220> FEATURE:
<221> NAME/KEY: unsure
<222> LOCATION: 15947
<223> OTHER INFORMATION: unknown
<220> FEATURE:
<221> NAME/KEY: unsure
<222> LOCATION: 15948
<223> OTHER INFORMATION: unknown
<220> FEATURE:
<221> NAME/KEY: unsure
<222> LOCATION: 15949
<223> OTHER INFORMATION: unknown
<220> FEATURE:
<221> NAME/KEY: unsure
<222> LOCATION: 15950
<223> OTHER INFORMATION: unknown
<220> FEATURE:
<221> NAME/KEY: unsure
<222> LOCATION: 15951
<223> OTHER INFORMATION: unknown
<220> FEATURE:
<221> NAME/KEY: unsure
<222> LOCATION: 15952

-continued

<223> OTHER INFORMATION: unknown
<220> FEATURE:
<221> NAME/KEY: unsure
<222> LOCATION: 15953
<223> OTHER INFORMATION: unknown
<220> FEATURE:
<221> NAME/KEY: unsure
<222> LOCATION: 15954
<223> OTHER INFORMATION: unknown
<220> FEATURE:
<221> NAME/KEY: unsure
<222> LOCATION: 15955
<223> OTHER INFORMATION: unknown
<220> FEATURE:
<221> NAME/KEY: unsure
<222> LOCATION: 15956
<223> OTHER INFORMATION: unknown
<220> FEATURE:
<221> NAME/KEY: unsure
<222> LOCATION: 15957
<223> OTHER INFORMATION: unknown
<220> FEATURE:
<221> NAME/KEY: unsure
<222> LOCATION: 15958
<223> OTHER INFORMATION: unknown
<220> FEATURE:
<221> NAME/KEY: unsure
<222> LOCATION: 15959
<223> OTHER INFORMATION: unknown
<220> FEATURE:
<221> NAME/KEY: unsure
<222> LOCATION: 15960
<223> OTHER INFORMATION: unknown
<220> FEATURE:
<221> NAME/KEY: unsure
<222> LOCATION: 15961
<223> OTHER INFORMATION: unknown
<220> FEATURE:
<221> NAME/KEY: unsure
<222> LOCATION: 15962
<223> OTHER INFORMATION: unknown
<220> FEATURE:
<221> NAME/KEY: unsure
<222> LOCATION: 15963
<223> OTHER INFORMATION: unknown
<220> FEATURE:
<221> NAME/KEY: unsure
<222> LOCATION: 15964
<223> OTHER INFORMATION: unknown
<220> FEATURE:
<221> NAME/KEY: unsure
<222> LOCATION: 15965
<223> OTHER INFORMATION: unknown
<220> FEATURE:
<221> NAME/KEY: unsure
<222> LOCATION: 15966
<223> OTHER INFORMATION: unknown
<220> FEATURE:
<221> NAME/KEY: unsure
<222> LOCATION: 15967
<223> OTHER INFORMATION: unknown
<220> FEATURE:
<221> NAME/KEY: unsure
<222> LOCATION: 15968
<223> OTHER INFORMATION: unknown
<220> FEATURE:
<221> NAME/KEY: unsure
<222> LOCATION: 15969
<223> OTHER INFORMATION: unknown
<220> FEATURE:
<221> NAME/KEY: unsure
<222> LOCATION: 15970
<223> OTHER INFORMATION: unknown
<220> FEATURE:
<221> NAME/KEY: unsure
<222> LOCATION: 15971
<223> OTHER INFORMATION: unknown
<220> FEATURE:
<221> NAME/KEY: unsure -continued
<222> LOCATION: 15972
<223> OTHER INFORMATION: unknown
<220> FEATURE:
<221> NAME/KEY: unsure
<222> LOCATION: 15973
<223> OTHER INFORMATION: unknown
<220> FEATURE:
<221> NAME/KEY: unsure
<222> LOCATION: 15974
<223> OTHER INFORMATION: unknown
<220> FEATURE:
<221> NAME/KEY: unsure
<222> LOCATION: 15975
<223> OTHER INFORMATION: unknown
<220> FEATURE:
<221> NAME/KEY: unsure
<222> LOCATION: 15976
<223> OTHER INFORMATION: unknown
<220> FEATURE:
<221> NAME/KEY: unsure
<222> LOCATION: 15977
<223> OTHER INFORMATION: unknown
<220> FEATURE:
<221> NAME/KEY: unsure
<222> LOCATION: 15978
<223> OTHER INFORMATION: unknown
<220> FEATURE:
<221> NAME/KEY: unsure
<222> LOCATION: 15979
<223> OTHER INFORMATION: unknown
<220> FEATURE:
<221> NAME/KEY: unsure
<222> LOCATION: 15980
<223> OTHER INFORMATION: unknown
<220> FEATURE:
<221> NAME/KEY: unsure
<222> LOCATION: 15981
<223> OTHER INFORMATION: unknown
<220> FEATURE:
<221> NAME/KEY: unsure
<222> LOCATION: 15982
<223> OTHER INFORMATION: unknown
<220> FEATURE:
<221> NAME/KEY: unsure
<222> LOCATION: 15983
<223> OTHER INFORMATION: unknown
<220> FEATURE:
<221> NAME/KEY: unsure
<222> LOCATION: 15984
<223> OTHER INFORMATION: unknown
<220> FEATURE:
<221> NAME/KEY: unsure
<222> LOCATION: 15985
<223> OTHER INFORMATION: unknown
<220> FEATURE:
<221> NAME/KEY: unsure
<222> LOCATION: 15986
<223> OTHER INFORMATION: unknown
<220> FEATURE:
<221> NAME/KEY: unsure
<222> LOCATION: 15987
<223> OTHER INFORMATION: unknown
<220> FEATURE:
<221> NAME/KEY: unsure
<222> LOCATION: 15988
<223> OTHER INFORMATION: unknown
<220> FEATURE:
<221> NAME/KEY: unsure
<222> LOCATION: 15989
<223> OTHER INFORMATION: unknown
<220> FEATURE:
<221> NAME/KEY: unsure
<222> LOCATION: 15990
<223> OTHER INFORMATION: unknown
<220> FEATURE:
<221> NAME/KEY: unsure
<222> LOCATION: 15991
<223> OTHER INFORMATION: unknown
<220> FEATURE:

-continued

<221> NAME/KEY: unsure
<222> LOCATION: 15992
<223> OTHER INFORMATION: unknown
<220> FEATURE:
<221> NAME/KEY: unsure
<222> LOCATION: 15993
<223> OTHER INFORMATION: unknown
<220> FEATURE:
<221> NAME/KEY: unsure
<222> LOCATION: 15994
<223> OTHER INFORMATION: unknown
<220> FEATURE:
<221> NAME/KEY: unsure
<222> LOCATION: 15995
<223> OTHER INFORMATION: unknown
<220> FEATURE:
<221> NAME/KEY: unsure
<222> LOCATION: 15996
<223> OTHER INFORMATION: unknown
<220> FEATURE:
<221> NAME/KEY: unsure
<222> LOCATION: 15997
<223> OTHER INFORMATION: unknown
<220> FEATURE:
<221> NAME/KEY: unsure
<222> LOCATION: 16227
<223> OTHER INFORMATION: unknown
<221> NAME/KEY: unsure
<222> LOCATION: 16250
<223> OTHER INFORMATION: unknown
<223> OTHER INFORMATION:

<400> SEQUENCE: 18
gaattcagcg cgccgagtct gcgtatggcc ggggtacgag gcgctccctg cgcagggtgg 60
gcaggaccga agctcgccgg gagctgcgcg gagggcgggc ggggaccctc cggtgccgct 120
cccaccccgc ggggccgccc ccgagcccgc cctccgccgc cgccctcgcc ctcgtcgccg 180
ccggaaagtt tgcaccgacc ccgatctggc agcgccgcga agacgagcgg tcaccggcgc 240
ccgacccgag cgcgcccaga ggacggcggg gagccaagcc gaccccccgag cagcgccgcg 300 cggtgagcac ctgggccgcg gacccgaggg gacgttgggg agtcgacccg gtggggacag 360
agaccgcggg gcgggcgcgg cggggccggg ggcgcgggga gcggggagcc ggccgggcgg 420
tctccggggt ccgggctggt gcgctcctca gtcccgtcag acaccccccgt tcccaacccc 480 ggctcggaca ccacccggtc ctgcaccgtc gggcaggtcc aggggtctca gcccctcccc 540
cgttctctgg tcctgggggg cgcggctggg ggcgggggtg tcgctgccgc ctgggccctg 600
cggcggccac actgcagcgg ccacactccc cactcagggc cccgggcccc gccgccctgg 660
ggagcgcaca aagcgcgcgg acgcgtcccc gaggcgcggg gtctcaccag cgctgtctcc 720
cctcggtggc tcctgccccg aggactgccg gtggcaccgc gcggcccagg atggggtgag 780
gggtgtctgg cccgtcctgc cgctctcttc cgcggccaca ctgcgacttt gaccgggaag 840
cggtcactgc ctgcccgctc cgcccccccg cgccccacca cctcgcgact cggccaccgg 900
gcttatgctc cgactctgaa ccgactgacc ccggccccct cggcgcccgc atcctccaag 960
gaccggccag ggctgctctc tgcccttggt attggggaca tcagggttgg ggggtctggg 1020
tgcacccacg cctgccccgc ccccacgggg tgagggcgca gggatagggc tttgtcaaca 1080
gcctgtggcc cctgatcccg ccccggtgcc ctgaccttcc actaccttct ctggtttcac 1140
aaaaacatcc cggctcccat cccggagctc ctcaaagcgt ctgagaggcc ccttgcggac 1200
gccctgggag ccccgctgcc ttcctggacc agtggccgct ccacccatcc tgggggccca 1260
gctccaggtc tgcgggtccc tcagccgccc ccagtgggaa tcggtggagc ctgacgcagc 1320
caggagcgcc caagagtcac gtgttctgcc agggaggaca tgggacagga cacggggtgc 1380

-continued

```
cagccctgca aagcggccgg ggcagtggag ctcaggtggc cctaagccct ggtggtggct   1440
ggtgtggccc ggcaggcagc tgtgggaggg aggaaggggg tggcatgcgg tgggggtcta   1500
gagaaggcgg gcagggcacc tcgggagccc ccccattggg cacctcggga accccccaca   1560
ttgggcacct cgggaaccct cccattgggc acctcgggaa ccccccacat tgggcacctc   1620
gggaaccccc gcattgggca cctcgggaac cctcccattg ggcacctcgg gaaccccccct   1680
attgggcacc tcgggaaccc ccacattggg cacctcggga acccccccta ttgggcacct   1740
tgggaacccc tcccctaatt ctcagctgac tccaaggcct gagaaggagc ttggtcacct   1800
ggactgtgaa ggtggagggt ggggtccctg gtgggtcgtc ccacctacca gctgtgtcgc   1860
cggaagggta atacggagca ctgtggcccc ggggagcccc gagtggcagc tccacagctg   1920
ggagtttctg tccactcctt cagtcaacaa acattgatcc tgggctgacc ggggcccggg   1980
ggtgtcagtg tctcctctcg ggggagaggg ctgggtgaga tcaacagagg agcctccctt   2040
cttcccttca ggctggtgtc accttcagtg atggggcagg gtccccactt gggaagttaa   2100
atcgtcgtcc ccgtcccagg accacagcag cctcagccct gctctccagg ccaggctctc   2160
tcatgggtgc tcagctggaa attggtcccc ccccggctcc acccacccct gttggggtga   2220
ggagctggag tctccctacc catatgggac ccaccacccg cagggaacgg aggacgctca   2280
cacttctgca cctcctgcct cactatcaga gacccagtgg agaattgcct cccacctcac   2340
ctcttgtatt cagaggccct gacccctagg gatccgggac taggggtgcc ctatggggag   2400
cccacctgtg gcctgtggat gctgagctgt cgggggaatc ctccaggatc cccagcccca   2460
ccttcccaac cttctgttga ggctgagggg acacagagcc ccactcctgg gtcctgactg   2520
tttcaaagaa aggcctgggg gactgggcag ccaacccctc cctcggctcg ctggggtctc   2580
cagactggct gcccggctgg aaggtggggc cctggcacgc gaggacctca tgtgtggagg   2640
cactggcttg gggggtgctc ccagtggctc tagagtcaac atgacaggca tcgaatggct   2700
cctgtttctc tggcagagtt ggggcagagc caggcttggc cacgctgggc tctaaggggc   2760
tgtcattttg cccagggagc tcctggctgg gtggtcctcc ccccagggtg agcacgcgtc   2820
ccccccaccc ccacttcgag gcgcccaggc agggaacagc tcattggcca gtgtccttcc   2880
tccttgtccc ccgcctgcat ctccaccatc caccctgctc cagctgcccc ttgtccctct   2940
ccccgtcccc tgcccagagc cccaggtctc ccctgcaccc ctgagcctgc ccacctagca   3000
gtgcccctcg tccagggccc ctctgggttg ggggtgcaca cagtggggag aggcggctcc   3060
tgctgctcct cacccagccc ggctcagtgg ccggagccgc ccaggacagt ggcagtagat   3120
ggggctgttt gatcaggatc agggaagata aggccccttg cgtgacccca gagctgggga   3180
cgccaaaact gcccctcctc ccccacccgc ctgccgctgt ctccgccagg gagaggcccc   3240
tactctgtgg gtccttcgcc ccagcaccaa gcctgcatgg ctgctcacct ggctcaggaa   3300
ctggggatca gcgacacacg ggtcctgcct cccatcggcc cctacatgag cccagggtcc   3360
aagggctgcg gttgggagct ctttagcagt ctgtgacgca ggtgcctgtc cctgtcattc   3420
agctgtcaca ctgcttgggg catctcaggc cccgttagcg ggaggccctg ggtggagctg   3480
gccccacgcg ggctcaccca gccgctacct ggaggaggct aaaatccagg ctgtcccgtg   3540
gcagccagca gtccaggcct gcccggaaac cctctgctcc agctgcagcc ttcgcccatc   3600
tccttgcccc tctccccggc ttccccctgg cactgccttc cagctggctg gccctccatc   3660
tgcccagcca tccatccaca cctcttattc catttgaggg tgccccaaag aagagcccgt   3720
```

-continued

```
aacagcccgg gggctcatag ccagccactc gcgggacccc gcacatgcac gtggacccac   3780
aggaagaccc tccctgcttc tcccacagaa ttcagttggt gcagaaactg ggctctgtag   3840
caacgaaagg ccgatttgtg tagctgttgc caccccgaac tcccagctca gatgctggct   3900
gtggcatggg gaccaggggc tgtgactccc acagccctgg caggcaccac gggggatgtc   3960
ctccccaccc tgtgccccca ccctaggcca gctcctcctc caagtcgacg cccgcagtgc   4020
taacctcaaa ggactgtgca gccagcctgt ggcgtcccat gggatccagg aagcccaacc   4080
gagccttgca cggcacccac gaggcaccta ggcaccccgg tgctgggcag gggcacacaa   4140
tgtgacacag accccctgagt gtgggcccca cacacttggc ctggcacagc tgcaagccag   4200
cccagccact ttgctcgctg tggcactggg gccaagtgat ggaaggtcca ggcaccgcca   4260
ccctcacgct tggcacattg gctcaggtca gcctggcaag ccagctttcc caggggctaa   4320
gaataggtga ggaggatggt gaggaagcag ctggggctgt caactgaggg aggaggtcac   4380
atctggggat gctggtcacc acccaagagc attgggtcac ctagcagaag gtggctgcaa   4440
cagcaatgag acgagggctc tcgacctcag agctgcagca gccagccttg gtgcagagtg   4500
atctctgggt ctctcctcta tgcctctttt tttttttttt tgagagagtg ctctgtaaca   4560
gctgactcat gctgatctcg taatcaagtc tgctcggttc agcattctgc tcagccggag   4620
agggggatag aagcgacaag ctgctatttt tttttttta ttnnnnnnnn nnnnnnnnnn   4680
nnnnnnnnnn nnnnnnnnnn nnnnnnnnnn nnnnnnnnnn nnnnnnnnnn nnnnnnnnnn   4740
nnnnnnnnnn nnnnnnnnnn nnagaaaaat ctgaatatac tcaaagtggt tggcctcact   4800
ttggaaatgc aagctgctgt cggagaaact agtgaagaga gttcagacag cccaggggca   4860
tctggaagaa ttaagagaga acaaactttg ctatatcaac actggccaga aaagtgagtc   4920
tggaaattgc cacatgaaat gtctacgtca agacaggata gcagatcggg ggatcccgag   4980
ggcaggcagg ctgggaacct tggagcggag ggcactgttc acgcctgggg ctgcattcct   5040
ctgcaccggc tgcactttgt aagcaagtgg taccattagc agaggaaaag ggcacctgaa   5100
aacatggcta tggtattgca ggacctgcct caaaatcgca ctcactggtt cccaccagac   5160
accaccacac agaccacggg caggtgaaca ctgagaagta acaatgcgct gggcggcgtg   5220
gctcatgcct gtaatcccag caatttggga ggcccagacg ggcagatcac ttgaggtcag   5280
gagtttgaga gcagtctggc caatgtggtg aaactccgtc tctactaaaa atacaaaaat   5340
tagccaggca tggtggcaca ggcctgtagt cccagctact cgggaggctg aagtgggagg   5400
agtgcttcaa cccgggaggc ggaggttgca gtgtgccaag atcgcgccat tgcactccag   5460
cctgggcgac agagcgagac tccgtctcaa aaaaaagaaa gaaaaatgag gccaggtgca   5520
gtggctcacg cctatcatcc cagcactttg ggaggccaag acgggcggat cacttgaggt   5580
caggagtttg agaccagcct ggtccacatg gtgaaacccc gtcactacta aaaatacaaa   5640
aattagccag gcgtggcacg tgcctgtaat tccagctact caagacgctg aggcacaata   5700
atcgcttgaa cccgggaggc agaggttgcg gtgagctgag atcatgccac tgccctccag   5760
cctaggtgac agagcaagac tctgtttcag aaaaatggcc aggcacagtg actcatgcct   5820
gtaatcccaa cactttggaa gaccaaggcg ggcagatcac ctgaggtcag gacttgaaga   5880
ccagcatgac caacatggtg aaaccccgtc cctactaaaa atacaaaaat tagctgggca   5940
tgatggcgca cgcctgtaat cccagctact cgggaggctg aggcagaaga atcacttgaa   6000
cctgggagac agaggttgca gtgagccgag atagcgccac tgtactacag cctgtgtgac   6060
agagcgagac tccacctcaa aaaataataa aataaaaaag aaataaaaat gaaaccctaa   6120
```

-continued

```
gcccccccca accaactgaa ccagcctcct cttggcccag gggaccccag aaaccttgaa   6180
agctgagttc ctggccatgg ctgggtggga gatcagacac atctgcaggc tctcttccct   6240
aagggataaa cagaaagcag ccctttccaa agacccctgg gctggtatct gacatcagcc   6300
aacctcccgc caggcccttc tctcttgcgg tttcttcaaa acaacccaca ggtatttcct   6360
gataagaaac caccaaccat ggagtggttc tggcacagtc agggttttcg tggcacagtc   6420
ttcatgtcct ctgatttgcc atttatttat ttatttactt atttactttt tttgtagaga   6480
cagggtctca ctatgttccc caggctgatc tcgaattcct gggctcaggc aatcctccgc   6540
ctcgggcacc caaagtgcta ggattacagg catgagccac ttcacccagc ctgcttcacc   6600
tctgacttca gaggccaaaa attccaccct caggtcatgc tggcactgcc attttttgca   6660
cataggaccc gtgaagaggc aggaagctca actgtgtgca cagttctcct ttcatgaata   6720
ctcatgatcc tcctacagcg tattaagtac gtctgtatca gccaccccat tcggtgtaaa   6780
tccctgtctt attcttccct ctcttgaagt gtctgtttcc agcttctggc tggaggctac   6840
acttcccagc ctgttagaat ggccaccctg caagctgcaa ccggttatga gaaataaagc   6900
cctcctttcc aaacatatga accgcattct tcagttgaca agagagactg gagaaggatg   6960
gtgtgaaggt ctggggcaga aagcccaaga ccacctggca ttcagagcac aggtcctggg   7020
attctcacgt ggtccagaca caaggtagaa gactggaatg acttggcagg tatcacccct   7080
aagaaactcc tcccaggaga gcctcgtaag gcagggtggg caatgccagg agggcaagct   7140
cctgccctct gcccccagtg ttaggacaac agtactgtaa aaacaggtct tcaagggcag   7200
gcatggtgac tcatctctgt aatcccagta ctttgggagg ccaaggcagg cggatcacaa   7260
ggtcaggagt tctagaccgt cctggccaat gtggtgaaac cccatctcta ctaaaaatat   7320
aaaaattagc tgggtgtgtt ggtgagcacc tctaatctca gctactcggg aggctgaggc   7380
aggagaatca cttgaaccta ggaggtggag gttgcagtga gccaagaccg tgccactgca   7440
ctccagcctg ggcgacaaga gtgaaaccct gtctcaaaaa caaaacaaaa caaaaaaaac   7500
accagaaaac aggactttaa agtgaaaagc ttcgcgtgtg ggatagacac gcacatccta   7560
tccatatgag ggctctgacc cttctgctgt ctcagactcc ttgagagtct ggcagaagcc   7620
ctctcttggg aacaatatcc ccacacagaa gcgtacgtgt aattccaggg gctgtgagac   7680
tgcagggatc cacctgcagt tttcaaggca tcctatttct ccacggccag ctctttcccc   7740
tcagagcccc actgggaact tatgcaactc aatgcaataa aacctacagg gggttgaatg   7800
gtggcccccc caaaaaagat gggtcaatgt cctcaccccc aggacctctg aacatcttac   7860
tagggatcct ggtctttgaa gatgtaatga taaatcgttc tagattatcc aagtggaccc   7920
taaatccaat gacaagggtc ttcctgagac acagagaaaa caggaaaagg ccacaagaaa   7980
tcggaggcag agagcaatgc ggccacaagc cacagaacgc ttggagccat gagaagctgg   8040
aagaggcagg agggattctc ccttagggca tttggagaga gtgtgccctg ccaaggcctt   8100
gggtctccag agttgggagg gaatatatga ctgtttaaaa ccacctgggg gcttttccaa   8160
gtgagagcca gtatgttcag ggggcagggg cacagatata ctcagaccct gctgctgagc   8220
tggagcaaac tcacttcaga tcatattcac aggggttgaa gtcctgccgc cggcacgtgt   8280
cctccagaac ctgggggtga gatgaaagga tggtgaactg ctgagtgtgc agggctggcg   8340
ggcgcagtgg gccaggtcag ccaagggcat tcagcttcct ggtgagccag gtggctctgc   8400
ccaggcaaag ccaagcacaa gaccacacta tggacggtcc ccgcaacaaa tgcaggctct   8460
```

-continued

```
cacctgcaaa tcctgtccac tctccctccc ttcttcacca tcccctcagt tttgtaggaa   8520
agctccactc agagttcccc tgcagtacag caacacgggc atcttcctgg cacacaccct   8580
gggctctcct tcaaaccctg tagttctgca acctgcctta aacttgccta gcacaagcta   8640
ccccctggct ctggcacggt tctgtgcacc tgctgccact gcctgcaccg cctccgcccc   8700
tcttctccat aaaaagccaa agccgtggcc ttgcaccaag ggtcccgcg cagcctctgc   8760
gggagcgccc cacttccgca ctctgcacgc ctggcaccaa cagcctcctg gctgcgccct   8820
ccacctgccc aggcctgggg accccacgcc gtgggctgct cccgcaaact ccgagtcgtg   8880
tgcaccttcg gatcctcacg gtcccccacg cagcagaggc tcaataaata cttttttttt   8940
tttttttga tatggagtct cgctctgtct cccaggctgg agtgcagtag cgcgatctcg   9000
gctcactgca agctctgcct cccaggttca cgccattctc ctgcctcagc ctcccgagta   9060
gctgggacta caggcgcccg ccaccacgcc cggctaaatt tttttgtatt tttttagtac   9120
agacggggtt tcaccgtttt agccaggatg gtcttgatct cttgacctcg tgatccaccc   9180
gcctcggcat cccacagtgc tgggatttac aggcgtgagc caccgcgccc agccaatact   9240
tttacattta attgattcgc ggtcacaagg tgcccaagta aaagtgcagt gagtgactcg   9300
gcaaaaatcg cttccaggcc ccacggccgg gacatctgcc accgcgcaac ccgggctccc   9360
gctccggggg acgccccgga atgggaacgc gggtctaggg ctccactcct ccctcttccc   9420
ggcgccctcg cgagctgggc tcgccgggcg ccgagtactc gatgcgggtg acacgcggcg   9480
ccgttctacc tcacccctgg gaaggctcgc caccgccccg cccccactcg ggaccccccgg   9540
gacccccggg accccagcgg aagcgcaggt gacggcgagc agggggcggg gccgccgctc   9600
aggaggccgc tcattggccg ccgagccccg cccccgaaca ccgggacgcc gaccgcaatg   9660
gcggggccct cggcgcagcg ccccccgccc gccttaancc cgtgccccgg gcgggcggcc   9720
gcacctgaag cagcacggtg ctcggcgtca ccttcaccgt gtggcgccgg ccgttcgggg   9780
ccagcaccga caccgcggag cctccgccgc ctgccggggc cgccattttc cgctcacgtg   9840
acccgccgcc gggccggcgt caaacaactt tatcggcaac agccaggacg cgcagccacg   9900
cggccagggg gcggggccgc agcgcacttc cgggtcctgc caggccccgc cctttcccca   9960
cccacggcgc cccggccccg cccttgggcc gccaaagccc gcgccagacc cggaaagcgc  10020
ggtcgtcctc tgcctccggg aagcgcggct tggatgggct cgccggggcc aggctgggcc  10080
ggggctgggc gcgcggtcac ccccggtgag cggcactgag ccccggggtc ccagcggtcc  10140
gcgctcgccc accctcgctt cgtccctgac acgtccccag ctcggtgccc tgctctcccc  10200
cgaccctccc ggcttcctcc actccagcag ctgagcctct tccctgccca cctgtccctg  10260
tggtcagcgt ccacctcctg accttatggt ttggggcagt ccccccgccc ctgtacggat  10320
cctccctggg tgttgggact cgtggccctc agtctagacc tgatttcttt catcctaaaa  10380
tgggagtgca gaatctggca gccctaggct gccgcgacgg tccctaaacc tgagggtagg  10440
aaaggcggga gaccggtttc agaaccgtgg ggtgagcgaa cttgagtctc accggagctc  10500
ctgccgaccc acaggcactc aaggacttcc cgcaccaacc catgctgagg aggggcttgg  10560
tggcagcctc aggaaacact cccatcgcca gccaccgcag cagggaaagc acctggcctc  10620
accagctcca ggcttccaga aggagctgcc ctcctgactc gcagccgtcg aatgtgctta  10680
gctcccagca cctgggccac tcatggacag cactcgcacg tgttccgccc cgccccccac  10740
ctccatggct cagccgggcc ttggcactcc tctctccatg tgcctgcctg tctctgcgga  10800
ctcctggcta gggctcagct gcccagtagc ctgtggaagg gggaactggt gcagttatca  10860
```

-continued gtcaatcctc ccacagggct gggattacac acgtgagcca ccgcacccgg cagtcattgc 10920
tgagtctaag gacatctctg catgggtgct gttgtgcctt cctgtcgatg acatatccat 10980
gtcacccaca cacacctgta tgctgacaaa cacggacatc tatgtacatt ggagaaacct 11040
ggggaaagcc ccaggctagc catagccctc ccatccagcc agccagtccc atgctctgtg 11100
caacctcaga accttactga gccacacatc acctggtggg ttttaattct ttagtggcgt 11160
ttttgaagag tctgttccta ttttccttag actgtcccac agtctggatc cttggttaaa 11220
cgtttggggc aatgatgaag ggaggtgaca agtcagcagg aggtgcagga catcagcgtg 11280
gccatgagtg aggacgtgaa gttgaaccac ttggtcagct ttgggtctgc tgaattcctc 11340
catggtcaag gtccgtggct ccttgtggag taattaaggc atgcgtgagg tcattctctg 11400
agaccacaag catcaagttt tcccaataac catttgccca acagttttag catcagttaa 11460
tgagtagatt cagtgttaaa ccgtaaagct gcaaaatcat ggcttcccaa gtttattgtt 11520
tcttctacat ttatagtcac tttcggtcaa gcttcccctt ctttaaaaag ttattaaata 11580
tttgggaggc tgaggcagga gaatggcgtg aatccgggag gcagagctcg cagtgagctg 11640
agatcacgcc actgtactcc agcctgggag acggagcaag actctgtctc aaaaaaaaaa 11700
aaaaaaaaaa aattaaatat ggccaggcgc ggtggctcac gcctgtaatc ccagcacttt 11760
gggaggctga gttgggcaga tcacaaggtc aagagattga gaccatcttg gccaacatgg 11820
tgaaatcctg tctctactta aaaaaaaagt acaaaaatta gccgggcatg gcggtgcgtg 11880
cctgtaatcc cagctattcg ggacactgag gtaggagaat cacttgaacc tgggagatgg 11940
aggttgcaac gagccaagat cgcaccattg cactccagcc tgggcgacaa gagtgaaacc 12000
ccatcttgaa atatatatat ttattaatat gaattcatgt atttttttca ttcagtcagc 12060
attctttttg atgctcaaat tggtccgaat ttggccagtg agacctcctt taagctggct 12120
cctatgcttt ttttgatagg agggatgatc ttttatcctg atattatttc aaacttagcc 12180
gagcaaggtg gctcacacct gtagtcttag ctactccggt ggccgaggca ggagaattac 12240
ttaagttcca gccttagtga accactattc atgcctatga ataactactg caccccagcc 12300
cgagcaacgt agtacgatac cgtctcaaaa aaggagaagg agaagaaaga agaagaggga 12360
ggaggaagga agaaagagaa gaaaagtttg caaaagcaag aattcctgct gtatatcttt 12420
tttttttttt tttttttttg gagatggagt ctccctctgt cgccaggctg gagtgcagtg 12480
gcgaaatctc agctcactgc aacctctgcc tcccgggttc aagcgattct tctgcctcag 12540
cctcccgagt agctgggact acaggtgtgc agcaccacac ccagctagtt gttgttttgt 12600
tttgttttgt tttttgagac ggagtctcgc tctgttgccc aggctggagt gcagtggtgc 12660
aatctcggct cactgcaagc tccgcctccc gggttcacat cattctcctg cctcagcctc 12720
ccgagtagct gggactacag gcacctgcca ccatgcccgg ctaatttttt gtatttttag 12780
tagacatggg gtttcaccat gttagccagg atggtctcaa tctcctgacc tcgtgatcca 12840
cccgcctcag cctcccaaag tgctgggatt acaggtgtga gccaccacgc ccagccccca 12900
gctccctctt tatccctagg accctgaggc tcagaggggc agcttcaggg gaggacaccc 12960
cactggccag gacgccccag gctctgctgc tctgccactc agctgccctc ggaggagcgt 13020
acacacccac caggactgca ttgccccagc tgtgcagccc ctgccagatg tgggaggcag 13080
ctagctgccc agaggcatgc ccccctgcca gccacagcga cccctgctgc tgttgctgct 13140
gctgctggcc tgccaggtga ggactcacag caccctcagc acccaggggc cctcctgtga 13200

-continued

```
ggactgcaca ctgatggctc tctgtctgcc tgcctgcctg cctgcctgcc tgcctgtctg  13260
tctgtctgcc cgtctgcctg cccatctgcc tgtctgtctg cctgtccgtc tgtctgtcca  13320
tctgtccatc tgcctatcca tctgcctgcc tgtctgcctg tccgtctgcc tgtctgtctg  13380
cctgtccatc tgtccatctg cctatccatc tgcctgcctg tctgtcggcc tgcctgcctg  13440
cctgtctgtc tgctgcctgt ctgtccgtct gcctgtctgc ctgtccgtct gcctgcctgt  13500
ccgtctgcct gtccgtctgc ctgcctgcct gtctgtctgc ctgcctgtct gcctgcctgt  13560
ccgtctgcct gtccgtctgc ctgcctgtct gcctgcctgt ctgcctgtct gcccgtctgc  13620
ctgtctgtct gcctgtccgt ctgcctgtct gtccgtctgt ccatctgcct atccatctgc  13680
ctgcctatct gtctgtccgt ctgcctgcct gtctgtctgc ctgtctgcct gtctgtctgc  13740
ctgtctgtcc atctgcctat ccatctacct gcctgcctgt ctgcctgtct gtctgcctgt  13800
ctgtctgcct gcctgtctgt ctgtctgtct ggttgcttgt gcatgtgtcc cccagccaca  13860
ggtcccctcc gctcaggtga tggacttcct gtttgagaag tggaagctct acggtgacca  13920
gtgtcaccac aacctgagcc tgctgccccc tcccacgggt gagcccccca cccagagcct  13980
ttcagcctgt gcctggcctc agcacttcct gagttctctt catgggaagg ttcctgggtg  14040
cttatgcagc ctttgaggac cccgccaagg ggccctgtca ttcctcaggc ccccaccacc  14100
gtgggcaggt gaggtaacga ggtaactgag ccacagagct ggggacttgc ctcaggccgc  14160
agagccagga aataacagaa cggtggcatt gccccagaac cggctgctgc tgctgccccc  14220
aggcccagat gggtaatacc acctacagcc ccgtggagtt ttcagtgggc agacagtgcc  14280
agggcgtgga agctgggacc caggggcctg ggagggctcg ggtggagagt gtatatcatg  14340
gcctggacac ttggggtgca gggagaggat agggctggag gactcacccg ggaggcagtg  14400
cctgggttcg gatgagggag gcagccacca ctgggcagag gggggcaggt gtggcagcct  14460
ccattgggca gagggagcag atgtggcagc cacaggtttg gcgatgcacc tgggaaggat  14520
gaaaatggca ttggggttca gcccccagag agggaggtgc tgagagaagg tcacggagaa  14580
tgggggaccc cagtgtgggt ttggggcaca tttgagatgg ggggtctcca agggaaggtg  14640
tcctgcagag ctgcaattca gggctgggct gggcgtgcta gcggaggctg gtccagggga  14700
ggtggatggt caggtgagga aggtggaggt cagatggggg aggtggaggt caagtggggg  14760
agggagcagc ccaggccatg tcctgggcga ggtgacggcc gagctcaggc ttccagagag  14820
aggagagagg cctgctgagg gagccccttc tcccaccctg ccctgccctg ctctgccctg  14880
ccctacccta ccctgcagag ctggtgtgca acagaacctt cgacaagtat tcctgctggc  14940
cggacacccc cgccaatacc acggccaaca tctcctgccc ctggtacctg ccttggcacc  15000
acaaaggtac ccatagaggg gaggaactgt gggggggcg ggcccagggt ggggctgacc  15060
ccagcctccc cccacacccc cagtgcaaca ccgcttcgtg ttcaagagat gcgggcccga  15120
cggtcagtgg gtgcgtggac cccgggggca gccttggcgt gatgcctccc agtgccagat  15180
ggatggcgag gagattgagg tccaggtcag tgggcggcag gcaggcgcgg tggggctgga  15240
tgggaacggg catgggggcc cctgcctggc cctcacaggc cactgtaact cgcagaagga  15300
ggtggccaag atgtacagca gcttccaggt gatgtacaca gtgggctaca gcctgtccct  15360
gggggccctg ctcctcgcct tggccatcct gggggcctc aggtaggatt ccgccagcgc  15420
ccggcggcgc cgcagaggac agggaggagg acgggcgctg actggctgtg ccacagcaag  15480
ctgcactgca cccgcaatgc catccacgcg aatctgtttg cgtccttcgt gctgaaacca  15540
gctccgtgct ggtcattgat gggctgctca ggacccgcta cagccagaaa attggcgacg  15600
```

-continued

```
acctcagtgt cagcacctgg ctcagtgatg gagtgagccc tctcggcggc ctcaggcagg  15660
tgggtgggtc ggcagcacgc aggtggcacg tagccggctc acattgcact gtacaggcgg  15720
tggttggtgc gttttggcgc gcgccaggca aaaggcacgt ttcaactact tcttctgttg  15780
tttttttctt tatttacacg ggcggccgac aaccccccca aagattttct aatctctatt  15840
gttattttgt gtgtatggtg ttttatgtag tgggtaagcc gccgacgagc ggtgggcnnn  15900
nnnnnnnnnn nnnnnnnnnn nnnnnnnnnn nnnnnnnnnn nnnnnnnnnn nnnnnnnnnn  15960
nnnnnnnnnn nnnnnnnnnn nnnnnnnnnn nnnnnnnaaa taaacaatac cacttcgcgg  16020
cggcccccgc cgtggcgatc aataaaaaat acaaaaagta aacaaaaaaa taaactaccg  16080
cgctcccact gcacctgtac caagcggttg ctggctgcgt tgtggcggcg tgtttcatgc  16140
aatatggcat cgtgccaaac tactgctgct tgctggtgga ggccctgtac ctgcacaacc  16200
tgctggcctg ccaacgatcc ccgagangag cttcttcagc ctctacctgn tcatcggctg  16260
gggtgagtgg gctgccatga gagggtgtta aggcaggtga ccaagccttt ggaaccacag  16320
ctgctgcccc ccacaggtgc ccccatgctg ttcgtcgtcc cctgggcagt ggtcaagtgt  16380
ctgttcgaga acgtccagtg agtatgagcg ctggacagcc tggggagtga ccggggggct  16440
ggggtgcggc gctctggcct gaggcaggga ggggccgggg atgagcctgg tgcctgggga  16500
gggggtcatt tgtgaccttc tcccttcctt ttctgagacc cgaattagat cctggcaaaa  16560
tcgggacggg ggtgctgagg ggcggagggg ctgggggctg tgccccagta tgtgagtggc  16620
ctggcctcgc aggtgctgga ccagcaatga caacatgggc ttctggtgga tcctgcggtt  16680
ccccgtcttc ctggccatcc tggtgaggaa atgaagagcc aggaacgcac cccaggcccc  16740
tcctcccttg gcgtcctgag gctgccccag gagacagcag catcctgtct gagagcgctg  16800
ggagggagcc ggcacccaga caggacacca ggacactggc cagcaccctg gacactgagc  16860
caggctgttc ctccctggct gtgtgcccac cagccccagg gctatgtggc ccagggccta  16920
tcttgctgcc aggcccacct gcaggagggt caggtggggc cttccaaggg cacagagctg  16980
ttccctgggg ctcgggatgc ccctgactcg caccccttctc acacagatca acttcttcat  17040
cttcgtccgc atcgttcagc tgctcgtggc caagctgcgg gcacggcaga tgcaccacac  17100
agactacaag ttccggtggg tgccgcggca gctggcgtct cgagacctgg agaccctcag  17160
ggccagaggg cagctggggg tggggactcc aagctccacg tggatggtgc gggccgaggg  17220
tgggggcggt gggtgactca ggcgctgcct ctgcaggctg gccaagtcca cgctgaccct  17280
catccctctg ctgggcgtcc acgaagtggt cttcgccttc gtgacggacg agcacgccca  17340
gggcaccctg cgctccgcca agctcttctt cgacctcttc ctcagctcct tccaggtgcc  17400
cgcccgcccg ccggctcccc cgcccggggc gcagtgtgcc acccctgacc accctgtctc  17460
tccagggcct gctggtggct gtcctctact gcttcctcaa caaggaggta ggtgggagtg  17520
ggggcatctg agaccatcag cactggccgt cggggtcagg ggcagagaga ggcacaggga  17580
tgccagcccc acccctgccc gggggttgga acacgtgggg cccaagcctt tccctccccc  17640
tgctcttatt gggtgcagtt gccatggcgc tgggtgtcag gcccccagga caggttggcc  17700
tcagccccat cgctacggtg tccaccgtgg gggtccccag gtgtctgcag actgctttcc  17760
gtggcgatgc tgggtggcat agctgtgccc agcagggagc ttgtgtcgct ctgcacccct  17820
cagagcggag actgggcatc tccgatgagg cccacagcag gtcccggtgg ggtggagagg  17880
acaggcaggc cctaggactg gcctgccccg tccccctccc caggtgcagt cggagctgcg  17940
```

-continued

```
gcggcgttgg caccgctggc gcctgggcaa agtgctatgg gaggagcgga acaccagcaa  18000
ccacagggcc tcatcttcgc ccggccacgg ccctcccagc aaggagctgc agtttgggag  18060
gggtggtggc agccaggatt catctgcgga gaccccccttg gctggtggcc tccctagatt  18120
ggctgagagc cccttctgaa ccctgctggg accccagcta gggctggact ctggcaccca  18180
gagggcgtcg ctggacaacc cagaactgga cgcccagctg aggctggggg cgggggagcc  18240
aacagcagcc cccacctacc ccccaccccc agtgtggctg tctgcgagat tgggcctcct  18300
ctccctgcac ctgccttgtc cctggtgcag aggtgagcag aggagtccag ggcgggagtg  18360
ggggctgtgc cgtgaactgc gtgccagtgt ccccacgtat gtcggcacgt cccatgtgca  18420
tggaaatgtc ctccaacaat aaagagctca agtggtcacc gtgcatgtcc tggaaagcag  18480
ggctggaaat gctggggccg aagcagtggg ggatggaaca gcggtgggtg gtcagcgcca  18540
gtgcgggctg ttgaagggtc cccctgctgt cccagttcac tcagagttgg cactggaacc  18600
ccggaggatc ccgaaggcag ccagcctgtg cccatctgag caggtcctgg ccaccttccc  18660
atcctggttc tggcgggcag tccccctgga cgctttggcc accagagggt caccattcac  18720
cagcagagac gtgaggggca cagtggctaa ggcggcatga ggcatcacag tcccctgacc  18780
gaccccatca gcactggatt cacccgaggg cgtcttctcc ctggaggccg tgaggacact  18840
ggcacctggc tcatcggccc gcccttcctc tgagcctcct ggcctccgtt tcatctcagc  18900
tccagccccc tcggcaattt acaggccacg tagcagattg aagcgggaag aaatgggcct  18960
gaacattgcc gcgggtccag gcgacggagg agggcaggtt gcccaacttc tgcacaggac  19020
ccggggtgcg ccacacacac gccagtcctc gtgccacaca gagaggtccg gcctacgcca  19080
gtcctcgtgc cacacagaga ggtccggcct acgccagtcc tcgtgccaca cagagaggtc  19140
cggcctacgc cagtcctcgt gccacacaga gaggtccggc ctacgccagt cctcgtgcca  19200
cacagagagg tccggcctac gccagtcctc gtgccacaca gagaggtccg gcctacgcca  19260
gtcctcttgc cacctcgtgg tgggtgggcg ccctgcttgc cagccaggga gcaccaggaa  19320
agagctgcct cctgcgtgct ggacacagga ggtgcttcag ggtggggtct cccattgtgt  19380
ggggcccaac ctgagtctaa gggcccaggg accacacagc gggggtggag acaaattcag  19440
ggtagaagct gtgaggggcc tgtggtcagc cccccggggg gtccctgcag caggcactgt  19500
gagacctact gaggtgtgtg catgggctgg ggaaggagcc agtcaggtgc ccctgctctg  19560
aggagctgct gggaagtgct gctgggccct gggggaaggg gtgctcacag cccctgcctg  19620
ggccacgtgg gctggagccg ctcaggcaga gccggactaa ttggggcaaa tgaggggaca  19680
ggaggcctct gaggaaaggt aaatagaatt actcacccgc caggcactgg ggccctcctg  19740
ggggggccct caccctgcca cccaccacag ggcctgcatg cagcagggag ggaagtgagc  19800
tgattaggca aggctggacc cttctggggc cctggggttg ctgtgattgg gacggcaagg  19860
ccaggagacg gtcccctgag ctgcacctgc tggaggcctg tgatctcaga ccttaaggct  19920
tcaggccagc tctacgcccc tccggcctca ggtcctggct ctcctctgag ccctggatgc  19980
ccgggtgcct gtgtgggcac gaggctgctc cgagtcagca cacggaggtg gacattctcc  20040
ttcatgccag ctgagctcag ggctggtgac tgccctgggg aaactgcccc tcacctggga  20100
cctcctgaca gccctcccca ttcccgagtc cctctgccct tgtcctcttt cacctctgtc  20160
ccgccctcat ccctaaggga actggagcag gctggtggag ttgggtggag ttggggactg  20220
gcagggggtg gactcaccca ggcaataaac actggcccta accaggcagt cctgcaggca  20280
ggtaggtgga gggactgttt tttttctttt ttggagatag agtctcactc tgttgcccaa  20340
```

-continued gttggagtgc agtggcatga tcttggctca ctgcaaactc cacctcccag gttcatgtga 20400
ttctctgcct cagcctcccg agtagctggg attataggcg tgtgccacga cacctggcta 20460
attttttttt tttttttttt gagacggagt ttcactctcg ttgcccaggc tggagctcaa 20520
tggcgcgatc tcagctcacc gcaacctccg cctcccaggt tcaagcgatt ctcctgcctt 20580
agcctcccta gtagctggga ttacaggcag gtatgtgatg cccggcatcc caaaggggta 20640
tctgcaagag ttgggtgctg tgtgtgcatg gctgggagga agatgacttt gataccctgg 20700
aatctggtgt ctgtggacac aaaaatacta ctaaaatgag agtggagacc aggaaaaagg 20760
aagacatgaa ctacatgaag gaccaaatct aggagagtca gaagtgcgtc acaggaatag 20820
gggaccttga gccagacaga aggctcagca gagacaccct caaggggatg aaagggattg 20880
agtgcactaa tatttagagg agagagttca ggacttgatt agtgactagt acatagaaaa 20940
ctaaacaaat gaggctgggt gcagtggctc atgcctgtaa tcccagcact ttgggggggcc 21000
aaggcgggcg aatcacctga ggtcaggagt tcgagaccag cctggccaac atggtgaaac 21060
ctcgtctcta ctgaaaatac aaaaattagc cgggcgtggt ggcgggcgcc tgtagtccca 21120
gctacttggg agcctgaggc aggagaatcg cttgaacctg ggaggcggag gctgctgtga 21180
gccaagatgg tgccattgca ctccaccctg ggtgacagag caagactccg tctcaaaaaa 21240
aaaaaaaaag aaagaaaaaa ccaagcaaat gaaaaaagaa ggcaattaat aattccaaag 21300
aaaagaaaaa tttgggcaga aaagaacaaa acaagcagaa tttaccatga ctcagttctg 21360
aatacaaaca cagacatcat aatgtaaaca ccaacactga tgcaaccaga atcatgggag 21420
aaaaaagatc tagggagggt ggtggacggg aatatcacgt atgtactggg ggtaggggag 21480
agaacaaaat gggaaaaatc aagaataatt cacgttagaa ataaaaatac agagcaaaat 21540
ttaaaaatgc aaagaatgag gtgaagagtt caaagtggtc acctcggggc cgggcgcggt 21600
ggctcacgcc tgtgatccca gcactctggg aggctgaggc gggcggatca caaggccagg 21660
agtttgagac catcctggct aacaaggaga aaccccatct ctactaaaaa ttagccaggc 21720
gtggtggtgg gcgcctgtag tcccagctac tcgggaggct gaggcaggag aatggcgtga 21780
acccaggagg cgcagcttgc agtgagccga gatcgcgcca ctgcactcca gcttgggcaa 21840
cagagtgaga ctccgcctca aacaaaacaa aacaaaacaa aaaaacaaag tggtcatctc 21900
taggcaaggt gggtgggaga tggctagggc tgcaggtcca ctacgtgagc tggctcagcc 21960
tatccccaga caccctgcac tcactcagcc cggggtcctc cccctgcact cactcagccc 22020
cgggtcctcc cctgcactca ctcagccccg ggtcctcccc ctgcactcac tcagccccgg 22080
gtcctcccct gcctgctctt tctctgaccc tgccctccac tgttcctttt tcttctttct 22140
ctccctgttg tgtccaggaa ccaggcacca ccctcatttc ttcttgatca atctttaaaa 22200
accagcagtg ctcagctaac tcttcatcta tctcccccga cctggggctc tgctgaatcc 22260
acgctttaga cccagctatc agctcggcat gtacagctgg atgtccacac cgagctgctc 22320
accctgtccc cagcttcttc ctcccactgt ccactgcaga agcctcctaa caggacccct 22380
gctgctaccc cggaccctgc aacccattcc cacacagcag ccagatgctt tgacacccga 22440
agtctcctat gaatccgatg aggcctctgc accacacctc attttacaga agtacagggg 22500
aaacaggggt ctgttgacac cacagagatg cagctggcca aaggcagaat gtggggtaca 22560
cgactgtcaa acgccagggg tccttacacg aatggtggaa aaagaggggc atgttacgga 22620
tggaggctcg ggacacatgg gcgccgcctt cccatgctgc cagcaaccca ccaggaacct 22680

-continued

```
attaatttag tcatttggga aatgggagct gggtatatcg gctattagga aattgttcat  22740
gctcaataag tattaattac aattttcata agagcttaac ccccctgaaa gaggtcactg  22800
tttcctcact tgtaaattgg gatactaaaa cctgccccat ggagttgcca gagtgacgtg  22860
tgtgcgtgca caccaacagt acacagcaga tagtgacata tgtgtgcacg ccaacactac  22920
acagcagata gtgacttgtg cgtgcgcgcc aacactacac agcagtgaca cgtgcgtgca  22980
caccaacagt acccagcaga tagtgacatg tgtgcacgcc aacactacac agcagatagt  23040
gacttgtgcg tgcacgccaa cactacacag cagatagtga catgtgcgtg cacgccaaca  23100
ctacacagca gatagtgacg tgtgtgcacg ccactacaca gcatagtgac ttgtgtgtgc  23160
acgccaacac tacacggcag atagtgactt gtgtgtgcac gccaacacta cacggcagat  23220
agtgacttgt gtgtgcacgc caacactaca cggcagatag tgacttgtgt gtgcacgcca  23280
acactacacg gcagatagtg acttgtgtgt gcacgccaac actacacggc agatagtgac  23340
ttgtgtgtgc acgccaacac tacacggcag atagtgactt gtgtgtgcac gccaacacta  23400
cacggcagat agtgacttgt gtgtgcacgc caacagtaca cagcagatag tgacatatgt  23460
gtgcacgcca acactacacg gcagatagtg atgtgtgtgc acaccaacac tacacagcag  23520
atagtgacat gcgcgtgcac gccaacacta cacagcaggt agtgacatgt gtgtgcacac  23580
caacagtaca cagcagatag tgacatgcgc gtgcacacca acactacaca gcagatagtg  23640
atgtgtgtgc acaccaacag tacacagcag attgtgatgt gtgtatgcac accaacggta  23700
caacacgcaa cagttgcagt tgcctcattt ccccaagtcg ccctcactgc agaaagggga  23760
gtgtctccag ctgcttagtc cagcagcctc caggattggg tgagggtcgg aggccctggt  23820
gccctgcatg gacaaggcag tggcagcagg gctgaaggac aggctggggt gggaggaccg  23880
caaccctctg ggatcgggcc ccacggtcag tcccgcagcc caggggagag gtgcccactc  23940
tagcagccct ttatgtgctc ctcaagctga aagtagagac cccgctttgt gactacagtg  24000
agttctcaca ccattaggcg aatggctggg gtaagaccac cctgtggccc ctgcagagct  24060
gacctcactg ggtggtccac cgaagagggg atgggagggc aagtttgctt cagggtcaga  24120
ggtccggtcc cggtggtgca cctccccagc cctcaggtag gttaggcccc ctctcccgcg  24180
tcccctcccc ctcctcaccc caatccccat cccccacgcg gtgcatcggg tgaaggggtg  24240
gggcctccag caacaccgtg ggctcagcgc tccccacagg ctcctaccct cctgcccagc  24300
atgtgcctgg ccaggccggc cccctcctct gaagggttct tggcagaaag atctccaaat  24360
tgaaggtttc tggtggcagg cccaggtgct ggggccatac ctgggggagc tccacccccc  24420
ggctgtaggt aggcaaggcc cggattccag ggcccagtgt aagatgaccc aggtgagccc  24480
aaatcaggtc catctcttaa cacaaggagc tccctcggca cctcctgtgt gctacacagg  24540
ggtcccagca cccatgcagg ggagaggcct ttggatcacc acagcccaca ctctgtacag  24600
agggataaac taccgctttg cctgtagagt agccattctt ttatttattt ttttcttttt  24660
cttttttttt tttttttttt tgagacggag tcttgctctg ttgcccaggc cggagtgcag  24720
tggcgcaatc tcagctcact gcaacctccg cctcccgggt tcaagtgatt ctcctgcctc  24780
agcttcccga gtaactggga ttataggtgc ctgccaccac acccagctaa tttttatgtt  24840
tttagtagag acggggtttc accgtgttag ccaggatagt ctcaatctcc tgaccttgtg  24900
atccacccgc ctcagcctcc caaagcgatg gaatcacagg cgtgaaccac cgcacccggc  24960
cctaactttt ctatttttag tagaaatggg gtttcaccat attggccagg ttggtctcaa  25020
actcctgacc ttgtgatccg cccgcctcag cctcccaaag tgctggaatt acaggcgtga  25080
```

-continued

```
accaccgcac ctggcccctt ttctttaata aatttgctta aaaaaaaaaa agaaccca    25138
```

<210> SEQ ID NO 19
<211> LENGTH: 2378
<212> TYPE: DNA
<213> ORGANISM: H. sapiens
<220> FEATURE:
<220> FEATURE:
<221> NAME/KEY: CDS
<222> LOCATION: (2370)...(2378)

<400> SEQUENCE: 19

```
cctctagagt caacatgaca ggcatcgaat ggctcctgtt tctctggcag agttgggggc      60
agagccaggc ttggccacgc tgggctctaa ggggctgtca ttttgcccag ggagctcctg     120
gctgggtggt cctcccccca gggtgagcac gcgtcccccc cacccccact tcgaggcgcc     180
caggcaggga acagctcatt ggccagtgtc cttcctcctt gtccccgcct gcatctccac     240
catccaccct gctccagctg ccccttgtcc ctctccccgt cccctgccca gagccccagg     300
tctcccctgc acccctgagc ctgcccacct agcagtgccc ctcgtccagg gcccctctgg     360
gttgggggtg cacacagcgg ggagaggcgg ctcctgctgc tcctcaccca gcccggctca     420
gtggccggag ccgcccagga cagtggcagt agatggggct gtttgatcag gatcagggaa     480
gataaggccc cttgcgtgac cccagagctg gggacgccaa aactgcccct cttccccyac     540
ccgcctgccg ctgtctctgc cagggagagg cccctactct gtgggtcctt cgccccagca     600
ccaagcctgc atggctgctc acctggctca ggaactgggg atcagcgaca cacgggtcct     660
gcctcccatc ggcccctaca tgagcccagg gtccaagggc tgaggttggg agctctttag     720
cagtctgtga cgcaggtgcc tgtccctgtc attcagctgt cacactgctt ggggcatctc     780
aggccccgtt agcggggcag ccctgggtgg agctggcccc acgcgggctc acccagccgc     840
tacctggagg aggctaaaat ccaggctgtc ccgtggcagc cagcagtcca ggcctgcccg     900
gaaaccctct gctccagctg cagccttcgc ccatctcctt gcccctctcc ctggcttccc     960
cctggcactg ccttccagct ggctggccct ccatctgccc agccatccat ccacacctct    1020
tattccattt gagggtgccc caaagaagag cccgtaacag cccgggggct catagccagc    1080
cactcgcggg accccgcaca tgcacgtgga cccacaggaa gaccctccct gcttctccca    1140
cagaattcag ttggtgcaga aactgggctc tgtagcaacg aaaggccgat ttgtgtagct    1200
gttgccaccc cgaactccca gctcagatgc tggctgtggc atggggacca ggggctgtga    1260
ctcccacagc cctggcaggc accacggggg atgtcctccc caccctgtgc ccccacccta    1320
ggccagctcc tcctccaagt cgacgcccgc agtgctaacc tcaaaggact gtgcagccag    1380
cctgtggcgt cccatgggat ccaggaagcc caaccgagcc ttgcacggca cccacgaggc    1440
acctaggcac cccggtgctg ggcagggggc acacatgtga cacagacccc tgagtgtggg    1500
ccccacacac ttggcctggc acagctgcaa gccagcccag ccactttgct cgctgtggca    1560
ctggggccaa gtgatggaag gtccaggcat cgccaccctc acgcttggca cattggctca    1620
ggtcagcctg gcaagccagc tttcccaggg gctaagaata ggtgaggagg atggtgagga    1680
agcacgccgg ggggctgtca actgagggag gaggtcacca tctggggagg ctggtcgccc    1740
caagagcatt gggtcacctg caggaaggtg gctgccacca gcaatgagac gaggggctct    1800
gcgaccctca gagctgccag ccagccagcc ctgggtggca agagtgactc ctcctggggt    1860
ctcctccctc ctatcgccct cttttttttt ttttttttt ttgagacgga gtctcgctct    1920
```

-continued

```
gcacagctga ctgcaatgct gatctcgctc actgcaaggt ctgccccggg ttcacgccat   1980

tctcactgcc acaagctccc gagtagctgg actacagacg cccgccacca cgcctggcta   2040

atttttgta tttttagtta gagacggggt ttcactgtgt agcggatggt ctcgatctcc   2100

agacctccgt tgatccaccc ccctcggcct cccaagttct gggaaacagg cgtgagcgcc   2160

gcgcccggcc cccagctccc tctttatccc taggaccctg aggctcagag gggcagcttc   2220

aggggaggac accccactgg ccagacgccc caggctctgc tgctctgcca ctcagctgcc   2280

ctcggaggag cgtacacaca caccaggact gcattgcccc agctgtgcag cccctgccag   2340

atgtgggagg cagctagctg cccagaggc atg ccc ccc                        2378
                                Met Pro Pro
                                  1
```

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20 ccgcatctcttgaacacgaa 20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
ttgagcctca gggcccgcgc 20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
gtgtcctccc ctgaagctgc 20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
gagtggcaga gcagcagagc 20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
tgtgtgtgta cgctcctccg 20

-continued

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
tcctggtgtg tgtgtacgct 20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
aatgcagtcc tggtgtgtgt 20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
ctgggcagct agctgcctcc 20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
ggcatgcctc tgggcagcta 20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ccagcaggaa tacttgtcga 20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
ggacctgtgg ctggcaggcc 20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 31
aagtccatca cctgagcgga 20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
tctcaaacag gaagtccatc 20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
ccacttctca aacaggaagt 20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
cactggtcac cgtagagctt 20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
ggtgacactg gtcaccgtag 20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
cacaccagct ccgtgggagg 20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
aggttctgtt gcacaccagc 20

<210> SEQ ID NO 38
<211> LENGTH: 20

-continued

<212> TYPE: DNA
<213> ORGANISM: Artificial Sequence
<220> FEATURE:
<223> OTHER INFORMATION: Antisense Oligonucleotide

<400> SEQUENCE: 38
atacttgtcg aaggttctgt 20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
cggtgttgca ctttgtggtg 20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
ccctggcaga gacagcggca 20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
cttgaacacg aagcggtgtt 20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gggcccgcat ctcttgaaca 20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
cttctgcgag ttacagtggc 20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44

-continued ctggacctca atctcctcgc 20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
tccttctgga cctcaatctc 20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
ggccacctcc ttctggacct 20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
catcttggcc acctccttct 20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
gaagctgctg tacatcttgg 20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
cccccaggat ggccaaggcg 20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
acggagctgg ctttcagcac 20

<210> SEQ ID NO 51
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 51

ctgtagcggg tcctgagcag                                              20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52

ttctggctgt agcgggtcct                                              20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53

gccaattttc tggctgtagc                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54

tgaggtcgtc gccaattttc                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55

tgctgacact gaggtcgtcg                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56

gccaggtgct gacactgagg                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57

cacgatgcca tattgcatga                                              20
```

-continued

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
gtggccaggc ccagcaggtt 20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
cagacacttg accactgccc 20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ccgcaggatc caccagaagc 20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
tgatcaggat ggccaggaag 20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
ggacgaagat gaagaagttg 20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
cgcagcttgg ccacgagcag 20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 64
tgcatctgcc gtgcccgcag 20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
acttgtagtc tgtgtggtgc 20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
aggtcgaaga agagcttggc 20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
gcactttgcc caggcgccag 20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
ctcctcccat agcactttgc 20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
aaactgcagc tccttgctgg 20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
atgaatcctg gctgccacca 20

<210> SEQ ID NO 71

-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
ctagggaggc caccagccaa 20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
tctcagccaa tctagggagg 20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
tcccagcagg gttcagaagg 20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
ttcctgcagg tgacccaatg 20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
tctcgcagac agccacactg 20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
agaggaggcc caatctcgca 20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77

-continued tgcaccaggg acaaggcagg 20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
tggactcctc tgctcacctc 20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
tggcacgcag ttcacggcac 20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
acatgggacg tgccgacata 20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
tttccatgca catgggacgt 20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
gttggaggac atttccatgc 20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
cacggtgacc acttgagctc 20

<210> SEQ ID NO 84
<211> LENGTH: 20
<212> TYPE: DNA

-continued

<213> ORGANISM: Artificial Sequence
<220> FEATURE:
<223> OTHER INFORMATION: Antisense Oligonucleotide

<400> SEQUENCE: 84
agatgtccgt gtttgtcagc 20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
taataacttt ttaaagaagg 20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
tactacgttg ctcgggctgg 20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
agctctgtgg ctcagttacc 20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
gtgcagcttg ctgtggcaca 20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
cagcaaccgc ttggtacagg 20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
agaagttgat ctgtgtgaga 20

-continued

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
ccagcaggcc ctggagagac 20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
cctttgagcc tcagggcccg 20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
gcccctttga gcctcagggc 20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
agctgagtgg cagagcagca 20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
gcagctgagt ggcagagcag 20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
tgtgtgtacg ctcctccgag 20

<210> SEQ ID NO 97
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 97
ggtgtgtgtg tacgctcctc 20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
ctggtgtgtg tgtacgctcc 20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
gggcaatgca gtcctggtgt 20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
ctagctgcct cccacatctg 20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
cagctagctg cctcccacat 20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
cctctgggca gctagctgcc 20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
gcatgcctct gggcagctag 20

-continued

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
cctgtggctg gcaggccagc 20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
ttccacttct caaacaggaa 20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
gcttccactt ctcaaacagg 20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
gtagagcttc cacttctcaa 20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
cgtagagctt ccacttctca 20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
ttgtggtgac actggtcacc 20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 110
agcaggctca ggttgtggtg 20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
ttgcactttg tggtgccaag 20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
gttgcacttt gtggtgccaa 20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
tgttgcactt tgtggtgcca 20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
gtgttgcact ttgtggtgcc 20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
ggcccgcatc tcttgaacac 20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
gtcgggcccg catctcttga 20

<210> SEQ ID NO 117
<211> LENGTH: 20

-continued

<212> TYPE: DNA
<213> ORGANISM: Artificial Sequence
<220> FEATURE:
<223> OTHER INFORMATION: Antisense Oligonucleotide

<400> SEQUENCE: 117
tgggaggcat cacgccaagg 20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
catctggcac tgggaggcat 20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
cttggccacc tccttctgga 20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
tacatcttgg ccacctcctt 20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
cctggaagct gctgtacatc 20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
attcgcgtgg atggcattgc 20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123

-continued agcccatcaa tgaccagcac 20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
gcgggtcctg agcagcccat 20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
ggtcgtcgcc aattttctgg 20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
acactgaggt cgtcgccaat 20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
ggtgctgaca ctgaggtcgt 20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
atgccatatt gcatgaacac 20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
gagggtggcc aggcccagca 20

<210> SEQ ID NO 130
<211> LENGTH: 20
<212> TYPE: DNA
<213> ORGANISM: Artificial Sequence -continued
<220> FEATURE:
<223> OTHER INFORMATION: Antisense Oligonucleotide

<400> SEQUENCE: 130
aacagacact tgaccactgc 20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
gaacagacac ttgaccactg 20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
gttgtcattg ctggtccagc 20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
agaagcccat gttgtcattg 20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
gggaaccgca ggatccacca 20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
gcggacgaag atgaagaagt 20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
agatgaatcc tggctgccac 20

-continued

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
ccagagtcca gccctagctg 20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
gggtgccaga gtccagccct 20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
tctgggtgcc agagtccagc 20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
ctctgggtgc cagagtccag 20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
cctctgggtg ccagagtcca 20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
acgcctctgg gtgccagagt 20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
cagttctggg ttgtccagcg 20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
aggcccaatc tcgcagacag 20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
gaggcccaat ctcgcagaca 20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
ggagaggagg cccaatctcg 20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
tgcagggaga ggaggcccaa 20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
tctgcaccag ggacaaggca 20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
tgctcacctc tgcaccaggg 20

<210> SEQ ID NO 150

-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
tctgctcacc tctgcaccag 20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
gactcctctg ctcacctctg 20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
gccctggact cctctgctca 20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
gcagttcacg gcacagcccc 20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
cgcagttcac ggcacagccc 20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
gggacactgg cacgcagttc 20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156

-continued gcacatggga cgtgccgaca 20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
aggacatttc catgcacatg 20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
ggaggacatt tccatgcaca 20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
gctctttatt gttggaggac 20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
gagctcttta ttgttggagg 20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
accacttgag ctctttattg 20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
ggcagttttg gcgtccccag 20

<210> SEQ ID NO 163
<211> LENGTH: 20
<212> TYPE: DNA

-continued

<213> ORGANISM: Artificial Sequence
<220> FEATURE:
<223> OTHER INFORMATION: Antisense Oligonucleotide

<400> SEQUENCE: 163
gagcttcctg cctcttcacg 20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
ggataggatg tgcgtgtcta 20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
ctctctgcct ccgatttctt 20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
acaccagctc tgcagggtag 20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
cacctccttc tgcgagttac 20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168
gcctctgggc agctagctgc 20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
tggcaggcca gcagcagcag 20

-continued

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170
tggctggcag gccagcagca 20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
tccatcacct gagcggaggg 20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
gaagtccatc acctgagcgg 20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
acaggaagtc catcacctga 20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174
cacttctcaa acaggaagtc 20

<210> SEQ ID NO 175
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175
tgacactggt caccgtagag 20

<210> SEQ ID NO 176
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 176
gtggtgacac tggtcaccgt 20

<210> SEQ ID NO 177
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 177
ggttgtggtg acactggtca 20

<210> SEQ ID NO 178
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 178
ggctcaggtt gtggtgacac 20

<210> SEQ ID NO 179
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 179
tacttgtcga aggttctgtt 20

<210> SEQ ID NO 180
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 180
caggaatact tgtcgaaggt 20

<210> SEQ ID NO 181
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 181
tgttggccgt ggtattggcg 20

<210> SEQ ID NO 182
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 182
gagatgttgg ccgtggtatt 20

-continued

<210> SEQ ID NO 183
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 183
caggagatgt tggccgtggt 20

<210> SEQ ID NO 184
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 184
gcactttgtg gtgccaaggc 20

<210> SEQ ID NO 185
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 185
gcggtgttgc actttgtggt 20

<210> SEQ ID NO 186
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 186
cgaagcggtg ttgcactttg 20

<210> SEQ ID NO 187
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 187
aacacgaagc ggtgttgcac 20

<210> SEQ ID NO 188
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 188
atctcttgaa cacgaagcgg 20

<210> SEQ ID NO 189
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 189
gggtccacgc acccactgac 20

<210> SEQ ID NO 190
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 190
acgccaaggc tgcccccggg 20

<210> SEQ ID NO 191
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 191
cacctccttc tggacctcaa 20

<210> SEQ ID NO 192
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 192
tggaagctgc tgtacatctt 20

<210> SEQ ID NO 193
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 193
cacctggaag ctgctgtaca 20

<210> SEQ ID NO 194
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 194
acatcacctg gaagctgctg 20

<210> SEQ ID NO 195
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 195
gtgtacatca cctggaagct 20

<210> SEQ ID NO 196
<211> LENGTH: 20

-continued

<212> TYPE: DNA
<213> ORGANISM: Artificial Sequence
<220> FEATURE:
<223> OTHER INFORMATION: Antisense Oligonucleotide

<400> SEQUENCE: 196
ccccagggac aggctgtagc 20

<210> SEQ ID NO 197
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 197
ggcccccagg gacaggctgt 20

<210> SEQ ID NO 198
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 198
cgggtcctga gcagcccatc 20

<210> SEQ ID NO 199
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 199
gtagcgggtc ctgagcagcc 20

<210> SEQ ID NO 200
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 200
ggctgtagcg ggtcctgagc 20

<210> SEQ ID NO 201
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 201
ccgctccatc actgagccag 20

<210> SEQ ID NO 202
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 202

-continued gccaccgctc catcactgag 20

<210> SEQ ID NO 203
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 203
catgaacacc gcggccacac 20

<210> SEQ ID NO 204
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 204
attgcatgaa caccgcggcc 20

<210> SEQ ID NO 205
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 205
gccatattgc atgaacaccg 20

<210> SEQ ID NO 206
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 206
cccagcaggt tgtgcaggta 20

<210> SEQ ID NO 207
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 207
gccaggccca gcaggttgtg 20

<210> SEQ ID NO 208
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 208
ggtggccagg cccagcaggt 20

<210> SEQ ID NO 209
<211> LENGTH: 20
<212> TYPE: DNA
<213> ORGANISM: Artificial Sequence -continued
<220> FEATURE:
<223> OTHER INFORMATION: Antisense Oligonucleotide

<400> SEQUENCE: 209
aggctgaaga agctcctctc 20

<210> SEQ ID NO 210
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 210
gtagaggctg aagaagctcc 20

<210> SEQ ID NO 211
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 211
ccaggtagag gctgaagaag 20

<210> SEQ ID NO 212
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 212
gatgcccagg tagaggctga 20

<210> SEQ ID NO 213
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 213
agccgatgcc caggtagagg 20

<210> SEQ ID NO 214
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 214
tgtcattgct ggtccagcac 20

<210> SEQ ID NO 215
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 215
atgttgtcat tgctggtcca 20

-continued

<210> SEQ ID NO 216
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 216
gaagcccatg ttgtcattgc 20

<210> SEQ ID NO 217
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 217
ccaccagaag cccatgttgt 20

<210> SEQ ID NO 218
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 218
gatccaccag aagcccatgt 20

<210> SEQ ID NO 219
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 219
gaaccgcagg atccaccaga 20

<210> SEQ ID NO 220
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 220
caggatggcc aggaagacgg 20

<210> SEQ ID NO 221
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 221
gatcaggatg gccaggaaga 20

<210> SEQ ID NO 222
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 222
tgaagaagtt gatcaggatg 20

<210> SEQ ID NO 223
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 223
agatgaagaa gttgatcagg 20

<210> SEQ ID NO 224
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 224
gtagtctgtg tggtgcatct 20

<210> SEQ ID NO 225
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 225
cttgtagtct gtgtggtgca 20

<210> SEQ ID NO 226
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 226
gaacttgtag tctgtgtggt 20

<210> SEQ ID NO 227
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 227
ggtcgaagaa gagcttggcg 20

<210> SEQ ID NO 228
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 228
agaggtcgaa gaagagcttg 20

<210> SEQ ID NO 229

-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 229
tgaggaagag gtcgaagaag 20

<210> SEQ ID NO 230
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 230
tagggaggcc accagccaag 20

<210> SEQ ID NO 231
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 231
acctggaagc tgctgtacat 20

<210> SEQ ID NO 232
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 232
gcagcaggct caggttgtgg 20

<210> SEQ ID NO 233
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 233
ctgaggaaga ggtcgaagaa 20

<210> SEQ ID NO 234
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 234
aggttgtggt gacactggtc 20

<210> SEQ ID NO 235
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 235

-continued gttgatcagg atggccagga 20

<210> SEQ ID NO 236
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 236
caggtagagg ctgaagaagc 20

<210> SEQ ID NO 237
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 237
cgcatctctt gaacacgaag 20

<210> SEQ ID NO 238
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 238
gaagcggtgt tgcactttgt 20

<210> SEQ ID NO 239
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 239
aatacttgtc gaaggttctg 20

<210> SEQ ID NO 240
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 240
ggccaggccc agcaggttgt 20

<210> SEQ ID NO 241
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 241
ccgatgccca ggtagaggct 20

<210> SEQ ID NO 242
<211> LENGTH: 20
<212> TYPE: DNA

-continued

<213> ORGANISM: Artificial Sequence
<220> FEATURE:
<223> OTHER INFORMATION: Antisense Oligonucleotide

<400> SEQUENCE: 242
agatgttggc cgtggtattg 20

<210> SEQ ID NO 243
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 243
caggttgtgg tgacactggt 20

<210> SEQ ID NO 244
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 244
ggaagaggtc gaagaagagc 20

<210> SEQ ID NO 245
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 245
tggtgacact ggtcaccgta 20

<210> SEQ ID NO 246
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 246
gctcaggttg tggtgacact 20

<210> SEQ ID NO 247
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 247
tgcactttgt ggtgccaagg 20

<210> SEQ ID NO 248
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 248
atcacctgga agctgctgta 20

-continued

<210> SEQ ID NO 249
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 249
tattgcatga acaccgcggc 20

<210> SEQ ID NO 250
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 250
atcaggatgg ccaggaagac 20

<210> SEQ ID NO 251
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 251
tctcttgaac acgaagcggt 20

<210> SEQ ID NO 252
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 252
tcttgaacac gaagcggtgt 20

<210> SEQ ID NO 253
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 253
tggccaggcc cagcaggttg 20

<210> SEQ ID NO 254
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 254
tctggctgta gcgggtcctg 20

<210> SEQ ID NO 255
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 255
ggagatgttg gccgtggtat 20

<210> SEQ ID NO 256
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 256
tgcctctggg cagctagctg 20

<210> SEQ ID NO 257
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 257
tagaggctga agaagctcct 20

<210> SEQ ID NO 258
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 258
gtccatcacc tgagcggagg 20

<210> SEQ ID NO 259
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 259
aacttgtagt ctgtgtggtg 20

<210> SEQ ID NO 260
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 260
gtcccagcag ggttcagaag 20

<210> SEQ ID NO 261
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 261
tgcatgaaca ccgcggccac 20

-continued

<210> SEQ ID NO 262
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 262
ccaggcccag caggttgtgc 20

<210> SEQ ID NO 263
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 263
aggtagaggc tgaagaagct 20

<210> SEQ ID NO 264
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 264
cagaagccca tgttgtcatt 20

<210> SEQ ID NO 265
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 265
catgttgtca ttgctggtcc 20

<210> SEQ ID NO 266
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 266
ggcccagcag gttgtgcagg 20

<210> SEQ ID NO 267
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 267
tcaggttgtg gtgacactgg 20

<210> SEQ ID NO 268
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 268
agcccatgtt gtcattgctg 20

<210> SEQ ID NO 269
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 269
cttctcaaac aggaagtcca 20

<210> SEQ ID NO 270
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 270
tgaacacgaa gcggtgttgc 20

<210> SEQ ID NO 271
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 271
tccacttctc aaacaggaag 20

<210> SEQ ID NO 272
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 272
aggaagtcca tcacctgagc 20

<210> SEQ ID NO 273
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 273
gccgatgccc aggtagaggc 20

<210> SEQ ID NO 274
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 274
ggaaccgcag gatccaccag 20

<210> SEQ ID NO 275
<211> LENGTH: 20

-continued

<212> TYPE: DNA
<213> ORGANISM: Artificial Sequence
<220> FEATURE:
<223> OTHER INFORMATION: Antisense Oligonucleotide

<400> SEQUENCE: 275
agtccatcac ctgagcggag 20

<210> SEQ ID NO 276
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 276
gatgaagaag ttgatcagga 20

<210> SEQ ID NO 277
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 277
cagcaggaat acttgtcgaa 20

<210> SEQ ID NO 278
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 278
gccagcagga atacttgtcg 20

<210> SEQ ID NO 279
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 279
ggctggcagg ccagcagcag 20

<210> SEQ ID NO 280
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 280
accgcaggat ccaccagaag 20

<210> SEQ ID NO 281
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 281

-continued agcgggtcct gagcagccca 20

<210> SEQ ID NO 282
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 282
cgggcccgca tctcttgaac 20

<210> SEQ ID NO 283
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 283
cggaacttgt agtctgtgtg 20

<210> SEQ ID NO 284
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 284
ggatccacca gaagcccatg 20

<210> SEQ ID NO 285
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 285
ggtcccagca gggttcagaa 20

<210> SEQ ID NO 286
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 286
aaccgcagga tccaccagaa 20

<210> SEQ ID NO 287
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 287
ggcagcaggc tcaggttgtg 20

<210> SEQ ID NO 288
<211> LENGTH: 20
<212> TYPE: DNA
<213> ORGANISM: Artificial Sequence -continued
<220> FEATURE:
<223> OTHER INFORMATION: Antisense Oligonucleotide

<400> SEQUENCE: 288
gatgttggcc gtggtattgg 20

<210> SEQ ID NO 289
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 289
gaatacttgt cgaaggttct 20

<210> SEQ ID NO 290
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 290
gaagttgatc aggatggcca 20

<210> SEQ ID NO 291
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 291
tcacctggaa gctgctgtac 20

<210> SEQ ID NO 292
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 292
ccatattgca tgaacaccgc 20

<210> SEQ ID NO 293
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 293
tagcgggtcc tgagcagccc 20

<210> SEQ ID NO 294
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 294
ctctgggcag ctagctgcct 20

-continued

<210> SEQ ID NO 295
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 295
tcaaacagga agtccatcac 20

<210> SEQ ID NO 296
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 296
caccagaagc ccatgttgtc 20

<210> SEQ ID NO 297
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 297
tgtacatcac ctggaagctg 20

<210> SEQ ID NO 298
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 298
atgttggccg tggtattggc 20

<210> SEQ ID NO 299
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 299
cgatgcccag gtagaggctg 20

<210> SEQ ID NO 300
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 300
aggatccacc agaagcccat 20

<210> SEQ ID NO 301
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 301
tcaggatggc caggaagacg 20

<210> SEQ ID NO 302
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 302
ggaagtccat cacctgagcg 20

<210> SEQ ID NO 303
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 303
catgcctctg ggcagctagc 20

<210> SEQ ID NO 304
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 304
cccgcatctc ttgaacacga 20

<210> SEQ ID NO 305
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 305
tgtggctggc aggccagcag 20

<210> SEQ ID NO 306
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 306
ctgtggctgg caggccagca 20

<210> SEQ ID NO 307
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 307
caggatccac cagaagccca 20

<210> SEQ ID NO 308

-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 308
aagatgaaga agttgatcag 20

<210> SEQ ID NO 309
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 309
ttgtagtctg tgtggtgcat 20

<210> SEQ ID NO 310
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 310
gtggctggca ggccagcagc 20

<210> SEQ ID NO 311
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 311
gcaggctcag gttgtggtga 20

<210> SEQ ID NO 312
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 312
ctggctgtag cgggtcctga 20

<210> SEQ ID NO 313
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 313
tctgggcagc tagctgcctc 20

<210> SEQ ID NO 314
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 314

-continued ggccagcagg aatacttgtc 20

<210> SEQ ID NO 315
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 315
ctcaaacagg aagtccatca 20

<210> SEQ ID NO 316
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 316
ggtagaggct gaagaagctc 20

<210> SEQ ID NO 317
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 317
gaggaagagg tcgaagaaga 20

<210> SEQ ID NO 318
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 318
gaggtcgaag aagagcttgg 20

<210> SEQ ID NO 319
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 319
tgtagtctgt gtggtgcatc 20

<210> SEQ ID NO 320
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 320
agaagttgat caggatggcc 20

<210> SEQ ID NO 321
<211> LENGTH: 20
<212> TYPE: DNA

-continued

<213> ORGANISM: Artificial Sequence
<220> FEATURE:
<223> OTHER INFORMATION: Antisense Oligonucleotide

<400> SEQUENCE: 321
aagcggtgtt gcactttgtg 20

<210> SEQ ID NO 322
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 322
ggaatacttg tcgaaggttc 20

<210> SEQ ID NO 323
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 323
gaagaggtcg aagaagagct 20

<210> SEQ ID NO 324
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 324
agcaggaata cttgtcgaag 20

<210> SEQ ID NO 325
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 325
aggctcaggt tgtggtgaca 20

<210> SEQ ID NO 326
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 326
ggtgttgcac tttgtggtgc 20

<210> SEQ ID NO 327
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 327
ggaacttgta gtctgtgtgg 20

-continued

<210> SEQ ID NO 328
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 328
gtgacactgg tcaccgtaga 20

<210> SEQ ID NO 329
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 329
ttgcatgaac accgcggcca 20

<210> SEQ ID NO 330
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 330
ctggaagctg ctgtacatct 20

<210> SEQ ID NO 331
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 331
tccaccagaa gcccatgttg 20

<210> SEQ ID NO 332
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 332
aagttgatca ggatggccag 20

<210> SEQ ID NO 333
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 333
caggcccagc aggttgtgca 20

<210> SEQ ID NO 334
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 334
accgctccat cactgagcca 20

<210> SEQ ID NO 335
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 335
atgaagaagt tgatcaggat 20

<210> SEQ ID NO 336
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 336
ctcttgaaca cgaagcggtg 20

<210> SEQ ID NO 337
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 337
ctggcaggcc agcagcagca 20

<210> SEQ ID NO 338
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 338
aggagatgtt ggccgtggta 20

<210> SEQ ID NO 339
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 339
gcccatgttg tcattgctgg 20

<210> SEQ ID NO 340
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 340
aagaagttga tcaggatggc 20

-continued

<210> SEQ ID NO 341
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 341
cccaggtaga ggctgaagaa 20

<210> SEQ ID NO 342
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 342
cccatgttgt cattgctggt 20

<210> SEQ ID NO 343
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 343
acacgaagcg gtgttgcact 20

<210> SEQ ID NO 344
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 344
cagcaggctc aggttgtggt 20

<210> SEQ ID NO 345
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 345
tgtggtgaca ctggtcaccg 20

<210> SEQ ID NO 346
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 346
gcccagcagg ttgtgcaggt 20

<210> SEQ ID NO 347
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 347
tggctgtagc gggtcctgag 20

<210> SEQ ID NO 348
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 348
gcccgcatct cttgaacacg 20

<210> SEQ ID NO 349
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 349
aagaggtcga agaagagctt 20

<210> SEQ ID NO 350
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 350
gggcagcagg ctcaggttgt 20

<210> SEQ ID NO 351
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 351
catctcttga acacgaagcg 20

<210> SEQ ID NO 352
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 352
atccaccaga agcccatgtt 20

<210> SEQ ID NO 353
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 353
gtcattgctg gtccagcact 20

<210> SEQ ID NO 354
<211> LENGTH: 20

-continued

<212> TYPE: DNA
<213> ORGANISM: Artificial Sequence
<220> FEATURE:
<223> OTHER INFORMATION: Antisense Oligonucleotide

<400> SEQUENCE: 354
tcgggcccgc atctcttgaa 20

<210> SEQ ID NO 355
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 355
cccccaggga caggctgtag 20

<210> SEQ ID NO 356
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 356
ccatgttgtc attgctggtc 20

<210> SEQ ID NO 357
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 357
gaggctgaag aagctcctct 20

<210> SEQ ID NO 358
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 358
gaacacgaag cggtgttgca 20

<210> SEQ ID NO 359
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 359
ttctcaaaca ggaagtccat 20

<210> SEQ ID NO 360
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 360

-continued tgttgtcatt gctggtccag 20

<210> SEQ ID NO 361
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 361
aggaatactt gtcgaaggtt 20

<210> SEQ ID NO 362
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 362
caggctcagg ttgtggtgac 20

<210> SEQ ID NO 363
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 363
aggaagaggt cgaagaagag 20

<210> SEQ ID NO 364
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 364
gctgaggaag aggtcgaaga 20

<210> SEQ ID NO 365
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 365
cacgaagcgg tgttgcactt 20

<210> SEQ ID NO 366
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 366
aagcccatgt tgtcattgct 20

<210> SEQ ID NO 367
<211> LENGTH: 20
<212> TYPE: DNA
<213> ORGANISM: Artificial Sequence -continued
<220> FEATURE:
<223> OTHER INFORMATION: Antisense Oligonucleotide

<400> SEQUENCE: 367
atgcctctgg gcagctagct 20

<210> SEQ ID NO 368
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 368
catcacctgg aagctgctgt 20

<210> SEQ ID NO 369
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 369
acttctcaaa caggaagtcc 20

<210> SEQ ID NO 370
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 370
gcatctcttg aacacgaagc 20

<210> SEQ ID NO 371
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 371
catattgcat gaacaccgcg 20

<210> SEQ ID NO 372
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 372
ccagaagccc atgttgtcat 20

<210> SEQ ID NO 373
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 373
gctgtagcgg gtcctgagca 20

-continued

<210> SEQ ID NO 374
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 374
tgtagcgggt cctgagcagc 20

<210> SEQ ID NO 375
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 375
aggcccagca ggttgtgcag 20

<210> SEQ ID NO 376
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 376
tacatcacct ggaagctgct 20

<210> SEQ ID NO 377
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 377
cgcaggatcc accagaagcc 20

<210> SEQ ID NO 378
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 378
aaacaggaag tccatcacct 20

<210> SEQ ID NO 379
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 379
agaggctgaa gaagctcctc 20

<210> SEQ ID NO 380
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 380
ttgatcagga tggccaggaa 20

<210> SEQ ID NO 381
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 381
agcggtgttg cactttgtgg 20

<210> SEQ ID NO 382
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 382
gctggcaggc cagcagcagc 20

<210> SEQ ID NO 383
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 383
acgaagcggt gttgcacttt 20

<210> SEQ ID NO 384
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 384
gcatgaacac cgcggccaca 20

<210> SEQ ID NO 385
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 385
caggaagtcc atcacctgag 20

<210> SEQ ID NO 386
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 386
gcaggatcca ccagaagccc 20

<210> SEQ ID NO 387

-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 387
agttgatcag gatggccagg 20

<210> SEQ ID NO 388
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 388
gcccccaggg acaggctgta 20

<210> SEQ ID NO 389
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 389
aacaggaagt ccatcacctg 20

<210> SEQ ID NO 390
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 390
atattgcatg aacaccgcgg 20

<210> SEQ ID NO 391
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 391
gcaggaatac ttgtcgaagg 20

<210> SEQ ID NO 392
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 392
gtacatcacc tggaagctgc 20

<210> SEQ ID NO 393
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 393

-continued cattgctggt ccagcactgg 20

<210> SEQ ID NO 394
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 394
caaacaggaa gtccatcacc 20

<210> SEQ ID NO 395
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 395
agggtggcca ggcccagcag 20

<210> SEQ ID NO 396
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 396
ttgaacacga agcggtgttg 20

<210> SEQ ID NO 397
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 397
accagaagcc catgttgtca 20

<210> SEQ ID NO 398
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 398
ctcaggttgt ggtgacactg 20

<210> SEQ ID NO 399
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 399
gttgtggtga cactggtcac 20

<210> SEQ ID NO 400
<211> LENGTH: 1633
<212> TYPE: DNA

-continued

<213> ORGANISM: M. musculus
<220> FEATURE:

<400> SEQUENCE: 400
gctcggctgt catgaggcct tgggcttgga ggcttggctt gggggaacag gatgctgtgt 60
agattttctc cagactccac tattctggtc ctctgcagcc tgaggagagg tgcacacact 120
ctgaggacct aggtgtgcaa cctctgccag atgtggggcg tggctaccca gaggcatgcc 180
cctcacccag ctccactgtc cccacctgct gctgctgctg ttggtgctgt catgtctgcc 240
agaggcaccc tctgcccagg taatggactt tttgtttgag aagtggaagc tctatagtga 300
ccaatgtcac cacaacctaa gcctgctgcc cccacctact gagctggtct gtaacagaac 360
cttcgacaac tactcctgct ggcctgacac ccctcccaac accactgcca acatttcctg 420
cccctggtac ctaccttggt gccacaaagt gcagcaccgc ctagtgttca agaggtgtgg 480
gcccgatggg cagtgggttc gagggccacg gggcagccg tggcgcaacg cctcccaatg 540
tcagttggat gatgaagaga tcgaggtcca gaagggggtg gccaagatgt atagcagcca 600
gcaggtgatg tacaccgtgg gctacagtct gtccctgggg gccttgctcc ttgcgctggt 660
catcctgctg ggcctcagga agctgcactg cacccgaaac tacatccatg ggaacctgtt 720
tgcgtccttt gtgctcaagg ctggctctgt gttggtcatc gattggctgc tgaagacacg 780
gtacagccag aagattggcg atgacctcag tgtgagcgtc tggctcagtg acggggcgat 840
ggccggctgc agagtggcca cagtgatcat gcagtacggc atcataccca actattgctg 900
gttgctggta gagggcgtgt acctgtacag cctgctgagc cttgccacct tctctgagag 960
gagcttcttt tccctctacc tgggcattgg ctggggtgcg cccctgctgt ttgtcatccc 1020
ctgggtggtg gtcaagtgtc tgtttgagaa tgttcagtgc tggaccagca atgacaacat 1080
gggattctgg tggatcctgc gtattcctgt cttcctggcc ttactgatca attttttcat 1140
ctttgtccac atcattcaac ttcttgtggc caagctgcgt gcccatcaga tgcactatgc 1200
tgattacaag ttccggctgg ccaggtccac gctgaccctc atccctctgc tgggggtcca 1260
cgaggtggtc tttgcctttg tgactgacga gcatgcccaa ggcaccctgc gctccaccaa 1320
gctctttttt gacctgttcc tcagctcctt ccagggtctg ctggtggctg ttctctactg 1380
tttcctcaac aaggaggtgc aggcagagct gatgcggcgt tggaggcaat ggcaagaagg 1440
caaagctctt caggaggaaa ggttggccag cagccatggc agccacatgg ccccagcagg 1500
gccttgtcat ggtgatccct gtgagaaact tcagcttatg agtgcaggca gcagcagtgg 1560
gactggctgt gtgccctcta tggagacctc gctggccagt agtctcccaa ggttggctga 1620
cagccccacc tga 1633

<210> SEQ ID NO 401
<211> LENGTH: 10362
<212> TYPE: DNA
<213> ORGANISM: M. musculus
<220> FEATURE:

<400> SEQUENCE: 401
agcttccttg ttctgccgcc ctctccccag tctgtccaca agaaaacaag gtcgggggta 60
aggtccttat gaaaggaaag acctccatct tccagggaat gcaccttgag gtgcaggaag 120
cccagctgag ccacagaacc tagacagagg caactgcaga ccagtgcctg ctcccactct 180
gccctggcca ccataggctg agcacctcca gcccagggcc acactggtgc agttcctggc 240
acccctcatc cctaagtctc attaccaggt cacagagggg cagacctttg ctgtggagca 300

-continued

```
caatcctcca gcctgtgccc cagggagatg aaggaggagc tgtatctatc cctcagcctt    360
gcacaagcgg cccccactgg gcggcggaaa caaacaggtc tttgccttct aacctttgcc    420
ttctggccat tgcctggatc aaaacagaaa agggcagctc cctgtcagga tttctggtgg    480
actcttctga agataggggc acagaagaca gagccccggg gagtatccct gtccccaaat    540
cctggcaggg tcttcctgtg gatcttatag acatgtacaa agcagggtct gcctacgaat    600
cactggaggg tgggccagct caccggtgag ggaacccaca ggttggggca caagatccaa    660
tgtcccctaa atagacatgg agtcctggag aaggacaaca actgaacaag gaactgaccc    720
aaggcccatg ggagttctga ggaagggcgg tgggtgacag agaagaaacc acatgtgttc    780
cagatgagag agactggtgc tggactggat tccctagagg ggcctcggct ctttactaga    840
tgatctgcag gtatgaggtg gaggagagga cacagacata ggagacttgg gccgcagagg    900
actggtctgg gggctggaaa tggggaggga ggttgtgagt acccattctg aaagccacag    960
ttacagggag aactttctag aaagcaacat gaccctctta caggatgtgg agaagccaga   1020
gaagtggaag cccaaaaaca cccaagggag tttctgatcc cgaggttact gggcaggagg   1080
ggagatgagg caacaaaagg tggctcaagg gctcaaatgg gggggcgggc agtggagaaa   1140
gtcctctcca gggctgagtc taggagcgaa aggcaggctt gtggctcaga acctttgact   1200
ccagaaaagg aggtatctaa aaaaggtctg tgccgactga gaatatggcc aaattagtgg   1260
attgtcaaat gagtggtgtt gcttgagggc ttattggaca ggagtccctg aggcccacag   1320
ggcatgtaac ctggaaaggg tttaagaggc actcttagcg gatcaccttg tctgaaatct   1380
gcagagcggc ccatgtatcc tgacctctcc cacccatggt gcatgtgtgg cagctgcaac   1440
cttccagcca ggagccagat gtggttaagt aagggactta gtccttctag aaaatcaaga   1500
ctgcaaacct gaacgcaatg atgagacccc aggacagtgg acattgaaag agaaaggggc   1560
gcgctgagtc acttattgtt cccttggaga actcagaccc atcaggattc gcacctgcca   1620
ggtcaggatt cacccgtgga ggctctctga agtccagggt gcgcaaggtt ggatcctcag   1680
ggttacggta cacctggtga gggttctcgg aagggacccg tagggtcgga tccaggtcag   1740
ggcctgctcc tgtgtgccag aggggaggga aagggagaac gcgggatgca gacctgccag   1800
gcaagctcag cccaggagat atactcgggg ttacaccgag agggtctgag agctcgctgc   1860
aggtccgctg cactaaggcg cgggcgcgga ccctcatctc tccccctccc ccgcgggccg   1920
ctcccgcccc cacccctccc ccttcgccgc cgcccagcgt cgccgctgga aagtttgcga   1980
gcggctggcg cggagctggc gccgaccccg atcacagcgc ggccgaggcg agcagtcgcc   2040
ggcgcccaga tccgagtacg ctcgaggacc gcgaggagcg cagccctagc cccggcgact   2100
gagcacagtg agcactaggg tcgggccccg agggatggtc tcaggctgtc tgtggggtgc   2160
tggagcacga gcgtgacctg ggcgcacaga agaggggagc ggggagctgg ccctcgggcc   2220
tggacgtaag ccagctgtcc ctggggtttt gggagtcgcg gttctcgtcc cggtctaaca   2280
ccttattcaa aacgggaaat gtgtcctact gtcacggtta gggccacctg attcccaacc   2340
gtctcctgca ggttaggggt ctcaacttct cctttctatt ttctgggagc gcaatccagg   2400
aaggtgggag agggtgggtg cagacgtgga tcctgctgcc ccattgaacg cccaacacac   2460
tccagcttcc agcttctcac actccaaagg ctcgctcatc cccttcagat ggattcgctt   2520
ccccttccta tgtgtccctg atctccagaa cttcctagca gtgtctcagt cttgcgggtt   2580
agatgtgtag gcaccgtgca ctgagggttt tttttcccct gcaagctcag gtcattgctc   2640
```

-continued

```
cccagagacc accttcccac ttcagacccg cgaagttttc tgtcgcaaac cgactgatcc   2700
cttacctctt agctctcgca tccttcgagg ttagaccagg catattttgc tgttcttctg   2760
tcttggagac atagaagggg gaatctgagc tcacccgagc ccgtgggtat ctccgcccct   2820
tttcagggga ggactggaga actaggcttt gtcacagcct gtggcccctg atcctgtccc   2880
tgccatagga ctatgacctg gtctagtttc tctgttttga caaaaacacc cttccagttg   2940
atatctctgg ggattcctaa gatcaaaaac gttgctactt tggcttctaa ggaaccaaga   3000
ggatcccccc cccaccttcc ctcgatgcct ccctttggcc actgggccat ccatctaaca   3060
ccctccgcca cctgcagaga aaatcggtaa ccacactgca aacacccacg tgtcctttgt   3120
cctgttggag cttgctggaa gcggtggtgg catgggacaa tgccagtccg agtggctggt   3180
gtggtggtgg catgggacaa tgccagtccg agtggctggt gtgccagata tgtgctctga   3240
agaaggggga ttgattgatc taaaggcaag acaggcaagc atcttaggga ttcagacttg   3300
catcttccgt atttcaccta cagttgggtc tcactgagag tcagatttca gcagcctagt   3360
tcaagacggg aagagggtag ggtccctggt ctactgtccc ttatgtccat ctgttccctg   3420
acagggaggg taataaggtg gaaaaaggac cagaactgca gctcaggtca caggtgcgag   3480
agcgcgtcgt gcacacctgg ctgcctgtca ccctgagtat ttatcagagc tgataggctc   3540
tgtctgagtg tcagtatttg cccaccgtgg ggacaggagg cacactgcga aggtacagag   3600
attgcagtcc tatcctactg acgacatagc ctctctcctt cagtggaagg gaaagggtgc   3660
cgtgttgctc ttcatacatc tctgctctct taaagtccag acgttttctg cagagacccc   3720
agagtctcaa tttcatgggg ctgaagtcag cctcagcttc ctgatgccag aaatccccca   3780
tcgttattcc atccacagga atagaacact caccccacct tttctgccac ttttgtttga   3840
gagacaaggt tagaggttac tgaaccctta gggatccagc cctgagtggt tttgagctca   3900
cccactgtgg tctcagtgct aaactgtgtg tggaaggaaa tcctcaaggg ttcttggtct   3960
cgcctttgtt actctttgtt atttatttat ttttggattt ttcttttttc ttttgtttgt   4020
ttgttttgtt ttgttttgtg acagggtttc tctgtgtagc cctgggtatc cctgacctta   4080
ctatgtagac caggctagcc tcaaactcag agatcctcct gtctctgtct cccgagtctg   4140
ggattaaagg tgtgtgccac cacctatcgg tcattgaaca tttacatttt caggttgggc   4200
aactgggctc taaggaccat cctccccgac tgtcttgatc ttcatccttg caggatcttg   4260
gaccacatcc ttccccacca tgtcccttcc ctgtatctcc actccccatc tacccacgct   4320
ggtcatcttt tatcaccttc acactgccct gaagccttcc cgcctctaac cttcctcttt   4380
caggcctcta tgagacccca gtagctctgg tggaggccag gcatagtgtg taaagagcca   4440
gcttctggct tttggcttct ccatacccag cccactaata atctgggaca tttaatgcaa   4500
attaggaaag tcatgccact tggtgacccc agaggtaggg atacttgaac cacctacacc   4560
tcctcaacct gtctgctgcc ttgtccccag caggaaccct ctactctgag ggtgtttttc   4620
cctgaggttc agagacctga aatcctggat cttgcctctg gccagaccct gttgaccaag   4680
ggcttggctc aggagtccct cagtaggttg tgaaccagat gtgactgaag ggagcataaa   4740
tgtaggaggt caggagggga gccctaccaa gctgctattc ctagaactca gctggtctta   4800
ttacagcagg ctgaaagcca gggctccact tttccccaat tgggttcttc tctctcatcc   4860
ccaccctctc tcccctcacc ccagggggtc tttgtatgta gtcctggctg gcactgaact   4920
ttgggtagta cacttgcttc tacctcctga atggtaggac tacaggtatg tgccaccata   4980
cctggctcta tcttgtatat tctgtttgtg ggtacacagg acataggccc aactcagccc   5040
```

-continued taggagctca tagtttgact tcttagagcc cccaagaagc tctttgcttt tctggcatga 5100
gaatccatca gagctgtctt agttagggtt ttactgctgt gaacagacac catggccaag 5160
gcagctctta taaggatgac atttaattgg ggctggctta caggttcaga ggttcagtcc 5220
attatcatca aggcaagaac atggcagcat ccaggcaggc atggtgcagg aggagctgag 5280
agttccattt cttgttctga atgcagctag cggaagaatg gcttccaagc tgctaggaca 5340
agagtattaa agcccacatg cacaatgaca cgcctattcc aacaaggcca tacctcctaa 5400
tggtgacact tcctcggcca agaacatata aaccatcata agagccaaaa aagggtgctg 5460
gtgcagagag gggctggtga ctaggatctg tcacccgtga tgatcccatg tcttaacgaa 5520
aacatcaggc agaggtgtcc ctcatctggg ccctggctcg gaactgacct ggaatgaggg 5580
ccaagtggcg atgcgcctgg gtaccacacc cttactctct ctatcccagg gcaggttgcc 5640
tagctagtta gctttcctac ggggctaaga ataggtggag atgtctaggc taggacatca 5700
tagctgagtt gttggtgcca ctctgagaga tttgtgtgac cagataggga ggtgattgct 5760
ttcagctgga caaccccatg tagcgggaaa acagtagccc atagtcacct gtctctgaat 5820
aggcactgtg agccactcac gtgtctcctc ccgaagctcg gctgtcatga ggccttgggc 5880
ttggaggctt ggcttggggg aacaggatgc tgtgtagatt ttctccagac tccactattc 5940
tggtcctctg cagcctgagg agaggtgcac acactctgag gacctaggtg tgcaacctct 6000
gccagatgtg gggcgtggct acccagaggc atgcccctca cccagctcca ctgtccccac 6060
ctgctgctgc tgctgttggt gctgtcatgt ctggtgagta ccgtgcacgc cactgccctg 6120
catggagagt ttgcctgctc tttacacaag tgctgacagc tccctggtcc ttgtcgacac 6180
cctgtttccc agccagaggc accctctgcc caggtaatgg actttttgtt tgagaagtgg 6240
aagctctata gtgaccaatg tcaccacaac ctaagcctgc tgccccccacc tactggtgag 6300
tcccacccac ctacacacac agactcctgt gtcctgtagc cctgtctgga tgtgcagtag 6360
gagaccctgt gggagtgtac tgtaaggatg gtttataatg cccagccact gccccagttc 6420
cagggcaggc gactgacctc cagaggtggt ggttccctaa agctacattg tcaggaagca 6480
gtagaaatgc agagctgcct cctagttgtc cctgctgtcc tccctgctgg aggctgtcct 6540
ccctgctgga ggctgtcctc cctgctatgg gacaccctca tccccagcca tctgatgtct 6600
cctctgctgt catcactcac actgggcaga cagtgagcag ggacaggatg ggtgccaaga 6660
gagattgggt ccttattatc gctcagttga gggagatgac aagtgcctgg gagggagaga 6720
gggagaaggt tgcaggagct atggctgggc ctggaaagga tttcaaccaa gctggagagc 6780
aacatctgca aagagatgca tccccaggct ggggccgcca gttagatcca gtgagatggc 6840
tcggcagata caggccctgg cctccgggac tcacacaggg taaaacacag aaatgattcc 6900
tgcaaggtgc cctatgatcc tatatgctag tgtacataca tgtatgagtc agagtgcatg 6960
cacatgtgcg cacacacaca catacactaa caaacgaaca aacaataact aaatgtaaaa 7020
aattgttaca atttaaaaat taaaataaaa agacagagag gaaagaccca aaatgggttt 7080
ggtgacattt gagataggat gtggtcttga aggagaggtg ccttggccaa acacaaatgt 7140
tgctgggctg gagagggagg tagtcatggc atctagatgg caagatcact ggccagggga 7200
tgccccttgt ggcccatatc agggaggcag cccctttaga tgcaggctcc gtgtagtggt 7260
ggtgatgctc aggggacttc cggtctcagg ggacttctgg tccctcctcc atcctcctgc 7320
accttcacag agctggtctg taacagaacc ttcgacaact actcctgctg gcctgacacc 7380

-continued

```
cctcccaaca ccactgccaa catttcctgc ccctggtacc taccttggtg ccacaaaggt   7440
aacagtggaa ggcctgggag gctgaggggg tggagcctag gagtggcctg accagagctt   7500
gcacccatgc ccagtgcagc accgcctagt gttcaagagg tgtgggcccg atgggcagtg   7560
ggttcgaggg ccacgggggc agccgtggcg caacgcctcc caatgtcagt tggatgatga   7620
agagatcgag gtccaggtca gctctggagg gtatggggtg gtgtcacagc ggggctgtgt   7680
gggggcaggg gatacggcac tgcccagccc cactcggtct ctggtttgca gaagggggtg   7740
gccaagatgt atagcagcca gcaggtgatg tacaccgtgg gctacagtct gtccctgggg   7800
gccttgctcc ttgcgctggt catcctgctg ggcctcaggt acattggtgt tggctcctag   7860
ctaataccca gtgtggtgag gggggtagag gacagggcag gagtggtgct gatacgctgt   7920
cacataggaa gctgcactgc acccgaaact acatccatgg gaacctgttt gcgtcctttg   7980
tgctcaaggc tggctctgtg ttggtcatcg attggctgct gaagacacgg tacagccaga   8040
agattggcga tgacctcagt gtgagcgtct ggctcagtga cggggtgagc ccagatctga   8100
ctgctcccca gcccgttagg gtgtcggggt gtcgtggact ccactcatgc ctcaccttgc   8160
tcaggcgatg gccggctgca gagtggccac agtgatcatg cagtacggca tcatacccaa   8220
ctattgctgg ttgctggtag agggcgtgta cctgtacagc ctgctgagcc ttgccacctt   8280
ctctgagagg agcttctttt ccctctacct gggcattggc tggggtgcgt aggctcttgg   8340
gggcagtggg ggaaggaggc tagccagggc tgtagaacca cagctgctgc ttcccacagg   8400
tgcgcccctg ctgtttgtca tcccctgggt ggtggtcaag tgtctgtttg agaatgttca   8460
gtgagtatga gctggtacag tgggctggag cagttggtgc tgcctttgta aagtgaccct   8520
gggggctggg gaggggcagg ggctggagag tggcatcccc cccagtaagg gagcaactgt   8580
taccctgcag gtgctggacc agcaatgaca acatgggatt ctggtggatc ctgcgtattc   8640
ctgtcttcct ggccttactg gtgaggaaac aggcccccgt tgccatcagc agggaaaggg   8700
ccaccactgg cctggctctc ctaggccctt ccttcctcag gaggatgtac atgctgggtc   8760
tgtgggtcag gttgcccatc cttggctgaa tgcctgccag tccctgggcc atgtatccag   8820
gactcacctg gcagcagcct cacctgtatc aggggcatag aagggccatg gtaggacata   8880
ggaagttctc aggctctgcc ctcgacgttt ggctttctca cacagatcaa tttttttcatc   8940
tttgtccaca tcattcaact tcttgtggcc aagctgcgtg cccatcagat gcactatgct   9000
gattacaagt tccggttggt aagggggagg ggcctggccc agattggaga ggggagggtt   9060
gggtcaaagc cttgggggga aacccaaaga agacccggaa ggtaagggtc ctcaactctt   9120
tcccccctaca ggctggccag gtccacgctg accctcatcc ctctgctggg ggtccacgag   9180
gtggtctttg cctttgtgac tgacgagcat gcccaaggca ccctgcgctc caccaagctc   9240
ttttttgacc tgttcctcag ctccttccag gtgagtctcc atcatacccc acccctggga   9300
cccagagtgc tgtccttgac cactctcttt ctccagggtc tgctggtggc tgttctctac   9360
tgtttcctca acaaggaggt aggtgaagct gggaacacaa tcagagcact ggccctgagg   9420
gtggccttgc cctggtatga ccatatctcc aatccccatt attaaggttg catgtgttgg   9480
aatgtcaggt ccccctaggt cctcagggaa ttcagtgtat gaggtggtcc ttgcctttcc   9540
tggtgacaaa tggccccgct gaacccaagg tgaaacttgc cttgctctgg gtctgcttag   9600
attaaggctg ggcacctcag agaggcccag acaagatcct aatgaggtgc gttggcagag   9660
tagccctacc cctggctcct ctaggtgcag gcagagctga tgcggcgttg gaggcaatgg   9720
caagaaggca aagctcttca ggaggaaagg ttggccagca gccatggcag ccacatggcc   9780
```

ccagcagggc cttgtcatgg tgatccctgt gagaaacttc agcttatgag tgcaggcagc 9840
agcagtggga ctggctgtgt gccctctatg gagacctcgc tggccagtag tctcccaagg 9900
ttggctgaca gccccacctg aatctccact tggagcctag gcaggttgtg ttcaagaaag 9960
ggcctcagag gacaacccag agccagatgc ccggccaagg ttgaagagcc aaagcagcaa 10020
gacagcagct tgtactgtgc acactcccct aacctgtcct agcctggcac aggccacagt 10080
gacagagtag gggttggata tgatggagaa gccatgttat ctatgaactc tgagtgttcc 10140
catgtgtgtt gacatggtcc ctgtacccag atatgtcctt cagtaaaaag ctcgagtgga 10200
gctgctgcac agctcgtgga cagcaggctt gaagccccca gggacggggt ttgggaggcc 10260
ggggatgagc agcacactca gcaggtggag cgctagtgca acccaggaaa gaactgtctc 10320
taacgtggtg ctctggggta ggagcccact tcctccagga tc 10362

<210> SEQ ID NO 402
<211> LENGTH: 1670
<212> TYPE: DNA
<213> ORGANISM: M. musculus
<220> FEATURE:

<400> SEQUENCE: 402
gtttgcgagc ggctggcgcg gagctggcgc cgaccccgat cacagcgcgg ccgaggcgag 60
cagtcgccgg cgcccagatc cgagtacgct cgaggaccgc gaggagcgca gccctagccc 120
cggcgactga gcacacctga ggagaggtgc acacactctg aggacctagg tgtgcaacct 180
ctgccagatg tggggcgtgg ctacccagag gcatgcccct cacccagctc cactgtcccc 240
acctgctgct gctgctgttg gtgctgtcat gtctgccaga ggcaccctct gcccaggtaa 300
tggacttttt gtttgagaag tggaagctct atagtgacca atgtcaccac aacctaagcc 360
tgctgccccc acctactgag ctggtctgta acagaacctt cgacaactac tcctgctggc 420
ctgacacccc tcccaacacc actgccaaca tttcctgccc ctggtaccta ccttggtgcc 480
acaaagtgca gcaccgccta gtgttcaaga ggtgtgggcc cgatgggcag tgggttcgag 540
ggccacgggg gcagccgtgg cgcaacgcct cccaatgtca gttggatgat gaagagatcg 600
aggtccagaa gggggtggcc aagatgtata gcagccagca ggtgatgtac accgtgggct 660
acagtctgtc cctgggggcc ttgctccttg cgctggtcat cctgctgggc ctcaggaagc 720
tgcactgcac ccgaaactac atccatggga acctgtttgc gtcctttgtg ctcaaggctg 780
gctctgtgtt ggtcatcgat tggctgctga agacacggta cagccagaag attggcgatg 840
acctcagtgt gagcgtctgg ctcagtgacg gggcgatggc cggctgcaga gtggccacag 900
tgatcatgca gtacggcatc atacccaact attgctggtt gctggtagag ggcgtgtacc 960
tgtacagcct gctgagcctt gccaccttct ctgagaggag cttcttttcc ctctacctgg 1020
gcattggctg gggtgcgccc ctgctgtttg tcatcccctg ggtggtggtc aagtgtctgt 1080
ttgagaatgt tcagtgctgg accagcaatg acaacatggg attctggtgg atcctgcgta 1140
ttcctgtctt cctggcctta ctgatcaatt ttttcatctt tgtccacatc attcaacttc 1200
ttgtggccaa gctgcgtgcc catcagatgc actatgctga ttacaagttc cggctggcca 1260
ggtccacgct gaccctcatc cctctgctgg gggtccacga ggtggtcttt gcctttgtga 1320
ctgacgagca tgcccaaggc accctgcgct ccaccaagct cttttttgac ctgttcctca 1380
gctccttcca gggtctgctg gtggctgttc tctactgttt cctcaacaag gaggtgcagg 1440
cagagctgat gcggcgttgg aggcaatggc aagaaggcaa agctcttcag gaggaaaggt 1500

-continued

```
tggccagcag ccatggcagc cacatggccc cagcagggcc ttgtcatggt gatccctgtg   1560

agaaacttca gcttatgagt gcaggcagca gcagtgggac tggctgtgtg ccctctatgg   1620

agacctcgct ggccagtagt ctcccaaggt tggctgacag ccccacctga              1670


<210> SEQ ID NO 403
<211> LENGTH: 540
<212> TYPE: DNA
<213> ORGANISM: M. musculus
<220> FEATURE:

<400> SEQUENCE: 403

acccgaagaa gctacagaga cagagatgtg agcattaacg agtggaggga agagacctag     60

agataaagca cgcgccggag ctctgtatac cagcacctga ggagaggtca cacactctga    120

ggacctaggt gtgcaacctc tgccagatgt ggggcgtggc tacccagagg catgccctca    180

cccagctcca ctgtccccac ctgctgctgc tgctgttggt gctgtcatgt ctgccagaca    240

gccctctgcc caggtaatgg actttttgtt tgagaagtgg aagctctata gtgaccaatg    300

ccaccacaac ctaagcctgc tgcccccacc tactgagctg ggtctgtaca gaaacttcga    360

caagtactcc tgctggcctg gaaaccctcc caacaccact gcgaacattt cctgcgccct    420

ggtacctaca cttgtagcac aaagtgcaac acggcctagg tgttcaagag gttgtgggcc    480

cgatgagggt aggggttcga ggggcaaggg gggcagccgg gcgaaacgcg tcccaaatgt    540


<210> SEQ ID NO 404
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 404

cccacatctg gcagaggttg                                                 20


<210> SEQ ID NO 405
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 405

ttctcaaaca aaaagtccat                                                 20


<210> SEQ ID NO 406
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 406

agagcttcca cttctcaaac                                                 20


<210> SEQ ID NO 407
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 407
```

```
tggtcactat agagcttcca                                               20

<210> SEQ ID NO 408
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 408

agcaggctta ggttgtggtg                                               20

<210> SEQ ID NO 409
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 409

ggcaggaaat gttggcagtg                                               20

<210> SEQ ID NO 410
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 410

ggcccacacc tcttgaacac                                               20

<210> SEQ ID NO 411
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 411

ccccttctgg acctcgatct                                               20

<210> SEQ ID NO 412
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 412

ccagggacag actgtagccc                                               20

<210> SEQ ID NO 413
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 413

agtgcagctt cctgaggccc                                               20

<210> SEQ ID NO 414
<211> LENGTH: 20
<212> TYPE: DNA
```

-continued

<213> ORGANISM: Artificial Sequence
<220> FEATURE:
<223> OTHER INFORMATION: Antisense Oligonucleotide

<400> SEQUENCE: 414
cacttgacca ccacccaggg 20

<210> SEQ ID NO 415
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 415
tcaaacagac acttgaccac 20

<210> SEQ ID NO 416
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 416
ttgtcattgc tggtccagca 20

<210> SEQ ID NO 417
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 417
aggatccacc agaatcccat 20

<210> SEQ ID NO 418
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 418
agggtcagcg tggacctggc 20

<210> SEQ ID NO 419
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 419
aagagcttgg tggagcgcag 20

<210> SEQ ID NO 420
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 420
tagagaacag ccaccagcag 20

-continued

<210> SEQ ID NO 421
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 421
ggaaacagta gagaacagcc 20

<210> SEQ ID NO 422
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 422
cacctccttg ttgaggaaac 20

<210> SEQ ID NO 423
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 423
ctcctcaggt tgcaagggag 20

<210> SEQ ID NO 424
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 424
tgcacctctc ctcaggttgc 20

<210> SEQ ID NO 425
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 425
ctcagagtgt gtgcacctct 20

<210> SEQ ID NO 426
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 426
aggtcctcag agtgtgtgca 20

<210> SEQ ID NO 427
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 427
ggcagaggtt gcacacctag 20

<210> SEQ ID NO 428
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 428
ggcatgcctc tgggtagcca 20

<210> SEQ ID NO 429
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 429
tggcagacat gacagcacca 20

<210> SEQ ID NO 430
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 430
gagcttccac ttctcaaaca 20

<210> SEQ ID NO 431
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 431
cagaccagct cagtaggtgg 20

<210> SEQ ID NO 432
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 432
ggtgtcaggc cagcaggagt 20

<210> SEQ ID NO 433
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 433
cggtgctgca ctttgtggca 20

-continued

<210> SEQ ID NO 434
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 434
ttgaacacta ggcggtgctg 20

<210> SEQ ID NO 435
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 435
cgtggccctc gaacccactg 20

<210> SEQ ID NO 436
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 436
aaggccccca gggacagact 20

<210> SEQ ID NO 437
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 437
cccagcagga tgaccagcgc 20

<210> SEQ ID NO 438
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 438
cttcctgagg cccagcagga 20

<210> SEQ ID NO 439
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 439
acagagccag ccttgagcac 20

<210> SEQ ID NO 440
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 440
actgtggcca ctctgcagcc 20

<210> SEQ ID NO 441
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 441
actgcatgat cactgtggcc 20

<210> SEQ ID NO 442
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 442
atgatgccgt actgcatgat 20

<210> SEQ ID NO 443
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 443
agcaggctgt acaggtacac 20

<210> SEQ ID NO 444
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 444
tcattgctgg tccagcactg 20

<210> SEQ ID NO 445
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 445
gacaggaata cgcaggatcc 20

<210> SEQ ID NO 446
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 446
cgcagcttgg ccacaagaag 20

<210> SEQ ID NO 447
<211> LENGTH: 20

-continued

<212> TYPE: DNA
<213> ORGANISM: Artificial Sequence
<220> FEATURE:
<223> OTHER INFORMATION: Antisense Oligonucleotide

<400> SEQUENCE: 447
tctgatgggc acgcagcttg 20

<210> SEQ ID NO 448
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 448
gcatagtgca tctgatgggc 20

<210> SEQ ID NO 449
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 449
cttgtaatca gcatagtgca 20

<210> SEQ ID NO 450
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 450
ccctggaagg agctgaggaa 20

<210> SEQ ID NO 451
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 451
ttgttgagga aacagtagag 20

<210> SEQ ID NO 452
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 452
gagctttgcc ttcttgccat 20

<210> SEQ ID NO 453
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 453

-continued tttcctcctg aagagctttg 20

<210> SEQ ID NO 454
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 454
atgtggctgc catggctgct 20

<210> SEQ ID NO 455
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 455
gctgaagttt ctcacaggga 20

<210> SEQ ID NO 456
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 456
tgcctgcact cataagctga 20

<210> SEQ ID NO 457
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 457
acagccagtc ccactgctgc 20

<210> SEQ ID NO 458
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 458
ccttgggaga ctactggcca 20

<210> SEQ ID NO 459
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 459
caagtggaga ttcaggtggg 20

<210> SEQ ID NO 460
<211> LENGTH: 20
<212> TYPE: DNA
<213> ORGANISM: Artificial Sequence -continued
<220> FEATURE:
<223> OTHER INFORMATION: Antisense Oligonucleotide

<400> SEQUENCE: 460
ttgaacacaa cctgcctagg 20

<210> SEQ ID NO 461
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 461
gccctttctt gaacacaacc 20

<210> SEQ ID NO 462
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 462
atctggctct gggttgtcct 20

<210> SEQ ID NO 463
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 463
ttggccgggc atctggctct 20

<210> SEQ ID NO 464
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 464
ctcttcaacc ttggccgggc 20

<210> SEQ ID NO 465
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 465
tacaagctgc tgtcttgctg 20

<210> SEQ ID NO 466
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 466
ggcctgtgcc aggctaggac 20

-continued

<210> SEQ ID NO 467
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 467
gcttctccat catatccaac 20

<210> SEQ ID NO 468
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 468
aacactcaga gttcatagat 20

<210> SEQ ID NO 469
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 469
catgggaaca ctcagagttc 20

<210> SEQ ID NO 470
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 470
ctgaaggaca tatctgggta 20

<210> SEQ ID NO 471
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 471
gtaacaaagg cgagaccaag 20

<210> SEQ ID NO 472
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 472
gaggaagtgt caccattagg 20

<210> SEQ ID NO 473
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 473
cagaccagct ctgtgaaggt 20

<210> SEQ ID NO 474
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 474
cggtgctgca ctgggcatgg 20

<210> SEQ ID NO 475
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 475
ctgggctcac cccgtcactg 20

<210> SEQ ID NO 476
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 476
ccaaggatgg gcaacctgac 20

<210> SEQ ID NO 477
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 477
ccttaccaac cggaacttgt 20

<210> SEQ ID NO 478
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 478
cctctcctca ggtgtgctca 20

<210> SEQ ID NO 479
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 479
ccaagcccaa ggcctcatga 20

<210> SEQ ID NO 480

-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 480
ctcaggctgc agaggaccag 20

<210> SEQ ID NO 481
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 481
taggtctctt ccctccactc 20

<210> SEQ ID NO 482
<220> FEATURE:

<400> SEQUENCE: 482

000

<210> SEQ ID NO 483
<220> FEATURE:

<400> SEQUENCE: 483

000

<210> SEQ ID NO 484
<211> LENGTH: 20
<212> TYPE: DNA
<213> ORGANISM: H. sapiens
<220> FEATURE:

<400> SEQUENCE: 484
gcgcgggccc tgaggctcaa 20

<210> SEQ ID NO 485
<211> LENGTH: 20
<212> TYPE: DNA
<213> ORGANISM: H. sapiens
<220> FEATURE:

<400> SEQUENCE: 485
gcagcttcag gggaggacac 20

<210> SEQ ID NO 486
<211> LENGTH: 20
<212> TYPE: DNA
<213> ORGANISM: H. sapiens
<220> FEATURE:

<400> SEQUENCE: 486
cggaggagcg tacacacaca 20

<210> SEQ ID NO 487
<211> LENGTH: 20
<212> TYPE: DNA
<213> ORGANISM: H. sapiens
<220> FEATURE:

<400> SEQUENCE: 487

-continued agcgtacaca cacaccagga 20

<210> SEQ ID NO 488
<211> LENGTH: 20
<212> TYPE: DNA
<213> ORGANISM: H. sapiens
<220> FEATURE:

<400> SEQUENCE: 488
tagctgccca gaggcatgcc 20

<210> SEQ ID NO 489
<211> LENGTH: 20
<212> TYPE: DNA
<213> ORGANISM: H. sapiens
<220> FEATURE:

<400> SEQUENCE: 489
tcgacaagta ttcctgctgg 20

<210> SEQ ID NO 490
<211> LENGTH: 20
<212> TYPE: DNA
<213> ORGANISM: H. sapiens
<220> FEATURE:

<400> SEQUENCE: 490
ggcctgccag ccacaggtcc 20

<210> SEQ ID NO 491
<211> LENGTH: 20
<212> TYPE: DNA
<213> ORGANISM: H. sapiens
<220> FEATURE:

<400> SEQUENCE: 491
ctacggtgac cagtgtcacc 20

<210> SEQ ID NO 492
<211> LENGTH: 20
<212> TYPE: DNA
<213> ORGANISM: H. sapiens
<220> FEATURE:

<400> SEQUENCE: 492
gctggtgtgc aacagaacct 20

<210> SEQ ID NO 493
<211> LENGTH: 20
<212> TYPE: DNA
<213> ORGANISM: H. sapiens
<220> FEATURE:

<400> SEQUENCE: 493
caccacaaag tgcaacaccg 20

<210> SEQ ID NO 494
<211> LENGTH: 20
<212> TYPE: DNA
<213> ORGANISM: H. sapiens
<220> FEATURE:

<400> SEQUENCE: 494
tgccgctgtc tctgccaggg 20

<210> SEQ ID NO 495
<211> LENGTH: 20
<212> TYPE: DNA
<213> ORGANISM: H. sapiens
<220> FEATURE:

<400> SEQUENCE: 495
aacaccgctt cgtgttcaag 20

<210> SEQ ID NO 496
<211> LENGTH: 20
<212> TYPE: DNA
<213> ORGANISM: H. sapiens
<220> FEATURE:

<400> SEQUENCE: 496
tgttcaagag atgcgggccc 20

<210> SEQ ID NO 497
<211> LENGTH: 20
<212> TYPE: DNA
<213> ORGANISM: H. sapiens
<220> FEATURE:

<400> SEQUENCE: 497
gccactgtaa ctcgcagaag 20

<210> SEQ ID NO 498
<211> LENGTH: 20
<212> TYPE: DNA
<213> ORGANISM: H. sapiens
<220> FEATURE:

<400> SEQUENCE: 498
gcgaggagat tgaggtccag 20

<210> SEQ ID NO 499
<211> LENGTH: 20
<212> TYPE: DNA
<213> ORGANISM: H. sapiens
<220> FEATURE:

<400> SEQUENCE: 499
aggtccagaa ggaggtggcc 20

<210> SEQ ID NO 500
<211> LENGTH: 20
<212> TYPE: DNA
<213> ORGANISM: H. sapiens
<220> FEATURE:

<400> SEQUENCE: 500
ccaagatgta cagcagcttc 20

<210> SEQ ID NO 501
<211> LENGTH: 20
<212> TYPE: DNA
<213> ORGANISM: H. sapiens
<220> FEATURE:

<400> SEQUENCE: 501
cgccttggcc atcctggggg 20

-continued

<210> SEQ ID NO 502
<211> LENGTH: 20
<212> TYPE: DNA
<213> ORGANISM: H. sapiens
<220> FEATURE:

<400> SEQUENCE: 502
gtgctgaaag ccagctccgt 20

<210> SEQ ID NO 503
<211> LENGTH: 20
<212> TYPE: DNA
<213> ORGANISM: H. sapiens
<220> FEATURE:

<400> SEQUENCE: 503
ctgctcagga cccgctacag 20

<210> SEQ ID NO 504
<211> LENGTH: 20
<212> TYPE: DNA
<213> ORGANISM: H. sapiens
<220> FEATURE:

<400> SEQUENCE: 504
aggacccgct acagccagaa 20

<210> SEQ ID NO 505
<211> LENGTH: 20
<212> TYPE: DNA
<213> ORGANISM: H. sapiens
<220> FEATURE:

<400> SEQUENCE: 505
gctacagcca gaaaattggc 20

<210> SEQ ID NO 506
<211> LENGTH: 20
<212> TYPE: DNA
<213> ORGANISM: H. sapiens
<220> FEATURE:

<400> SEQUENCE: 506
gaaaattggc gacgacctca 20

<210> SEQ ID NO 507
<211> LENGTH: 20
<212> TYPE: DNA
<213> ORGANISM: H. sapiens
<220> FEATURE:

<400> SEQUENCE: 507
cgacgacctc agtgtcagca 20

<210> SEQ ID NO 508
<211> LENGTH: 20
<212> TYPE: DNA
<213> ORGANISM: H. sapiens
<220> FEATURE:

<400> SEQUENCE: 508
cctcagtgtc agcacctggc 20

<210> SEQ ID NO 509
<211> LENGTH: 20

-continued

<212> TYPE: DNA
<213> ORGANISM: H. sapiens
<220> FEATURE:

<400> SEQUENCE: 509
tcatgcaata tggcatcgtg 20

<210> SEQ ID NO 510
<211> LENGTH: 20
<212> TYPE: DNA
<213> ORGANISM: H. sapiens
<220> FEATURE:

<400> SEQUENCE: 510
aacctgctgg gcctggccac 20

<210> SEQ ID NO 511
<211> LENGTH: 20
<212> TYPE: DNA
<213> ORGANISM: H. sapiens
<220> FEATURE:

<400> SEQUENCE: 511
gggcagtggt caagtgtctg 20

<210> SEQ ID NO 512
<211> LENGTH: 20
<212> TYPE: DNA
<213> ORGANISM: H. sapiens
<220> FEATURE:

<400> SEQUENCE: 512
gcttctggtg gatcctgcgg 20

<210> SEQ ID NO 513
<211> LENGTH: 20
<212> TYPE: DNA
<213> ORGANISM: H. sapiens
<220> FEATURE:

<400> SEQUENCE: 513
cttcctggcc atcctgatca 20

<210> SEQ ID NO 514
<211> LENGTH: 20
<212> TYPE: DNA
<213> ORGANISM: H. sapiens
<220> FEATURE:

<400> SEQUENCE: 514
caacttcttc atcttcgtcc 20

<210> SEQ ID NO 515
<211> LENGTH: 20
<212> TYPE: DNA
<213> ORGANISM: H. sapiens
<220> FEATURE:

<400> SEQUENCE: 515
ctgcgggcac ggcagatgca 20

<210> SEQ ID NO 516
<211> LENGTH: 20
<212> TYPE: DNA
<213> ORGANISM: H. sapiens

-continued

<220> FEATURE:

<400> SEQUENCE: 516
ctggcgcctg ggcaaagtgc 20

<210> SEQ ID NO 517
<211> LENGTH: 20
<212> TYPE: DNA
<213> ORGANISM: H. sapiens
<220> FEATURE:

<400> SEQUENCE: 517
gcaaagtgct atgggaggag 20

<210> SEQ ID NO 518
<211> LENGTH: 20
<212> TYPE: DNA
<213> ORGANISM: H. sapiens
<220> FEATURE:

<400> SEQUENCE: 518
ccagcaagga gctgcagttt 20

<210> SEQ ID NO 519
<211> LENGTH: 20
<212> TYPE: DNA
<213> ORGANISM: H. sapiens
<220> FEATURE:

<400> SEQUENCE: 519
tggtggcagc caggattcat 20

<210> SEQ ID NO 520
<211> LENGTH: 20
<212> TYPE: DNA
<213> ORGANISM: H. sapiens
<220> FEATURE:

<400> SEQUENCE: 520
ttggctggtg gcctccctag 20

<210> SEQ ID NO 521
<211> LENGTH: 20
<212> TYPE: DNA
<213> ORGANISM: H. sapiens
<220> FEATURE:

<400> SEQUENCE: 521
cctccctaga ttggctgaga 20

<210> SEQ ID NO 522
<211> LENGTH: 20
<212> TYPE: DNA
<213> ORGANISM: H. sapiens
<220> FEATURE:

<400> SEQUENCE: 522
cattgggtca cctgcaggaa 20

<210> SEQ ID NO 523
<211> LENGTH: 20
<212> TYPE: DNA
<213> ORGANISM: H. sapiens
<220> FEATURE:

-continued

<400> SEQUENCE: 523
cagtgtggct gtctgcgaga 20

<210> SEQ ID NO 524
<211> LENGTH: 20
<212> TYPE: DNA
<213> ORGANISM: H. sapiens
<220> FEATURE:

<400> SEQUENCE: 524
tgcgagattg ggcctcctct 20

<210> SEQ ID NO 525
<211> LENGTH: 20
<212> TYPE: DNA
<213> ORGANISM: H. sapiens
<220> FEATURE:

<400> SEQUENCE: 525
gaggtgagca gaggagtcca 20

<210> SEQ ID NO 526
<211> LENGTH: 20
<212> TYPE: DNA
<213> ORGANISM: H. sapiens
<220> FEATURE:

<400> SEQUENCE: 526
gtgccgtgaa ctgcgtgcca 20

<210> SEQ ID NO 527
<211> LENGTH: 20
<212> TYPE: DNA
<213> ORGANISM: H. sapiens
<220> FEATURE:

<400> SEQUENCE: 527
tatgtcggca cgtcccatgt 20

<210> SEQ ID NO 528
<211> LENGTH: 20
<212> TYPE: DNA
<213> ORGANISM: H. sapiens
<220> FEATURE:

<400> SEQUENCE: 528
acgtcccatg tgcatggaaa 20

<210> SEQ ID NO 529
<211> LENGTH: 20
<212> TYPE: DNA
<213> ORGANISM: H. sapiens
<220> FEATURE:

<400> SEQUENCE: 529
gcatggaaat gtcctccaac 20

<210> SEQ ID NO 530
<211> LENGTH: 20
<212> TYPE: DNA
<213> ORGANISM: H. sapiens
<220> FEATURE:

<400> SEQUENCE: 530

-continued ggtaactgag ccacagagct 20

<210> SEQ ID NO 531
<211> LENGTH: 20
<212> TYPE: DNA
<213> ORGANISM: H. sapiens
<220> FEATURE:

<400> SEQUENCE: 531
tgtgccacag caagctgcac 20

<210> SEQ ID NO 532
<211> LENGTH: 20
<212> TYPE: DNA
<213> ORGANISM: H. sapiens
<220> FEATURE:

<400> SEQUENCE: 532
cctgtaccaa gcggttgctg 20

<210> SEQ ID NO 533
<211> LENGTH: 20
<212> TYPE: DNA
<213> ORGANISM: H. sapiens
<220> FEATURE:

<400> SEQUENCE: 533
gtctctccag ggcctgctgg 20

<210> SEQ ID NO 534
<211> LENGTH: 20
<212> TYPE: DNA
<213> ORGANISM: H. sapiens
<220> FEATURE:

<400> SEQUENCE: 534
cgggccctga ggctcaaagg 20

<210> SEQ ID NO 535
<211> LENGTH: 20
<212> TYPE: DNA
<213> ORGANISM: H. sapiens
<220> FEATURE:

<400> SEQUENCE: 535
tgctgctctg ccactcagct 20

<210> SEQ ID NO 536
<211> LENGTH: 20
<212> TYPE: DNA
<213> ORGANISM: H. sapiens
<220> FEATURE:

<400> SEQUENCE: 536
ctgctctgcc actcagctgc 20

<210> SEQ ID NO 537
<211> LENGTH: 20
<212> TYPE: DNA
<213> ORGANISM: H. sapiens
<220> FEATURE:

<400> SEQUENCE: 537
ctcggaggag cgtacacaca 20

-continued

<210> SEQ ID NO 538
<211> LENGTH: 20
<212> TYPE: DNA
<213> ORGANISM: H. sapiens
<220> FEATURE:

<400> SEQUENCE: 538
gaggagcgta cacacacacc 20

<210> SEQ ID NO 539
<211> LENGTH: 20
<212> TYPE: DNA
<213> ORGANISM: H. sapiens
<220> FEATURE:

<400> SEQUENCE: 539
ggagcgtaca cacacaccag 20

<210> SEQ ID NO 540
<211> LENGTH: 20
<212> TYPE: DNA
<213> ORGANISM: H. sapiens
<220> FEATURE:

<400> SEQUENCE: 540
acaccaggac tgcattgccc 20

<210> SEQ ID NO 541
<211> LENGTH: 20
<212> TYPE: DNA
<213> ORGANISM: H. sapiens
<220> FEATURE:

<400> SEQUENCE: 541
cagatgtggg aggcagctag 20

<210> SEQ ID NO 542
<211> LENGTH: 20
<212> TYPE: DNA
<213> ORGANISM: H. sapiens
<220> FEATURE:

<400> SEQUENCE: 542
atgtgggagg cagctagctg 20

<210> SEQ ID NO 543
<211> LENGTH: 20
<212> TYPE: DNA
<213> ORGANISM: H. sapiens
<220> FEATURE:

<400> SEQUENCE: 543
ggcagctagc tgcccagagg 20

<210> SEQ ID NO 544
<211> LENGTH: 20
<212> TYPE: DNA
<213> ORGANISM: H. sapiens
<220> FEATURE:

<400> SEQUENCE: 544
ctagctgccc agaggcatgc 20

<210> SEQ ID NO 545

-continued

<211> LENGTH: 20
<212> TYPE: DNA
<213> ORGANISM: H. sapiens
<220> FEATURE:

<400> SEQUENCE: 545
gctggcctgc cagccacagg 20

<210> SEQ ID NO 546
<211> LENGTH: 20
<212> TYPE: DNA
<213> ORGANISM: H. sapiens
<220> FEATURE:

<400> SEQUENCE: 546
cctgtttgag aagtggaagc 20

<210> SEQ ID NO 547
<211> LENGTH: 20
<212> TYPE: DNA
<213> ORGANISM: H. sapiens
<220> FEATURE:

<400> SEQUENCE: 547
ttgagaagtg gaagctctac 20

<210> SEQ ID NO 548
<211> LENGTH: 20
<212> TYPE: DNA
<213> ORGANISM: H. sapiens
<220> FEATURE:

<400> SEQUENCE: 548
caccacaacc tgagcctgct 20

<210> SEQ ID NO 549
<211> LENGTH: 20
<212> TYPE: DNA
<213> ORGANISM: H. sapiens
<220> FEATURE:

<400> SEQUENCE: 549
cttggcacca caaagtgcaa 20

<210> SEQ ID NO 550
<211> LENGTH: 20
<212> TYPE: DNA
<213> ORGANISM: H. sapiens
<220> FEATURE:

<400> SEQUENCE: 550
ttggcaccac aaagtgcaac 20

<210> SEQ ID NO 551
<211> LENGTH: 20
<212> TYPE: DNA
<213> ORGANISM: H. sapiens
<220> FEATURE:

<400> SEQUENCE: 551
tggcaccaca aagtgcaaca 20

<210> SEQ ID NO 552
<211> LENGTH: 20
<212> TYPE: DNA

-continued

<213> ORGANISM: H. sapiens
<220> FEATURE:

<400> SEQUENCE: 552
ggcaccacaa agtgcaacac 20

<210> SEQ ID NO 553
<211> LENGTH: 20
<212> TYPE: DNA
<213> ORGANISM: H. sapiens
<220> FEATURE:

<400> SEQUENCE: 553
gtgttcaaga gatgcgggcc 20

<210> SEQ ID NO 554
<211> LENGTH: 20
<212> TYPE: DNA
<213> ORGANISM: H. sapiens
<220> FEATURE:

<400> SEQUENCE: 554
tcaagagatg cgggcccgac 20

<210> SEQ ID NO 555
<211> LENGTH: 20
<212> TYPE: DNA
<213> ORGANISM: H. sapiens
<220> FEATURE:

<400> SEQUENCE: 555
ccttggcgtg atgcctccca 20

<210> SEQ ID NO 556
<211> LENGTH: 20
<212> TYPE: DNA
<213> ORGANISM: H. sapiens
<220> FEATURE:

<400> SEQUENCE: 556
atgcctccca gtgccagatg 20

<210> SEQ ID NO 557
<211> LENGTH: 20
<212> TYPE: DNA
<213> ORGANISM: H. sapiens
<220> FEATURE:

<400> SEQUENCE: 557
tccagaagga ggtggccaag 20

<210> SEQ ID NO 558
<211> LENGTH: 20
<212> TYPE: DNA
<213> ORGANISM: H. sapiens
<220> FEATURE:

<400> SEQUENCE: 558
gatgtacagc agcttccagg 20

<210> SEQ ID NO 559
<211> LENGTH: 20
<212> TYPE: DNA
<213> ORGANISM: H. sapiens
<220> FEATURE:

-continued

<400> SEQUENCE: 559
gcaatgccat ccacgcgaat 20

<210> SEQ ID NO 560
<211> LENGTH: 20
<212> TYPE: DNA
<213> ORGANISM: H. sapiens
<220> FEATURE:

<400> SEQUENCE: 560
atgggctgct caggacccgc 20

<210> SEQ ID NO 561
<211> LENGTH: 20
<212> TYPE: DNA
<213> ORGANISM: H. sapiens
<220> FEATURE:

<400> SEQUENCE: 561
ccagaaaatt ggcgacgacc 20

<210> SEQ ID NO 562
<211> LENGTH: 20
<212> TYPE: DNA
<213> ORGANISM: H. sapiens
<220> FEATURE:

<400> SEQUENCE: 562
acgacctcag tgtcagcacc 20

<210> SEQ ID NO 563
<211> LENGTH: 20
<212> TYPE: DNA
<213> ORGANISM: H. sapiens
<220> FEATURE:

<400> SEQUENCE: 563
tgctgggcct ggccaccctc 20

<210> SEQ ID NO 564
<211> LENGTH: 20
<212> TYPE: DNA
<213> ORGANISM: H. sapiens
<220> FEATURE:

<400> SEQUENCE: 564
gctggaccag caatgacaac 20

<210> SEQ ID NO 565
<211> LENGTH: 20
<212> TYPE: DNA
<213> ORGANISM: H. sapiens
<220> FEATURE:

<400> SEQUENCE: 565
caatgacaac atgggcttct 20

<210> SEQ ID NO 566
<211> LENGTH: 20
<212> TYPE: DNA
<213> ORGANISM: H. sapiens
<220> FEATURE:

<400> SEQUENCE: 566

-continued tggtggatcc tgcggttccc 20

<210> SEQ ID NO 567
<211> LENGTH: 20
<212> TYPE: DNA
<213> ORGANISM: H. sapiens
<220> FEATURE:

<400> SEQUENCE: 567
acttcttcat cttcgtccgc 20

<210> SEQ ID NO 568
<211> LENGTH: 20
<212> TYPE: DNA
<213> ORGANISM: H. sapiens
<220> FEATURE:

<400> SEQUENCE: 568
gtggcagcca ggattcatct 20

<210> SEQ ID NO 569
<211> LENGTH: 20
<212> TYPE: DNA
<213> ORGANISM: H. sapiens
<220> FEATURE:

<400> SEQUENCE: 569
cagctagggc tggactctgg 20

<210> SEQ ID NO 570
<211> LENGTH: 20
<212> TYPE: DNA
<213> ORGANISM: H. sapiens
<220> FEATURE:

<400> SEQUENCE: 570
agggctggac tctggcaccc 20

<210> SEQ ID NO 571
<211> LENGTH: 20
<212> TYPE: DNA
<213> ORGANISM: H. sapiens
<220> FEATURE:

<400> SEQUENCE: 571
gctggactct ggcacccaga 20

<210> SEQ ID NO 572
<211> LENGTH: 20
<212> TYPE: DNA
<213> ORGANISM: H. sapiens
<220> FEATURE:

<400> SEQUENCE: 572
ctggactctg gcacccagag 20

<210> SEQ ID NO 573
<211> LENGTH: 20
<212> TYPE: DNA
<213> ORGANISM: H. sapiens
<220> FEATURE:

<400> SEQUENCE: 573
tggactctgg cacccagagg 20

<210> SEQ ID NO 574
<211> LENGTH: 20
<212> TYPE: DNA
<213> ORGANISM: H. sapiens
<220> FEATURE:

<400> SEQUENCE: 574
actctggcac ccagaggcgt 20

<210> SEQ ID NO 575
<211> LENGTH: 20
<212> TYPE: DNA
<213> ORGANISM: H. sapiens
<220> FEATURE:

<400> SEQUENCE: 575
cgctggacaa cccagaactg 20

<210> SEQ ID NO 576
<211> LENGTH: 20
<212> TYPE: DNA
<213> ORGANISM: H. sapiens
<220> FEATURE:

<400> SEQUENCE: 576
ctgtctgcga gattgggcct 20

<210> SEQ ID NO 577
<211> LENGTH: 20
<212> TYPE: DNA
<213> ORGANISM: H. sapiens
<220> FEATURE:

<400> SEQUENCE: 577
tgtctgcgag attgggcctc 20

<210> SEQ ID NO 578
<211> LENGTH: 20
<212> TYPE: DNA
<213> ORGANISM: H. sapiens
<220> FEATURE:

<400> SEQUENCE: 578
cgagattggg cctcctctcc 20

<210> SEQ ID NO 579
<211> LENGTH: 20
<212> TYPE: DNA
<213> ORGANISM: H. sapiens
<220> FEATURE:

<400> SEQUENCE: 579
ttgggcctcc tctccctgca 20

<210> SEQ ID NO 580
<211> LENGTH: 20
<212> TYPE: DNA
<213> ORGANISM: H. sapiens
<220> FEATURE:

<400> SEQUENCE: 580
tgccttgtcc ctggtgcaga 20

-continued

<210> SEQ ID NO 581
<211> LENGTH: 20
<212> TYPE: DNA
<213> ORGANISM: H. sapiens
<220> FEATURE:

<400> SEQUENCE: 581
ccctggtgca gaggtgagca 20

<210> SEQ ID NO 582
<211> LENGTH: 20
<212> TYPE: DNA
<213> ORGANISM: H. sapiens
<220> FEATURE:

<400> SEQUENCE: 582
tgagcagagg agtccagggc 20

<210> SEQ ID NO 583
<211> LENGTH: 20
<212> TYPE: DNA
<213> ORGANISM: H. sapiens
<220> FEATURE:

<400> SEQUENCE: 583
ggggctgtgc cgtgaactgc 20

<210> SEQ ID NO 584
<211> LENGTH: 20
<212> TYPE: DNA
<213> ORGANISM: H. sapiens
<220> FEATURE:

<400> SEQUENCE: 584
gaactgcgtg ccagtgtccc 20

<210> SEQ ID NO 585
<211> LENGTH: 20
<212> TYPE: DNA
<213> ORGANISM: H. sapiens
<220> FEATURE:

<400> SEQUENCE: 585
tgtcggcacg tcccatgtgc 20

<210> SEQ ID NO 586
<211> LENGTH: 20
<212> TYPE: DNA
<213> ORGANISM: H. sapiens
<220> FEATURE:

<400> SEQUENCE: 586
catgtgcatg gaaatgtcct 20

<210> SEQ ID NO 587
<211> LENGTH: 20
<212> TYPE: DNA
<213> ORGANISM: H. sapiens
<220> FEATURE:

<400> SEQUENCE: 587
tgtgcatgga aatgtcctcc 20

<210> SEQ ID NO 588
<211> LENGTH: 20

-continued

<212> TYPE: DNA
<213> ORGANISM: H. sapiens
<220> FEATURE:

<400> SEQUENCE: 588
gtcctccaac aataaagagc 20

<210> SEQ ID NO 589
<211> LENGTH: 20
<212> TYPE: DNA
<213> ORGANISM: H. sapiens
<220> FEATURE:

<400> SEQUENCE: 589
cctccaacaa taaagagctc 20

<210> SEQ ID NO 590
<211> LENGTH: 20
<212> TYPE: DNA
<213> ORGANISM: H. sapiens
<220> FEATURE:

<400> SEQUENCE: 590
caataaagag ctcaagtggt 20

<210> SEQ ID NO 591
<211> LENGTH: 20
<212> TYPE: DNA
<213> ORGANISM: H. sapiens
<220> FEATURE:

<400> SEQUENCE: 591
ctggggacgc caaaactgcc 20

<210> SEQ ID NO 592
<211> LENGTH: 20
<212> TYPE: DNA
<213> ORGANISM: H. sapiens
<220> FEATURE:

<400> SEQUENCE: 592
tagacacgca catcctatcc 20

<210> SEQ ID NO 593
<211> LENGTH: 20
<212> TYPE: DNA
<213> ORGANISM: H. sapiens
<220> FEATURE:

<400> SEQUENCE: 593
ctaccctgca gagctggtgt 20

<210> SEQ ID NO 594
<211> LENGTH: 20
<212> TYPE: DNA
<213> ORGANISM: H. sapiens
<220> FEATURE:

<400> SEQUENCE: 594
gcagctagct gcccagaggc 20

<210> SEQ ID NO 595
<211> LENGTH: 20
<212> TYPE: DNA
<213> ORGANISM: H. sapiens

-continued

<220> FEATURE:

<400> SEQUENCE: 595
ctgctgctgc tggcctgcca 20

<210> SEQ ID NO 596
<211> LENGTH: 20
<212> TYPE: DNA
<213> ORGANISM: H. sapiens
<220> FEATURE:

<400> SEQUENCE: 596
tgctgctggc ctgccagcca 20

<210> SEQ ID NO 597
<211> LENGTH: 20
<212> TYPE: DNA
<213> ORGANISM: H. sapiens
<220> FEATURE:

<400> SEQUENCE: 597
ccctccgctc aggtgatgga 20

<210> SEQ ID NO 598
<211> LENGTH: 20
<212> TYPE: DNA
<213> ORGANISM: H. sapiens
<220> FEATURE:

<400> SEQUENCE: 598
gacttcctgt ttgagaagtg 20

<210> SEQ ID NO 599
<211> LENGTH: 20
<212> TYPE: DNA
<213> ORGANISM: H. sapiens
<220> FEATURE:

<400> SEQUENCE: 599
tgaccagtgt caccacaacc 20

<210> SEQ ID NO 600
<211> LENGTH: 20
<212> TYPE: DNA
<213> ORGANISM: H. sapiens
<220> FEATURE:

<400> SEQUENCE: 600
gtgtcaccac aacctgagcc 20

<210> SEQ ID NO 601
<211> LENGTH: 20
<212> TYPE: DNA
<213> ORGANISM: H. sapiens
<220> FEATURE:

<400> SEQUENCE: 601
aacagaacct tcgacaagta 20

<210> SEQ ID NO 602
<211> LENGTH: 20
<212> TYPE: DNA
<213> ORGANISM: H. sapiens
<220> FEATURE:

-continued

<400> SEQUENCE: 602
accttcgaca agtattcctg 20

<210> SEQ ID NO 603
<211> LENGTH: 20
<212> TYPE: DNA
<213> ORGANISM: H. sapiens
<220> FEATURE:

<400> SEQUENCE: 603
cgccaatacc acggccaaca 20

<210> SEQ ID NO 604
<211> LENGTH: 20
<212> TYPE: DNA
<213> ORGANISM: H. sapiens
<220> FEATURE:

<400> SEQUENCE: 604
aataccacgg ccaacatctc 20

<210> SEQ ID NO 605
<211> LENGTH: 20
<212> TYPE: DNA
<213> ORGANISM: H. sapiens
<220> FEATURE:

<400> SEQUENCE: 605
accacggcca acatctcctg 20

<210> SEQ ID NO 606
<211> LENGTH: 20
<212> TYPE: DNA
<213> ORGANISM: H. sapiens
<220> FEATURE:

<400> SEQUENCE: 606
gccttggcac cacaaagtgc 20

<210> SEQ ID NO 607
<211> LENGTH: 20
<212> TYPE: DNA
<213> ORGANISM: H. sapiens
<220> FEATURE:

<400> SEQUENCE: 607
accacaaagt gcaacaccgc 20

<210> SEQ ID NO 608
<211> LENGTH: 20
<212> TYPE: DNA
<213> ORGANISM: H. sapiens
<220> FEATURE:

<400> SEQUENCE: 608
caaagtgcaa caccgcttcg 20

<210> SEQ ID NO 609
<211> LENGTH: 20
<212> TYPE: DNA
<213> ORGANISM: H. sapiens
<220> FEATURE:

<400> SEQUENCE: 609

-continued gtgcaacacc gcttcgtgtt 20

<210> SEQ ID NO 610
<211> LENGTH: 20
<212> TYPE: DNA
<213> ORGANISM: H. sapiens
<220> FEATURE:

<400> SEQUENCE: 610
ccgcttcgtg ttcaagagat 20

<210> SEQ ID NO 611
<211> LENGTH: 20
<212> TYPE: DNA
<213> ORGANISM: H. sapiens
<220> FEATURE:

<400> SEQUENCE: 611
gtcagtgggt gcgtggaccc 20

<210> SEQ ID NO 612
<211> LENGTH: 20
<212> TYPE: DNA
<213> ORGANISM: H. sapiens
<220> FEATURE:

<400> SEQUENCE: 612
cccgggggca gccttggcgt 20

<210> SEQ ID NO 613
<211> LENGTH: 20
<212> TYPE: DNA
<213> ORGANISM: H. sapiens
<220> FEATURE:

<400> SEQUENCE: 613
aagatgtaca gcagcttcca 20

<210> SEQ ID NO 614
<211> LENGTH: 20
<212> TYPE: DNA
<213> ORGANISM: H. sapiens
<220> FEATURE:

<400> SEQUENCE: 614
tgtacagcag cttccaggtg 20

<210> SEQ ID NO 615
<211> LENGTH: 20
<212> TYPE: DNA
<213> ORGANISM: H. sapiens
<220> FEATURE:

<400> SEQUENCE: 615
cagcagcttc caggtgatgt 20

<210> SEQ ID NO 616
<211> LENGTH: 20
<212> TYPE: DNA
<213> ORGANISM: H. sapiens
<220> FEATURE:

<400> SEQUENCE: 616
agcttccagg tgatgtacac 20

-continued

<210> SEQ ID NO 617
<211> LENGTH: 20
<212> TYPE: DNA
<213> ORGANISM: H. sapiens
<220> FEATURE:

<400> SEQUENCE: 617
gctacagcct gtccctgggg 20

<210> SEQ ID NO 618
<211> LENGTH: 20
<212> TYPE: DNA
<213> ORGANISM: H. sapiens
<220> FEATURE:

<400> SEQUENCE: 618
acagcctgtc cctgggggcc 20

<210> SEQ ID NO 619
<211> LENGTH: 20
<212> TYPE: DNA
<213> ORGANISM: H. sapiens
<220> FEATURE:

<400> SEQUENCE: 619
gatgggctgc tcaggacccg 20

<210> SEQ ID NO 620
<211> LENGTH: 20
<212> TYPE: DNA
<213> ORGANISM: H. sapiens
<220> FEATURE:

<400> SEQUENCE: 620
ggctgctcag gacccgctac 20

<210> SEQ ID NO 621
<211> LENGTH: 20
<212> TYPE: DNA
<213> ORGANISM: H. sapiens
<220> FEATURE:

<400> SEQUENCE: 621
gctcaggacc cgctacagcc 20

<210> SEQ ID NO 622
<211> LENGTH: 20
<212> TYPE: DNA
<213> ORGANISM: H. sapiens
<220> FEATURE:

<400> SEQUENCE: 622
ctggctcagt gatggagcgg 20

<210> SEQ ID NO 623
<211> LENGTH: 20
<212> TYPE: DNA
<213> ORGANISM: H. sapiens
<220> FEATURE:

<400> SEQUENCE: 623
ctcagtgatg gagcggtggc 20

<210> SEQ ID NO 624

-continued

<211> LENGTH: 20
<212> TYPE: DNA
<213> ORGANISM: H. sapiens
<220> FEATURE:

<400> SEQUENCE: 624
gtgtggccgc ggtgttcatg 20

<210> SEQ ID NO 625
<211> LENGTH: 20
<212> TYPE: DNA
<213> ORGANISM: H. sapiens
<220> FEATURE:

<400> SEQUENCE: 625
ggccgcggtg ttcatgcaat 20

<210> SEQ ID NO 626
<211> LENGTH: 20
<212> TYPE: DNA
<213> ORGANISM: H. sapiens
<220> FEATURE:

<400> SEQUENCE: 626
cggtgttcat gcaatatggc 20

<210> SEQ ID NO 627
<211> LENGTH: 20
<212> TYPE: DNA
<213> ORGANISM: H. sapiens
<220> FEATURE:

<400> SEQUENCE: 627
tacctgcaca acctgctggg 20

<210> SEQ ID NO 628
<211> LENGTH: 20
<212> TYPE: DNA
<213> ORGANISM: H. sapiens
<220> FEATURE:

<400> SEQUENCE: 628
cacaacctgc tgggcctggc 20

<210> SEQ ID NO 629
<211> LENGTH: 20
<212> TYPE: DNA
<213> ORGANISM: H. sapiens
<220> FEATURE:

<400> SEQUENCE: 629
acctgctggg cctggccacc 20

<210> SEQ ID NO 630
<211> LENGTH: 20
<212> TYPE: DNA
<213> ORGANISM: H. sapiens
<220> FEATURE:

<400> SEQUENCE: 630
gagaggagct tcttcagcct 20

<210> SEQ ID NO 631
<211> LENGTH: 20
<212> TYPE: DNA

-continued

<213> ORGANISM: H. sapiens
<220> FEATURE:

<400> SEQUENCE: 631
ggagcttctt cagcctctac 20

<210> SEQ ID NO 632
<211> LENGTH: 20
<212> TYPE: DNA
<213> ORGANISM: H. sapiens
<220> FEATURE:

<400> SEQUENCE: 632
tcagcctcta cctgggcatc 20

<210> SEQ ID NO 633
<211> LENGTH: 20
<212> TYPE: DNA
<213> ORGANISM: H. sapiens
<220> FEATURE:

<400> SEQUENCE: 633
cctctacctg ggcatcggct 20

<210> SEQ ID NO 634
<211> LENGTH: 20
<212> TYPE: DNA
<213> ORGANISM: H. sapiens
<220> FEATURE:

<400> SEQUENCE: 634
gtgctggacc agcaatgaca 20

<210> SEQ ID NO 635
<211> LENGTH: 20
<212> TYPE: DNA
<213> ORGANISM: H. sapiens
<220> FEATURE:

<400> SEQUENCE: 635
tggaccagca atgacaacat 20

<210> SEQ ID NO 636
<211> LENGTH: 20
<212> TYPE: DNA
<213> ORGANISM: H. sapiens
<220> FEATURE:

<400> SEQUENCE: 636
gcaatgacaa catgggcttc 20

<210> SEQ ID NO 637
<211> LENGTH: 20
<212> TYPE: DNA
<213> ORGANISM: H. sapiens
<220> FEATURE:

<400> SEQUENCE: 637
acaacatggg cttctggtgg 20

<210> SEQ ID NO 638
<211> LENGTH: 20
<212> TYPE: DNA
<213> ORGANISM: H. sapiens
<220> FEATURE:

-continued

<400> SEQUENCE: 638
acatgggctt ctggtggatc 20

<210> SEQ ID NO 639
<211> LENGTH: 20
<212> TYPE: DNA
<213> ORGANISM: H. sapiens
<220> FEATURE:

<400> SEQUENCE: 639
tctggtggat cctgcggttc 20

<210> SEQ ID NO 640
<211> LENGTH: 20
<212> TYPE: DNA
<213> ORGANISM: H. sapiens
<220> FEATURE:

<400> SEQUENCE: 640
tcttcctggc catcctgatc 20

<210> SEQ ID NO 641
<211> LENGTH: 20
<212> TYPE: DNA
<213> ORGANISM: H. sapiens
<220> FEATURE:

<400> SEQUENCE: 641
tgcaccacac agactacaag 20

<210> SEQ ID NO 642
<211> LENGTH: 20
<212> TYPE: DNA
<213> ORGANISM: H. sapiens
<220> FEATURE:

<400> SEQUENCE: 642
cgccaagctc ttcttcgacc 20

<210> SEQ ID NO 643
<211> LENGTH: 20
<212> TYPE: DNA
<213> ORGANISM: H. sapiens
<220> FEATURE:

<400> SEQUENCE: 643
cttggctggt ggcctcccta 20

<210> SEQ ID NO 644
<211> LENGTH: 20
<212> TYPE: DNA
<213> ORGANISM: H. sapiens
<220> FEATURE:

<400> SEQUENCE: 644
atgtacagca gcttccaggt 20

<210> SEQ ID NO 645
<211> LENGTH: 20
<212> TYPE: DNA
<213> ORGANISM: H. sapiens
<220> FEATURE:

<400> SEQUENCE: 645

-continued ttcttcgacc tcttcctcag 20

<210> SEQ ID NO 646
<211> LENGTH: 20
<212> TYPE: DNA
<213> ORGANISM: H. sapiens
<220> FEATURE:

<400> SEQUENCE: 646
tcctggccat cctgatcaac 20

<210> SEQ ID NO 647
<211> LENGTH: 20
<212> TYPE: DNA
<213> ORGANISM: H. sapiens
<220> FEATURE:

<400> SEQUENCE: 647
gcttcttcag cctctacctg 20

<210> SEQ ID NO 648
<211> LENGTH: 20
<212> TYPE: DNA
<213> ORGANISM: H. sapiens
<220> FEATURE:

<400> SEQUENCE: 648
cttcgtgttc aagagatgcg 20

<210> SEQ ID NO 649
<211> LENGTH: 20
<212> TYPE: DNA
<213> ORGANISM: H. sapiens
<220> FEATURE:

<400> SEQUENCE: 649
acaaagtgca acaccgcttc 20

<210> SEQ ID NO 650
<211> LENGTH: 20
<212> TYPE: DNA
<213> ORGANISM: H. sapiens
<220> FEATURE:

<400> SEQUENCE: 650
acaacctgct gggcctggcc 20

<210> SEQ ID NO 651
<211> LENGTH: 20
<212> TYPE: DNA
<213> ORGANISM: H. sapiens
<220> FEATURE:

<400> SEQUENCE: 651
agcctctacc tgggcatcgg 20

<210> SEQ ID NO 652
<211> LENGTH: 20
<212> TYPE: DNA
<213> ORGANISM: H. sapiens
<220> FEATURE:

<400> SEQUENCE: 652
caataccacg gccaacatct 20

<210> SEQ ID NO 653
<211> LENGTH: 20
<212> TYPE: DNA
<213> ORGANISM: H. sapiens
<220> FEATURE:

<400> SEQUENCE: 653
accagtgtca ccacaacctg 20

<210> SEQ ID NO 654
<211> LENGTH: 20
<212> TYPE: DNA
<213> ORGANISM: H. sapiens
<220> FEATURE:

<400> SEQUENCE: 654
tacggtgacc agtgtcacca 20

<210> SEQ ID NO 655
<211> LENGTH: 20
<212> TYPE: DNA
<213> ORGANISM: H. sapiens
<220> FEATURE:

<400> SEQUENCE: 655
agtgtcacca caacctgagc 20

<210> SEQ ID NO 656
<211> LENGTH: 20
<212> TYPE: DNA
<213> ORGANISM: H. sapiens
<220> FEATURE:

<400> SEQUENCE: 656
ccttggcacc acaaagtgca 20

<210> SEQ ID NO 657
<211> LENGTH: 20
<212> TYPE: DNA
<213> ORGANISM: H. sapiens
<220> FEATURE:

<400> SEQUENCE: 657
tacagcagct tccaggtgat 20

<210> SEQ ID NO 658
<211> LENGTH: 20
<212> TYPE: DNA
<213> ORGANISM: H. sapiens
<220> FEATURE:

<400> SEQUENCE: 658
gccgcggtgt tcatgcaata 20

<210> SEQ ID NO 659
<211> LENGTH: 20
<212> TYPE: DNA
<213> ORGANISM: H. sapiens
<220> FEATURE:

<400> SEQUENCE: 659
accgcttcgt gttcaagaga 20

-continued

<210> SEQ ID NO 660
<211> LENGTH: 20
<212> TYPE: DNA
<213> ORGANISM: H. sapiens
<220> FEATURE:

<400> SEQUENCE: 660
acaccgcttc gtgttcaaga 20

<210> SEQ ID NO 661
<211> LENGTH: 20
<212> TYPE: DNA
<213> ORGANISM: H. sapiens
<220> FEATURE:

<400> SEQUENCE: 661
caacctgctg ggcctggcca 20

<210> SEQ ID NO 662
<211> LENGTH: 20
<212> TYPE: DNA
<213> ORGANISM: H. sapiens
<220> FEATURE:

<400> SEQUENCE: 662
caggacccgc tacagccaga 20

<210> SEQ ID NO 663
<211> LENGTH: 20
<212> TYPE: DNA
<213> ORGANISM: H. sapiens
<220> FEATURE:

<400> SEQUENCE: 663
ataccacggc caacatctcc 20

<210> SEQ ID NO 664
<211> LENGTH: 20
<212> TYPE: DNA
<213> ORGANISM: H. sapiens
<220> FEATURE:

<400> SEQUENCE: 664
cagctagctg cccagaggca 20

<210> SEQ ID NO 665
<211> LENGTH: 20
<212> TYPE: DNA
<213> ORGANISM: H. sapiens
<220> FEATURE:

<400> SEQUENCE: 665
aggagcttct tcagcctcta 20

<210> SEQ ID NO 666
<211> LENGTH: 20
<212> TYPE: DNA
<213> ORGANISM: H. sapiens
<220> FEATURE:

<400> SEQUENCE: 666
cctccgctca ggtgatggac 20

<210> SEQ ID NO 667
<211> LENGTH: 20

-continued

<212> TYPE: DNA
<213> ORGANISM: H. sapiens
<220> FEATURE:

<400> SEQUENCE: 667
gtggccgcgg tgttcatgca 20

<210> SEQ ID NO 668
<211> LENGTH: 20
<212> TYPE: DNA
<213> ORGANISM: H. sapiens
<220> FEATURE:

<400> SEQUENCE: 668
gcacaacctg ctgggcctgg 20

<210> SEQ ID NO 669
<211> LENGTH: 20
<212> TYPE: DNA
<213> ORGANISM: H. sapiens
<220> FEATURE:

<400> SEQUENCE: 669
agcttcttca gcctctacct 20

<210> SEQ ID NO 670
<211> LENGTH: 20
<212> TYPE: DNA
<213> ORGANISM: H. sapiens
<220> FEATURE:

<400> SEQUENCE: 670
aatgacaaca tgggcttctg 20

<210> SEQ ID NO 671
<211> LENGTH: 20
<212> TYPE: DNA
<213> ORGANISM: H. sapiens
<220> FEATURE:

<400> SEQUENCE: 671
cctgcacaac ctgctgggcc 20

<210> SEQ ID NO 672
<211> LENGTH: 20
<212> TYPE: DNA
<213> ORGANISM: H. sapiens
<220> FEATURE:

<400> SEQUENCE: 672
ccagtgtcac cacaacctga 20

<210> SEQ ID NO 673
<211> LENGTH: 20
<212> TYPE: DNA
<213> ORGANISM: H. sapiens
<220> FEATURE:

<400> SEQUENCE: 673
cagcaatgac aacatgggct 20

<210> SEQ ID NO 674
<211> LENGTH: 20
<212> TYPE: DNA
<213> ORGANISM: H. sapiens

-continued

<220> FEATURE:

<400> SEQUENCE: 674
tggacttcct gtttgagaag 20

<210> SEQ ID NO 675
<211> LENGTH: 20
<212> TYPE: DNA
<213> ORGANISM: H. sapiens
<220> FEATURE:

<400> SEQUENCE: 675
gcaacaccgc ttcgtgttca 20

<210> SEQ ID NO 676
<211> LENGTH: 20
<212> TYPE: DNA
<213> ORGANISM: H. sapiens
<220> FEATURE:

<400> SEQUENCE: 676
cttcctgttt gagaagtgga 20

<210> SEQ ID NO 677
<211> LENGTH: 20
<212> TYPE: DNA
<213> ORGANISM: H. sapiens
<220> FEATURE:

<400> SEQUENCE: 677
gcctctacct gggcatcggc 20

<210> SEQ ID NO 678
<211> LENGTH: 20
<212> TYPE: DNA
<213> ORGANISM: H. sapiens
<220> FEATURE:

<400> SEQUENCE: 678
ctccgctcag gtgatggact 20

<210> SEQ ID NO 679
<211> LENGTH: 20
<212> TYPE: DNA
<213> ORGANISM: H. sapiens
<220> FEATURE:

<400> SEQUENCE: 679
cgacaagtat tcctgctggc 20

<210> SEQ ID NO 680
<211> LENGTH: 20
<212> TYPE: DNA
<213> ORGANISM: H. sapiens
<220> FEATURE:

<400> SEQUENCE: 680
ctgctgctgg cctgccagcc 20

<210> SEQ ID NO 681
<211> LENGTH: 20
<212> TYPE: DNA
<213> ORGANISM: H. sapiens
<220> FEATURE:

-continued

<400> SEQUENCE: 681
cttctggtgg atcctgcggt 20

<210> SEQ ID NO 682
<211> LENGTH: 20
<212> TYPE: DNA
<213> ORGANISM: H. sapiens
<220> FEATURE:

<400> SEQUENCE: 682
tgggctgctc aggacccgct 20

<210> SEQ ID NO 683
<211> LENGTH: 20
<212> TYPE: DNA
<213> ORGANISM: H. sapiens
<220> FEATURE:

<400> SEQUENCE: 683
gttcaagaga tgcgggcccg 20

<210> SEQ ID NO 684
<211> LENGTH: 20
<212> TYPE: DNA
<213> ORGANISM: H. sapiens
<220> FEATURE:

<400> SEQUENCE: 684
catgggcttc tggtggatcc 20

<210> SEQ ID NO 685
<211> LENGTH: 20
<212> TYPE: DNA
<213> ORGANISM: H. sapiens
<220> FEATURE:

<400> SEQUENCE: 685
ttctggtgga tcctgcggtt 20

<210> SEQ ID NO 686
<211> LENGTH: 20
<212> TYPE: DNA
<213> ORGANISM: H. sapiens
<220> FEATURE:

<400> SEQUENCE: 686
cacaacctga gcctgctgcc 20

<210> SEQ ID NO 687
<211> LENGTH: 20
<212> TYPE: DNA
<213> ORGANISM: H. sapiens
<220> FEATURE:

<400> SEQUENCE: 687
ccaataccac ggccaacatc 20

<210> SEQ ID NO 688
<211> LENGTH: 20
<212> TYPE: DNA
<213> ORGANISM: H. sapiens
<220> FEATURE:

<400> SEQUENCE: 688

-continued gtacagcagc ttccaggtga 20

<210> SEQ ID NO 689
<211> LENGTH: 20
<212> TYPE: DNA
<213> ORGANISM: H. sapiens
<220> FEATURE:

<400> SEQUENCE: 689
gggctgctca ggacccgcta 20

<210> SEQ ID NO 690
<211> LENGTH: 20
<212> TYPE: DNA
<213> ORGANISM: H. sapiens
<220> FEATURE:

<400> SEQUENCE: 690
cagcttccag gtgatgtaca 20

<210> SEQ ID NO 691
<211> LENGTH: 20
<212> TYPE: DNA
<213> ORGANISM: H. sapiens
<220> FEATURE:

<400> SEQUENCE: 691
gccaatacca cggccaacat 20

<210> SEQ ID NO 692
<211> LENGTH: 20
<212> TYPE: DNA
<213> ORGANISM: H. sapiens
<220> FEATURE:

<400> SEQUENCE: 692
atgggcttct ggtggatcct 20

<210> SEQ ID NO 693
<211> LENGTH: 20
<212> TYPE: DNA
<213> ORGANISM: H. sapiens
<220> FEATURE:

<400> SEQUENCE: 693
cgtcttcctg gccatcctga 20

<210> SEQ ID NO 694
<211> LENGTH: 20
<212> TYPE: DNA
<213> ORGANISM: H. sapiens
<220> FEATURE:

<400> SEQUENCE: 694
cgctcaggtg atggacttcc 20

<210> SEQ ID NO 695
<211> LENGTH: 20
<212> TYPE: DNA
<213> ORGANISM: H. sapiens
<220> FEATURE:

<400> SEQUENCE: 695
gctagctgcc cagaggcatg 20

-continued

<210> SEQ ID NO 696
<211> LENGTH: 20
<212> TYPE: DNA
<213> ORGANISM: H. sapiens
<220> FEATURE:

<400> SEQUENCE: 696
tcgtgttcaa gagatgcggg 20

<210> SEQ ID NO 697
<211> LENGTH: 20
<212> TYPE: DNA
<213> ORGANISM: H. sapiens
<220> FEATURE:

<400> SEQUENCE: 697
ctgctggcct gccagccaca 20

<210> SEQ ID NO 698
<211> LENGTH: 20
<212> TYPE: DNA
<213> ORGANISM: H. sapiens
<220> FEATURE:

<400> SEQUENCE: 698
tgctggcctg ccagccacag 20

<210> SEQ ID NO 699
<211> LENGTH: 20
<212> TYPE: DNA
<213> ORGANISM: H. sapiens
<220> FEATURE:

<400> SEQUENCE: 699
tgggcttctg gtggatcctg 20

<210> SEQ ID NO 700
<211> LENGTH: 20
<212> TYPE: DNA
<213> ORGANISM: H. sapiens
<220> FEATURE:

<400> SEQUENCE: 700
atgcaccaca cagactacaa 20

<210> SEQ ID NO 701
<211> LENGTH: 20
<212> TYPE: DNA
<213> ORGANISM: H. sapiens
<220> FEATURE:

<400> SEQUENCE: 701
gctgctggcc tgccagccac 20

<210> SEQ ID NO 702
<211> LENGTH: 20
<212> TYPE: DNA
<213> ORGANISM: H. sapiens
<220> FEATURE:

<400> SEQUENCE: 702
tcaccacaac ctgagcctgc 20

<210> SEQ ID NO 703

-continued

<211> LENGTH: 20
<212> TYPE: DNA
<213> ORGANISM: H. sapiens
<220> FEATURE:

<400> SEQUENCE: 703
tcaggacccg ctacagccag 20

<210> SEQ ID NO 704
<211> LENGTH: 20
<212> TYPE: DNA
<213> ORGANISM: H. sapiens
<220> FEATURE:

<400> SEQUENCE: 704
gacaagtatt cctgctggcc 20

<210> SEQ ID NO 705
<211> LENGTH: 20
<212> TYPE: DNA
<213> ORGANISM: H. sapiens
<220> FEATURE:

<400> SEQUENCE: 705
gagcttcttc agcctctacc 20

<210> SEQ ID NO 706
<211> LENGTH: 20
<212> TYPE: DNA
<213> ORGANISM: H. sapiens
<220> FEATURE:

<400> SEQUENCE: 706
tcttcttcga cctcttcctc 20

<210> SEQ ID NO 707
<211> LENGTH: 20
<212> TYPE: DNA
<213> ORGANISM: H. sapiens
<220> FEATURE:

<400> SEQUENCE: 707
cacaaagtgc aacaccgctt 20

<210> SEQ ID NO 708
<211> LENGTH: 20
<212> TYPE: DNA
<213> ORGANISM: H. sapiens
<220> FEATURE:

<400> SEQUENCE: 708
gaaccttcga caagtattcc 20

<210> SEQ ID NO 709
<211> LENGTH: 20
<212> TYPE: DNA
<213> ORGANISM: H. sapiens
<220> FEATURE:

<400> SEQUENCE: 709
tgtcaccaca acctgagcct 20

<210> SEQ ID NO 710
<211> LENGTH: 20
<212> TYPE: DNA

<213> ORGANISM: H. sapiens
<220> FEATURE:

<400> SEQUENCE: 710
gcaccacaaa gtgcaacacc 20

<210> SEQ ID NO 711
<211> LENGTH: 20
<212> TYPE: DNA
<213> ORGANISM: H. sapiens
<220> FEATURE:

<400> SEQUENCE: 711
tggccgcggt gttcatgcaa 20

<210> SEQ ID NO 712
<211> LENGTH: 20
<212> TYPE: DNA
<213> ORGANISM: H. sapiens
<220> FEATURE:

<400> SEQUENCE: 712
agatgtacag cagcttccag 20

<210> SEQ ID NO 713
<211> LENGTH: 20
<212> TYPE: DNA
<213> ORGANISM: H. sapiens
<220> FEATURE:

<400> SEQUENCE: 713
ctggccatcc tgatcaactt 20

<210> SEQ ID NO 714
<211> LENGTH: 20
<212> TYPE: DNA
<213> ORGANISM: H. sapiens
<220> FEATURE:

<400> SEQUENCE: 714
tgcacaacct gctgggcctg 20

<210> SEQ ID NO 715
<211> LENGTH: 20
<212> TYPE: DNA
<213> ORGANISM: H. sapiens
<220> FEATURE:

<400> SEQUENCE: 715
caccgcttcg tgttcaagag 20

<210> SEQ ID NO 716
<211> LENGTH: 20
<212> TYPE: DNA
<213> ORGANISM: H. sapiens
<220> FEATURE:

<400> SEQUENCE: 716
taccacggcc aacatctcct 20

<210> SEQ ID NO 717
<211> LENGTH: 20
<212> TYPE: DNA
<213> ORGANISM: H. sapiens
<220> FEATURE:

<400> SEQUENCE: 717
ccagcaatga caacatgggc 20

<210> SEQ ID NO 718
<211> LENGTH: 20
<212> TYPE: DNA
<213> ORGANISM: H. sapiens
<220> FEATURE:

<400> SEQUENCE: 718
ttcttcagcc tctacctggg 20

<210> SEQ ID NO 719
<211> LENGTH: 20
<212> TYPE: DNA
<213> ORGANISM: H. sapiens
<220> FEATURE:

<400> SEQUENCE: 719
accagcaatg acaacatggg 20

<210> SEQ ID NO 720
<211> LENGTH: 20
<212> TYPE: DNA
<213> ORGANISM: H. sapiens
<220> FEATURE:

<400> SEQUENCE: 720
agtgcaacac cgcttcgtgt 20

<210> SEQ ID NO 721
<211> LENGTH: 20
<212> TYPE: DNA
<213> ORGANISM: H. sapiens
<220> FEATURE:

<400> SEQUENCE: 721
accacaacct gagcctgctg 20

<210> SEQ ID NO 722
<211> LENGTH: 20
<212> TYPE: DNA
<213> ORGANISM: H. sapiens
<220> FEATURE:

<400> SEQUENCE: 722
acctgcacaa cctgctgggc 20

<210> SEQ ID NO 723
<211> LENGTH: 20
<212> TYPE: DNA
<213> ORGANISM: H. sapiens
<220> FEATURE:

<400> SEQUENCE: 723
cgtgttcaag agatgcgggc 20

<210> SEQ ID NO 724
<211> LENGTH: 20
<212> TYPE: DNA
<213> ORGANISM: H. sapiens
<220> FEATURE:

<400> SEQUENCE: 724

-continued aagctcttct tcgacctctt 20

<210> SEQ ID NO 725
<211> LENGTH: 20
<212> TYPE: DNA
<213> ORGANISM: H. sapiens
<220> FEATURE:

<400> SEQUENCE: 725
cgcttcgtgt tcaagagatg 20

<210> SEQ ID NO 726
<211> LENGTH: 20
<212> TYPE: DNA
<213> ORGANISM: H. sapiens
<220> FEATURE:

<400> SEQUENCE: 726
agtgctggac cagcaatgac 20

<210> SEQ ID NO 727
<211> LENGTH: 20
<212> TYPE: DNA
<213> ORGANISM: H. sapiens
<220> FEATURE:

<400> SEQUENCE: 727
ttcaagagat gcgggcccga 20

<210> SEQ ID NO 728
<211> LENGTH: 20
<212> TYPE: DNA
<213> ORGANISM: H. sapiens
<220> FEATURE:

<400> SEQUENCE: 728
ctacagcctg tccctggggg 20

<210> SEQ ID NO 729
<211> LENGTH: 20
<212> TYPE: DNA
<213> ORGANISM: H. sapiens
<220> FEATURE:

<400> SEQUENCE: 729
gaccagcaat gacaacatgg 20

<210> SEQ ID NO 730
<211> LENGTH: 20
<212> TYPE: DNA
<213> ORGANISM: H. sapiens
<220> FEATURE:

<400> SEQUENCE: 730
tgcaacaccg cttcgtgttc 20

<210> SEQ ID NO 731
<211> LENGTH: 20
<212> TYPE: DNA
<213> ORGANISM: H. sapiens
<220> FEATURE:

<400> SEQUENCE: 731
ctggaccagc aatgacaaca 20

-continued

<210> SEQ ID NO 732
<211> LENGTH: 20
<212> TYPE: DNA
<213> ORGANISM: H. sapiens
<220> FEATURE:

<400> SEQUENCE: 732
aaccttcgac aagtattcct 20

<210> SEQ ID NO 733
<211> LENGTH: 20
<212> TYPE: DNA
<213> ORGANISM: H. sapiens
<220> FEATURE:

<400> SEQUENCE: 733
aagtgcaaca ccgcttcgtg 20

<210> SEQ ID NO 734
<211> LENGTH: 20
<212> TYPE: DNA
<213> ORGANISM: H. sapiens
<220> FEATURE:

<400> SEQUENCE: 734
agctagctgc ccagaggcat 20

<210> SEQ ID NO 735
<211> LENGTH: 20
<212> TYPE: DNA
<213> ORGANISM: H. sapiens
<220> FEATURE:

<400> SEQUENCE: 735
acagcagctt ccaggtgatg 20

<210> SEQ ID NO 736
<211> LENGTH: 20
<212> TYPE: DNA
<213> ORGANISM: H. sapiens
<220> FEATURE:

<400> SEQUENCE: 736
gcttcgtgtt caagagatgc 20

<210> SEQ ID NO 737
<211> LENGTH: 20
<212> TYPE: DNA
<213> ORGANISM: H. sapiens
<220> FEATURE:

<400> SEQUENCE: 737
cgcggtgttc atgcaatatg 20

<210> SEQ ID NO 738
<211> LENGTH: 20
<212> TYPE: DNA
<213> ORGANISM: H. sapiens
<220> FEATURE:

<400> SEQUENCE: 738
tgctcaggac ccgctacagc 20

-continued

<210> SEQ ID NO 739
<211> LENGTH: 20
<212> TYPE: DNA
<213> ORGANISM: H. sapiens
<220> FEATURE:

<400> SEQUENCE: 739
gctgctcagg acccgctaca 20

<210> SEQ ID NO 740
<211> LENGTH: 20
<212> TYPE: DNA
<213> ORGANISM: H. sapiens
<220> FEATURE:

<400> SEQUENCE: 740
agcagcttcc aggtgatgta 20

<210> SEQ ID NO 741
<211> LENGTH: 20
<212> TYPE: DNA
<213> ORGANISM: H. sapiens
<220> FEATURE:

<400> SEQUENCE: 741
ggcttctggt ggatcctgcg 20

<210> SEQ ID NO 742
<211> LENGTH: 20
<212> TYPE: DNA
<213> ORGANISM: H. sapiens
<220> FEATURE:

<400> SEQUENCE: 742
gaggagcttc ttcagcctct 20

<210> SEQ ID NO 743
<211> LENGTH: 20
<212> TYPE: DNA
<213> ORGANISM: H. sapiens
<220> FEATURE:

<400> SEQUENCE: 743
ttcctggcca tcctgatcaa 20

<210> SEQ ID NO 744
<211> LENGTH: 20
<212> TYPE: DNA
<213> ORGANISM: H. sapiens
<220> FEATURE:

<400> SEQUENCE: 744
ccacaaagtg caacaccgct 20

<210> SEQ ID NO 745
<211> LENGTH: 20
<212> TYPE: DNA
<213> ORGANISM: H. sapiens
<220> FEATURE:

<400> SEQUENCE: 745
gctgctgctg gcctgccagc 20

<210> SEQ ID NO 746
<211> LENGTH: 20

-continued

<212> TYPE: DNA
<213> ORGANISM: H. sapiens
<220> FEATURE:

<400> SEQUENCE: 746
aaagtgcaac accgcttcgt 20

<210> SEQ ID NO 747
<211> LENGTH: 20
<212> TYPE: DNA
<213> ORGANISM: H. sapiens
<220> FEATURE:

<400> SEQUENCE: 747
tgtggccgcg gtgttcatgc 20

<210> SEQ ID NO 748
<211> LENGTH: 20
<212> TYPE: DNA
<213> ORGANISM: H. sapiens
<220> FEATURE:

<400> SEQUENCE: 748
gggcttctgg tggatcctgc 20

<210> SEQ ID NO 749
<211> LENGTH: 20
<212> TYPE: DNA
<213> ORGANISM: H. sapiens
<220> FEATURE:

<400> SEQUENCE: 749
tacagcctgt ccctgggggc 20

<210> SEQ ID NO 750
<211> LENGTH: 20
<212> TYPE: DNA
<213> ORGANISM: H. sapiens
<220> FEATURE:

<400> SEQUENCE: 750
ccgcggtgtt catgcaatat 20

<210> SEQ ID NO 751
<211> LENGTH: 20
<212> TYPE: DNA
<213> ORGANISM: H. sapiens
<220> FEATURE:

<400> SEQUENCE: 751
ccttcgacaa gtattcctgc 20

<210> SEQ ID NO 752
<211> LENGTH: 20
<212> TYPE: DNA
<213> ORGANISM: H. sapiens
<220> FEATURE:

<400> SEQUENCE: 752
gcagcttcca ggtgatgtac 20

<210> SEQ ID NO 753
<211> LENGTH: 20
<212> TYPE: DNA
<213> ORGANISM: H. sapiens

-continued

<220> FEATURE:

<400> SEQUENCE: 753
ccagtgctgg accagcaatg 20

<210> SEQ ID NO 754
<211> LENGTH: 20
<212> TYPE: DNA
<213> ORGANISM: H. sapiens
<220> FEATURE:

<400> SEQUENCE: 754
caacaccgct tcgtgttcaa 20

<210> SEQ ID NO 755
<211> LENGTH: 20
<212> TYPE: DNA
<213> ORGANISM: H. sapiens
<220> FEATURE:

<400> SEQUENCE: 755
tgacaacatg ggcttctggt 20

<210> SEQ ID NO 756
<211> LENGTH: 20
<212> TYPE: DNA
<213> ORGANISM: M. musculus
<220> FEATURE:

<400> SEQUENCE: 756
caacctctgc cagatgtggg 20

<210> SEQ ID NO 757
<211> LENGTH: 20
<212> TYPE: DNA
<213> ORGANISM: M. musculus
<220> FEATURE:

<400> SEQUENCE: 757
gtttgagaag tggaagctct 20

<210> SEQ ID NO 758
<211> LENGTH: 20
<212> TYPE: DNA
<213> ORGANISM: M. musculus
<220> FEATURE:

<400> SEQUENCE: 758
tggaagctct atagtgacca 20

<210> SEQ ID NO 759
<211> LENGTH: 20
<212> TYPE: DNA
<213> ORGANISM: M. musculus
<220> FEATURE:

<400> SEQUENCE: 759
caccacaacc taagcctgct 20

<210> SEQ ID NO 760
<211> LENGTH: 20
<212> TYPE: DNA
<213> ORGANISM: M. musculus
<220> FEATURE:

-continued

<400> SEQUENCE: 760
cactgccaac atttcctgcc 20

<210> SEQ ID NO 761
<211> LENGTH: 20
<212> TYPE: DNA
<213> ORGANISM: M. musculus
<220> FEATURE:

<400> SEQUENCE: 761
gtgttcaaga ggtgtgggcc 20

<210> SEQ ID NO 762
<211> LENGTH: 20
<212> TYPE: DNA
<213> ORGANISM: M. musculus
<220> FEATURE:

<400> SEQUENCE: 762
agatcgaggt ccagaagggg 20

<210> SEQ ID NO 763
<211> LENGTH: 20
<212> TYPE: DNA
<213> ORGANISM: M. musculus
<220> FEATURE:

<400> SEQUENCE: 763
gggctacagt ctgtccctgg 20

<210> SEQ ID NO 764
<211> LENGTH: 20
<212> TYPE: DNA
<213> ORGANISM: M. musculus
<220> FEATURE:

<400> SEQUENCE: 764
gggcctcagg aagctgcact 20

<210> SEQ ID NO 765
<211> LENGTH: 20
<212> TYPE: DNA
<213> ORGANISM: M. musculus
<220> FEATURE:

<400> SEQUENCE: 765
ccctgggtgg tggtcaagtg 20

<210> SEQ ID NO 766
<211> LENGTH: 20
<212> TYPE: DNA
<213> ORGANISM: M. musculus
<220> FEATURE:

<400> SEQUENCE: 766
tgctggacca gcaatgacaa 20

<210> SEQ ID NO 767
<211> LENGTH: 20
<212> TYPE: DNA
<213> ORGANISM: M. musculus
<220> FEATURE:

<400> SEQUENCE: 767

-continued atgggattct ggtggatcct 20

<210> SEQ ID NO 768
<211> LENGTH: 20
<212> TYPE: DNA
<213> ORGANISM: M. musculus
<220> FEATURE:

<400> SEQUENCE: 768
gccaggtcca cgctgaccct 20

<210> SEQ ID NO 769
<211> LENGTH: 20
<212> TYPE: DNA
<213> ORGANISM: M. musculus
<220> FEATURE:

<400> SEQUENCE: 769
gcaacctgag gagaggtgca 20

<210> SEQ ID NO 770
<211> LENGTH: 20
<212> TYPE: DNA
<213> ORGANISM: M. musculus
<220> FEATURE:

<400> SEQUENCE: 770
agaggtgcac acactctgag 20

<210> SEQ ID NO 771
<211> LENGTH: 20
<212> TYPE: DNA
<213> ORGANISM: M. musculus
<220> FEATURE:

<400> SEQUENCE: 771
tgcacacact ctgaggacct 20

<210> SEQ ID NO 772
<211> LENGTH: 20
<212> TYPE: DNA
<213> ORGANISM: M. musculus
<220> FEATURE:

<400> SEQUENCE: 772
ctaggtgtgc aacctctgcc 20

<210> SEQ ID NO 773
<211> LENGTH: 20
<212> TYPE: DNA
<213> ORGANISM: M. musculus
<220> FEATURE:

<400> SEQUENCE: 773
tggctaccca gaggcatgcc 20

<210> SEQ ID NO 774
<211> LENGTH: 20
<212> TYPE: DNA
<213> ORGANISM: M. musculus
<220> FEATURE:

<400> SEQUENCE: 774
tgtttgagaa gtggaagctc 20

-continued

<210> SEQ ID NO 775
<211> LENGTH: 20
<212> TYPE: DNA
<213> ORGANISM: M. musculus
<220> FEATURE:

<400> SEQUENCE: 775
ccacctactg agctggtctg 20

<210> SEQ ID NO 776
<211> LENGTH: 20
<212> TYPE: DNA
<213> ORGANISM: M. musculus
<220> FEATURE:

<400> SEQUENCE: 776
actcctgctg gcctgacacc 20

<210> SEQ ID NO 777
<211> LENGTH: 20
<212> TYPE: DNA
<213> ORGANISM: M. musculus
<220> FEATURE:

<400> SEQUENCE: 777
tgccacaaag tgcagcaccg 20

<210> SEQ ID NO 778
<211> LENGTH: 20
<212> TYPE: DNA
<213> ORGANISM: M. musculus
<220> FEATURE:

<400> SEQUENCE: 778
cagcaccgcc tagtgttcaa 20

<210> SEQ ID NO 779
<211> LENGTH: 20
<212> TYPE: DNA
<213> ORGANISM: M. musculus
<220> FEATURE:

<400> SEQUENCE: 779
cagtgggttc gagggccacg 20

<210> SEQ ID NO 780
<211> LENGTH: 20
<212> TYPE: DNA
<213> ORGANISM: M. musculus
<220> FEATURE:

<400> SEQUENCE: 780
agtctgtccc tgggggcctt 20

<210> SEQ ID NO 781
<211> LENGTH: 20
<212> TYPE: DNA
<213> ORGANISM: M. musculus
<220> FEATURE:

<400> SEQUENCE: 781
gcgctggtca tcctgctggg 20

<210> SEQ ID NO 782

<211> LENGTH: 20
<212> TYPE: DNA
<213> ORGANISM: M. musculus
<220> FEATURE:

<400> SEQUENCE: 782
tcctgctggg cctcaggaag 20

<210> SEQ ID NO 783
<211> LENGTH: 20
<212> TYPE: DNA
<213> ORGANISM: M. musculus
<220> FEATURE:

<400> SEQUENCE: 783
gtgctcaagg ctggctctgt 20

<210> SEQ ID NO 784
<211> LENGTH: 20
<212> TYPE: DNA
<213> ORGANISM: M. musculus
<220> FEATURE:

<400> SEQUENCE: 784
ggctgcagag tggccacagt 20

<210> SEQ ID NO 785
<211> LENGTH: 20
<212> TYPE: DNA
<213> ORGANISM: M. musculus
<220> FEATURE:

<400> SEQUENCE: 785
ggccacagtg atcatgcagt 20

<210> SEQ ID NO 786
<211> LENGTH: 20
<212> TYPE: DNA
<213> ORGANISM: M. musculus
<220> FEATURE:

<400> SEQUENCE: 786
atcatgcagt acggcatcat 20

<210> SEQ ID NO 787
<211> LENGTH: 20
<212> TYPE: DNA
<213> ORGANISM: M. musculus
<220> FEATURE:

<400> SEQUENCE: 787
gtgtacctgt acagcctgct 20

<210> SEQ ID NO 788
<211> LENGTH: 20
<212> TYPE: DNA
<213> ORGANISM: M. musculus
<220> FEATURE:

<400> SEQUENCE: 788
cagtgctgga ccagcaatga 20

<210> SEQ ID NO 789
<211> LENGTH: 20
<212> TYPE: DNA

-continued

<213> ORGANISM: M. musculus
<220> FEATURE:

<400> SEQUENCE: 789
cttcttgtgg ccaagctgcg 20

<210> SEQ ID NO 790
<211> LENGTH: 20
<212> TYPE: DNA
<213> ORGANISM: M. musculus
<220> FEATURE:

<400> SEQUENCE: 790
gcccatcaga tgcactatgc 20

<210> SEQ ID NO 791
<211> LENGTH: 20
<212> TYPE: DNA
<213> ORGANISM: M. musculus
<220> FEATURE:

<400> SEQUENCE: 791
ttcctcagct ccttccaggg 20

<210> SEQ ID NO 792
<211> LENGTH: 20
<212> TYPE: DNA
<213> ORGANISM: M. musculus
<220> FEATURE:

<400> SEQUENCE: 792
ctctactgtt tcctcaacaa 20

<210> SEQ ID NO 793
<211> LENGTH: 20
<212> TYPE: DNA
<213> ORGANISM: M. musculus
<220> FEATURE:

<400> SEQUENCE: 793
atggcaagaa ggcaaagctc 20

<210> SEQ ID NO 794
<211> LENGTH: 20
<212> TYPE: DNA
<213> ORGANISM: M. musculus
<220> FEATURE:

<400> SEQUENCE: 794
caaagctctt caggaggaaa 20

<210> SEQ ID NO 795
<211> LENGTH: 20
<212> TYPE: DNA
<213> ORGANISM: M. musculus
<220> FEATURE:

<400> SEQUENCE: 795
agcagccatg gcagccacat 20

<210> SEQ ID NO 796
<211> LENGTH: 20
<212> TYPE: DNA
<213> ORGANISM: M. musculus
<220> FEATURE:

<400> SEQUENCE: 796
tccctgtgag aaacttcagc 20

<210> SEQ ID NO 797
<211> LENGTH: 20
<212> TYPE: DNA
<213> ORGANISM: M. musculus
<220> FEATURE:

<400> SEQUENCE: 797
tcagcttatg agtgcaggca 20

<210> SEQ ID NO 798
<211> LENGTH: 20
<212> TYPE: DNA
<213> ORGANISM: M. musculus
<220> FEATURE:

<400> SEQUENCE: 798
gcagcagtgg gactggctgt 20

<210> SEQ ID NO 799
<211> LENGTH: 20
<212> TYPE: DNA
<213> ORGANISM: M. musculus
<220> FEATURE:

<400> SEQUENCE: 799
tggccagtag tctcccaagg 20

<210> SEQ ID NO 800
<211> LENGTH: 20
<212> TYPE: DNA
<213> ORGANISM: M. musculus
<220> FEATURE:

<400> SEQUENCE: 800
cccacctgaa tctccacttg 20

<210> SEQ ID NO 801
<211> LENGTH: 20
<212> TYPE: DNA
<213> ORGANISM: M. musculus
<220> FEATURE:

<400> SEQUENCE: 801
ggttgtgttc aagaaagggc 20

<210> SEQ ID NO 802
<211> LENGTH: 20
<212> TYPE: DNA
<213> ORGANISM: M. musculus
<220> FEATURE:

<400> SEQUENCE: 802
aggacaaccc agagccagat 20

<210> SEQ ID NO 803
<211> LENGTH: 20
<212> TYPE: DNA
<213> ORGANISM: M. musculus
<220> FEATURE:

<400> SEQUENCE: 803
agagccagat gcccggccaa 20

<210> SEQ ID NO 804
<211> LENGTH: 20
<212> TYPE: DNA
<213> ORGANISM: M. musculus
<220> FEATURE:

<400> SEQUENCE: 804
gcccggccaa ggttgaagag 20

<210> SEQ ID NO 805
<211> LENGTH: 20
<212> TYPE: DNA
<213> ORGANISM: M. musculus
<220> FEATURE:

<400> SEQUENCE: 805
cagcaagaca gcagcttgta 20

<210> SEQ ID NO 806
<211> LENGTH: 20
<212> TYPE: DNA
<213> ORGANISM: M. musculus
<220> FEATURE:

<400> SEQUENCE: 806
gtcctagcct ggcacaggcc 20

<210> SEQ ID NO 807
<211> LENGTH: 20
<212> TYPE: DNA
<213> ORGANISM: M. musculus
<220> FEATURE:

<400> SEQUENCE: 807
gttggatatg atggagaagc 20

<210> SEQ ID NO 808
<211> LENGTH: 20
<212> TYPE: DNA
<213> ORGANISM: M. musculus
<220> FEATURE:

<400> SEQUENCE: 808
atctatgaac tctgagtgtt 20

<210> SEQ ID NO 809
<211> LENGTH: 20
<212> TYPE: DNA
<213> ORGANISM: M. musculus
<220> FEATURE:

<400> SEQUENCE: 809
gaactctgag tgttcccatg 20

<210> SEQ ID NO 810
<211> LENGTH: 20
<212> TYPE: DNA
<213> ORGANISM: M. musculus
<220> FEATURE:

<400> SEQUENCE: 810
tacccagata tgtccttcag 20

-continued

<210> SEQ ID NO 811
<211> LENGTH: 20
<212> TYPE: DNA
<213> ORGANISM: M. musculus
<220> FEATURE:

<400> SEQUENCE: 811
cttggtctcg cctttgttac 20

<210> SEQ ID NO 812
<211> LENGTH: 20
<212> TYPE: DNA
<213> ORGANISM: M. musculus
<220> FEATURE:

<400> SEQUENCE: 812
accttcacag agctggtctg 20

<210> SEQ ID NO 813
<211> LENGTH: 20
<212> TYPE: DNA
<213> ORGANISM: M. musculus
<220> FEATURE:

<400> SEQUENCE: 813
ccatgcccag tgcagcaccg 20

<210> SEQ ID NO 814
<211> LENGTH: 20
<212> TYPE: DNA
<213> ORGANISM: M. musculus
<220> FEATURE:

<400> SEQUENCE: 814
gtcaggttgc ccatccttgg 20

<210> SEQ ID NO 815
<211> LENGTH: 20
<212> TYPE: DNA
<213> ORGANISM: M. musculus
<220> FEATURE:

<400> SEQUENCE: 815
tcatgaggcc ttgggcttgg 20

<210> SEQ ID NO 816
<211> LENGTH: 20
<212> TYPE: DNA
<213> ORGANISM: M. musculus
<220> FEATURE:

<400> SEQUENCE: 816
ctggtcctct gcagcctgag 20

<210> SEQ ID NO 817
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 817 ctgctagcc tctggatttga 20

-continued

<210> SEQ ID NO 818
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 818
ccttccctga aggttcctcc 20

<210> SEQ ID NO 819
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 819
gcgatttccc gttttgacct 20

<210> SEQ ID NO 820
<211> LENGTH: 20
<212> TYPE: DNA
<213> ORGANISM: Artificial Sequence
<220> FEATURE:
<221> NAME/KEY: unsure
<222> LOCATION: (1)..(20)
<223> OTHER INFORMATION: Antisense Oligonucleotide

<400> SEQUENCE: 820
nnnnnnnnnn nnnnnnnnnn 20

<210> SEQ ID NO 821
<211> LENGTH: 16
<212> TYPE: DNA
<213> ORGANISM: Artificial Sequence
<220> FEATURE:
<223> OTHER INFORMATION: primer

<400> SEQUENCE: 821
actgcacccg caacgc 16

<210> SEQ ID NO 822
<211> LENGTH: 18
<212> TYPE: DNA
<213> ORGANISM: Artificial Sequence
<220> FEATURE:
<223> OTHER INFORMATION: primer

<400> SEQUENCE: 822
cacggagctg gccttcag 18

<210> SEQ ID NO 823
<211> LENGTH: 26
<212> TYPE: DNA
<213> ORGANISM: Artificial Sequence
<220> FEATURE:
<223> OTHER INFORMATION: probe

<400> SEQUENCE: 823
atccacgcga acctgtttgt gtcctt 26